US012793838B2

(12) United States Patent
Pecora et al.

(10) Patent No.: US 12,793,838 B2
(45) Date of Patent: Nov. 10, 2026

(54) CLINICAL OUTCOME TRACKING AND ANALYSIS SYSTEMS AND METHODS EMPLOYING PROVISIONAL NODAL ADDRESSES RELEVANT TO TREATMENT AND REFINED NODAL ADDRESSES RELEVANT TO PROGNOSIS-RELATED EXPECTED OUTCOME AND RISK ASSESSMENT

(71) Applicant: COTA, Inc., Boston, MA (US)

(72) Inventors: Andrew L. Pecora, Rumson, NJ (US); Andrew Norden, Boston, MA (US)

(73) Assignee: COTA, Inc., Boston, MA (US)

( * ) Notice: Subject to any disclaimer, the term of this patent is extended or adjusted under 35 U.S.C. 154(b) by 531 days.

(21) Appl. No.: 17/014,885

(22) Filed: Sep. 8, 2020

(65) Prior Publication Data

US 2021/0082573 A1 Mar. 18, 2021

Related U.S. Application Data

(60) Provisional application No. 62/900,135, filed on Sep. 13, 2019.

(51) Int. Cl.

| | |
|---|---|
| ***G16H 40/20*** | (2018.01) |
| ***G16H 10/20*** | (2018.01) |
| ***G16H 10/60*** | (2018.01) |
| ***G16H 50/30*** | (2018.01) |
| ***G16H 50/70*** | (2018.01) |
| ***G16H 70/20*** | (2018.01) |
| ***G16H 70/60*** | (2018.01) |

(52) U.S. Cl.

CPC ............ *G16H 40/20* (2018.01); *G16H 10/20* (2018.01); *G16H 10/60* (2018.01); *G16H 50/30* (2018.01); *G16H 50/70* (2018.01); *G16H 70/20* (2018.01); *G16H 70/60* (2018.01)

(58) Field of Classification Search

CPC ........ G16H 40/20; G16H 10/20; G16H 10/60; G16H 50/30; G16H 50/70; G16H 70/20; G16H 70/60; G16H 20/00; G06Q 40/12

See application file for complete search history.

(56) References Cited

U.S. PATENT DOCUMENTS

| | | | |
|---|---|---|---|
| 6,699,193 | B2 | 3/2004 | Crutchfield et al. |
| 7,774,377 | B2 | 8/2010 | Schoenberg |
| 8,019,552 | B2 | 9/2011 | Dai et al. |

(Continued)

FOREIGN PATENT DOCUMENTS

| | | |
|---|---|---|
| EP | 0 402 884 | 12/1990 |
| JP | 2003-310557 A | 11/2003 |

(Continued)

OTHER PUBLICATIONS

Smith et al. U.S. Appl. No. 15/341,847. Published claim amendments dated Jun. 21, 2018 (Year: 2018).*

(Continued)

*Primary Examiner* — Mamon Obeid

(74) *Attorney, Agent, or Firm* — Foley & Lardner LLP

(57) ABSTRACT

Described herein are systems, method, and non-transitory computer-readable media employing provisional nodal addresses and refined nodal addresses to assist health care providers in guiding treatment decisions and to provide an expected outcome for a patient diagnosed with a disease.

31 Claims, 35 Drawing Sheets

(56) References Cited

U.S. PATENT DOCUMENTS

| | | | | |
|---|---|---|---|---|
| 8,731,648 | B2 | 5/2014 | Bardy | |
| 9,262,642 | B1 | 2/2016 | Roth et al. | |
| 9,378,531 | B2 | 6/2016 | Pecora | |
| 9,646,135 | B2 * | 5/2017 | Pecora | G16H 10/60 |
| 9,734,288 | B2 | 8/2017 | Pecora | |
| 9,734,289 | B2 | 8/2017 | Pecora | |
| 9,734,291 | B2 | 8/2017 | Pecora | |
| 10,902,953 | B2 | 1/2021 | Pecora | |
| 12,159,699 | B2 * | 12/2024 | Englehart | G16H 10/60 |
| 2005/0240444 | A1 * | 10/2005 | Wooten | G06Q 30/02 705/3 |
| 2006/0041661 | A1 | 2/2006 | Erickson et al. | |
| 2008/0033894 | A1 | 2/2008 | Steck et al. | |
| 2008/0091472 | A1 | 4/2008 | Hoppe | |
| 2008/0312199 | A1 | 12/2008 | Glinsky | |
| 2008/0312959 | A1 | 12/2008 | Rose et al. | |
| 2009/0086745 | A1 | 4/2009 | Shufrun et al. | |
| 2009/0204430 | A1 | 8/2009 | Gliklich | |
| 2012/0029939 | A1 | 2/2012 | Danielson et al. | |
| 2012/0053425 | A1 | 3/2012 | Michelson et al. | |
| 2012/0130737 | A1 | 5/2012 | Finizio et al. | |
| 2012/0166218 | A1 | 6/2012 | Reiner | |
| 2012/0271612 | A1 | 10/2012 | Barsoum et al. | |
| 2013/0058924 | A1 | 3/2013 | Gutin et al. | |
| 2013/0226612 | A1 | 8/2013 | Carmeli et al. | |
| 2014/0006044 | A1 | 1/2014 | Pradhan et al. | |
| 2014/0244277 | A1 | 8/2014 | Krishna Rao et al. | |
| 2014/0359422 | A1 * | 12/2014 | Bassett, Jr. | G16B 20/00 707/754 |
| 2015/0100341 | A1 | 4/2015 | Pecora | |
| 2016/0253473 | A1 | 9/2016 | Anderson et al. | |
| 2017/0061086 | A1 * | 3/2017 | Pecora | G16H 10/60 |
| 2018/0056130 | A1 * | 3/2018 | Bitran | A63B 24/0075 |
| 2018/0121618 | A1 | 5/2018 | Smith et al. | |
| 2018/0293352 | A1 | 10/2018 | Goldberg et al. | |
| 2018/0293353 | A1 | 10/2018 | Goldberg et al. | |
| 2020/0388029 | A1 * | 12/2020 | Saltz | G06V 10/267 |
| 2021/0082573 | A1 * | 3/2021 | Pecora | G06Q 40/12 |
| 2023/0395211 | A1 * | 12/2023 | Englehart | G16H 40/67 |

FOREIGN PATENT DOCUMENTS

| | | | |
|---|---|---|---|
| JP | 2004-133826 | A | 4/2004 |
| JP | 2005-223629 | A | 8/2005 |
| JP | 2007-026172 | A | 2/2007 |
| JP | 2016-153961 | A | 8/2016 |
| JP | 2017-049985 | A | 3/2017 |
| WO | 2000/042533 | A1 | 7/2000 |
| WO | 2009/049277 | A1 | 4/2009 |
| WO | 2013/093692 | A2 | 6/2013 |
| WO | WO-2019/108888 | A1 | 6/2019 |
| WO | WO-2021/050438 | | 3/2021 |

OTHER PUBLICATIONS

Gray1 et al (Independent validation of the PREDICT breast cancer prognosis prediction tool in 45,789 patients using Scottish Cancer Registry data ) (Year: 2018).*

U.S. Appl. No. 14/507,640, filed Oct. 6, 2014, US-2015-0100341-A1, Abandoned.

U.S. Appl. No. 15/233,577, filed Aug. 10, 2016, U.S. Pat. No. 9,646,135, Issued.

Boland et al., Microsatellite instability in colorectal cancer. Gastroenterology. Jun. 2010;138(6):2073-2087.e3.

Geraci et al., Comorbid disease and cancer. the need for more relevant conceptual models in health services research. J Clin Oncol. Oct. 20, 2005;23(30):7399-404.

International Search Report and Written Opinion for Application No. PCT/US2020/049749, dated Nov. 27, 2020, 10 pages.

Extended European European Search Report for EP Appln. No. 20862216.7, dated Sep. 19, 2023.

U.S. Appl. No. 14/507,640, filed Oct. 6, 2014, 2015-0100341, Abandoned.

U.S. Appl. No. 14/594,969, filed Jan. 12, 2015, U.S. Pat. No. 9,378,531, Issued.

U.S. Appl. No. 15/233,548, filed Aug. 10, 2016, U.S. Pat. No. 9,734,288, Issued.

U.S. Appl. No. 15/233,564, filed Aug. 10, 2016, U.S. Pat. No. 9,734,289, Issued.

U.S. Appl. No. 15/233,577, filed Aug. 10, 2016, U.S. Pat. No. 3,946,135, Issued.

U.S. Appl. No. 15/351,099, filed Nov. 14, 2016, U.S. Pat. No. 9,734,291, Issued.

U.S. Appl. No. 15/894,618, filed Feb. 12, 2018, U.S. Pat. No. 10,902,953, Issued.

Notice of Reasons for Refusal Office Action on Japanese Application No. 2022-516019 dated Sep. 26, 2024 (9 pages).

Office Action issued in CA Application No. 3,153,930 dated Aug. 30, 2024 (5 Pages).

CN Office Action for Application No. 202080078979.8 mailing date Sep. 24, 2025, 14 pages with English machine translation.

AU Examination Report for Application No. 2020345630 mailing date Apr. 10, 2025, 4 pages.

AU Examination Report for Application No. 2020345630 mailing date Aug. 15, 2025, 3 pages.

JP Office Action for Application No. 2022516019 mailing date Jan. 7, 2025, 4 pages with English translation.

KR Office Action for Application No. 1020227011007 mailing date Oct. 30, 2025, 22 pages with English translation.

* cited by examiner

1500

DECISION SUPPORT

2400

| Color | Her2neu | 2008 | 2009 | 2010 | 2011 | 2012 | 2013 | Total | Living | Percentage |
|---|---|---|---|---|---|---|---|---|---|---|
| | Not assessed | 0 | 2 | 247 | 33 | 24 | 11 | 317 | 302 | 10.8% |
| | Negative | 1 | 7 | 1504 | 280 | 217 | 102 | 2111 | 2025 | 72.4% |
| | Positive | 1 | 1 | 358 | 50 | 54 | 28 | 492 | 470 | 16.8% |
| | Total | 2 | 10 | 2109 | 363 | 295 | 141 | 2920 | 2797 | 100% |

2500

View Report

* Independent Variable: Stage

Download PDF

All G2 tumor grade
breast cancers by Stage

COTA Graph for: Breast Oncology

*Cancer Site/ Subtype: Breast Cancer, From Year: 2008 To Year: 2013 Tumor Grade: G2 Intermediate combined histologic grade (moderately favorable)*

| Color | Stage | 2008 | 2009 | 2010 | 2011 | 2012 | 2013 | Total | Living | Percentage |
|---|---|---|---|---|---|---|---|---|---|---|
| | 0 | 0 | 1 | 99 | 28 | 27 | 12 | 167 | 166 | 10.57% |
| | IA | 1 | 2 | 463 | 74 | 68 | 19 | 627 | 616 | 39.24% |
| | IB | 0 | 0 | 2 | 3 | 5 | 1 | 11 | 11 | 0.7% |
| | IIA | 0 | 1 | 293 | 47 | 23 | 13 | 377 | 369 | 23.5% |
| | IIB | 0 | 1 | 104 | 16 | 17 | 8 | 146 | 142 | 9.04% |
| | IIIA | 0 | 0 | 85 | 10 | 11 | 2 | 108 | 102 | 6.5% |
| | IIIB | 0 | 0 | 17 | 3 | 1 | 1 | 22 | 22 | 1.4% |
| | IIIC | 0 | 0 | 25 | 3 | 1 | 1 | 30 | 30 | 1.91% |
| | IV | 0 | 0 | 69 | 9 | 12 | 3 | 93 | 75 | 4.78% |
| | N/A | 0 | 0 | 11 | 8 | 16 | 2 | 37 | 37 | 2.36% |
| | Total | 1 | 5 | 1168 | 201 | 181 | 62 | 1618 | 1570 | 100% |

2600

| Color | Her2neu | 2008 | 2009 | 2010 | 2011 | 2012 | 2013 | Total | Living | Percentage |
|---|---|---|---|---|---|---|---|---|---|---|
| | Not assessed | 0 | 0 | 11 | 0 | 0 | 0 | 11 | 11 | 3.15% |
| | Negative | 0 | 2 | 81 | 14 | 7 | 3 | 107 | 104 | 29.8% |
| | Positive | 1 | 0 | 169 | 29 | 30 | 11 | 240 | 234 | 67.05% |
| | Total | 1 | 2 | 261 | 43 | 37 | 14 | 358 | 349 | 100% |

2800

Dr John Doe (Black) v.
the aggregate (Blue)

View Analysis

Print Preview

Curve Details

| Curve | 6 Months | 1 YR | 2 Yrs | 3 Yrs | 4 Yrs | 5 Yrs | 10 Yrs | 15 Yrs |
|---|---|---|---|---|---|---|---|---|
| Physician1 | 95.36%-167 | 93.49%-164 | 87.92%-155 | 81.87%-144 | 80.41%-141 | 76.18%-134 | - | - |
| Physician2 | 93.22%-69 | 88.93%-66 | 85.59%-64 | 79.16%-58 | 76.34%-56 | 76.34%-56 | - | - |

Meter indicated Dr. John Doe is trending
in the right direction

CLINICAL OUTCOME TRACKING AND ANALYSIS SYSTEMS AND METHODS EMPLOYING PROVISIONAL NODAL ADDRESSES RELEVANT TO TREATMENT AND REFINED NODAL ADDRESSES RELEVANT TO PROGNOSIS-RELATED EXPECTED OUTCOME AND RISK ASSESSMENT

CROSS-REFERENCE TO RELATED APPLICATION

This non-provisional application claims the benefit of priority to U.S. provisional application 62/900,135 (filed Sep. 13, 2019), which is incorporated herein by reference in its entirety.

FIELD

The present disclosure relates to systems and methods to facilitate early treatment support and later determination of prognosis-related expected outcome of patients having a disease or disorder.

BACKGROUND

As the general population is living longer, medical costs associated with the aging population are increasing. The costs associated with diseases, such as cancer, are typically enormous.

Some public health care payers (e.g., Medicare) and some private health care payers (e.g., insurers) are transitioning, at least in part, from mainly fee-for-service based reimbursement models to models that are at least, in part, value-based with the goal of aligning payment with objective measures of clinical quality and avoiding unnecessary care and associated unnecessary expenses. For example, some value-based models include a pay for performance model that ties reimbursement to expected patient outcome with reduced reimbursement for worse than expected patient outcome, thereby providing financial incentives for a health care provider to meet or exceed the expected patient outcome for a patient. As another example, some value-based models include a bundled payment/episode of care model that provides a single bundled payment for total treatment costs associated with a specific procedure or condition, thereby providing financial incentives for a heath care provider to improve efficiency, coordinate care and avoid unnecessary care and associated unnecessary costs. Some value-based models include both pay-for-performance aspects and bundled payment/episode of care aspects.

However, value-based models present additional challenges. For example, many current methods of determining what an expected clinical outcome should be for a patient do not efficiently and accurately account for many of variables that can affect clinical outcome for the particular patient, resulting in an inaccurate estimate for the expected clinical outcome of the patient. As another example, many current methods of providing a single bundled payment for treatment of a specific procedure or condition do not account for many variables that can affect the course of treatment for a particular patient, resulting in the bundle payment being mismatched to the services that would be required for treatment of the particular patient.

Some health care payers use models that employ risk adjustment, which is a statistical process that takes into account the underlying health status and health spending of enrollees in an insurance plan when looking at their healthcare outcomes or health care costs. However, many current methods of risk adjustment do not efficiently and effectively identify how patients should be grouped in the statistical process so that like patients are compared to like patients with respect to treatment, outcome and costs.

SUMMARY OF THE INVENTION

Embodiments include methods, systems and computer readable media that employ provisional nodal addresses and refined nodal address to guide early treatment decisions and provide an estimated prognosis-related outcome for a patient of interest diagnosed with a disease, e.g., a cancer condition.

According to one aspect, the described invention provides a method for facilitating early treatment decisions and determining a prognosis-related expected outcome with respect to occurrence of a defined end point event for a patient of interest diagnosed with a disease, the method comprising: accessing or receiving a first data set comprising personal health information associated with the patient of interest at a first time or over a first period of time, the personal health information including information regarding phenotypic characteristics; assigning, based on the received or accessed first set of data, attributes for at least some of a set of preselected variables, the set of preselected variables including a set of treatment relevant variables and a set of prognosis or outcome relevant variables, where attributes are assigned for at least a minimum subset of the set of treatment relevant variables, assigning a provisional nodal address to the patient of interest based on the assigned attributes for the set of treatment relevant variables, the provisional nodal address being associated with predetermined treatment plan information for facilitation of treatment decisions, the predetermined treatment plan information tailored to a specific combination of attributes embodied in the provisional nodal address; providing the predetermined treatment plan information to a health care provider of the patient of interest to facilitate treatment decisions for the patient of interest; accessing or receiving a second set of data including updated and/or additional personal health information associated with the patient of interest at a second time or over a second period of time later than the first time or the first period of time; assigning, based on the accessed or received second set of data, updated attributes for at least some of the set of preselected variables and/or new attributes for preselected variables that did not previously have an assigned attribute; where attributes are assigned for at least the minimum subset of the treatment relevant variables and at least the minimum subset of the prognosis or outcome relevant variables: assigning a refined nodal address to the patient of interest based on the current assigned attributes for the set of treatment relevant variables and the current assigned attributes for the set of prognosis or outcome relevant variables; and determining the prognosis-related expected outcome with respect to occurrence of the defined end point event for the patient based on the refined nodal address assigned to the patient of interest.

In one embodiment of the method, the minimum subset of the treatment relevant variables is the treatment relevant variables in the set of preselected variables required to provide preselected treatment relevant information tailored to a patient's specific combination of treatment relevant attributes to guide a treatment decision. In some embodiments, the minimum subset of the treatment relevant variables for the patient of interest depends, at least in part, on a cancer type and a treatment intent for the patient of interest. In some embodiments, the minimum subset of the treatment relevant variables includes a cancer type and a treatment intent, and what other of the treatment relevant variables are included in the minimum subset of the treatment relevant variables depends, at least in part, on the cancer type and the treatment intent for the patient of interest. In some embodiments, the step of accessing or receiving a first data set comprising personal health information associated with the patient of interest at a first time or over a first period of time comprises accessing or receiving information regarding a cancer type and a treatment intent for the patient of interest; and the method further comprises determining the minimum subset of the treatment relevant variables based, at least in part, on the accessed or received information regarding the cancer type and the treatment intent for the patient of interest.

In some embodiments, the method further comprises presenting to the patient and/or a health care provider for the patient a user interface for entry of data in the first data set. In some embodiments, the user interface guides the user in entry of at least the minimum subset of treatment relevant variables. In some embodiments, the method further comprises presenting to the patient and/or a health care provider for the patient a user interface for entry of data in the first data set; and receiving information regarding the cancer type of the patient of interest and the treatment intent for the patient of interest; and after the determination of the minimum subset of the treatment relevant variables based on the received information regarding the cancer type of the patient of interest and the treatment intent for the patient of interest, guiding entry of the rest of the minimum subset of the treatment relevant variables via the user interface. In some embodiments, the minimum subset of the prognosis or outcome relevant variables is all of the prognosis or outcome relevant variables in the set of preselected variables required for statistical analysis of prior outcomes. In some embodiments, the second set of data includes data obtained from health records of the patient of interest. In some embodiments, the step of assigning, based on the accessed second set of data, updated attributes for at least some of the set of preselected variables and/or new attributes for preselected variables that did not previously have an assigned attribute comprises verifying and/or correcting detected issues in the second set of data to determine the updated or new attributes. In some embodiments, the first set of data includes data obtained from health records of the patient of interest.

In some embodiments, the method further comprises assessing the first set of data to determine if it is correct prior to assigning the attributes for at least some of the set of preselected variables. In some embodiments, the prognosis-related expected outcome for the patient of interest is determined from a statistical analysis of prior prognosis-related outcomes for patients in a prognosis or outcome based group of patients who were each assigned the same refined nodal address as that assigned to the patient of interest at a corresponding point in treatment and disease progression as that of the patient of interest. In some embodiments, the method further comprises statistically analyzing the prior outcomes for patients in the prognosis or outcome based group of patients to determine a current expected prognosis-related outcome for the patient of interest. In some embodiments, the current expected prognosis-related outcome is time to progression from start of second line therapy to start of third line therapy, wherein the patients in the prognosis or outcome based group of patients are patients who were each assigned at the start of second line therapy the same refined nodal address as that assigned to the patient of interest at the start of second line therapy.

In some embodiments, the method further comprises conducting an updated statistical analysis of the prior outcomes for patients in the prognosis or outcome based group of patients to determine an updated current expected prognosis-related outcome, and storing information regarding the updated current expected prognosis-related outcome. In some embodiments, the updated statistical analysis is conducted periodically.

In some embodiments, the prognosis-related expected outcome for the patient of interest is determined from a statistical analysis of prior prognosis-related outcomes for patients in a prognosis or outcome based group of patients at least some of whom were assigned the same refined nodal address as that assigned to the patient of interest at a corresponding point in treatment and disease progression as that of the patient of interest.

In some embodiments, the method further comprises transmitting information regarding the prognosis-related expected outcome to a client device associated with a health care provider of the patient or a payer for health care of the patient of interest.

In some embodiments, the method further comprises accessing information regarding an outcome for the patient of interest; comparing the outcome for the patient of interest to the determined prognosis-related expected outcome for the patient of interest; and transmitting information regarding the comparison to a health care provider for the patient or to a health care payer for the patient of interest.

In some embodiments, the method further comprises determining an expected cost of treatment of the patient of interest for the disease over a clinically relevant period based on cost of treatment for all patients in a prognosis or outcome based group of patients who were each assigned the same refined nodal address as that assigned to the patient of interest at a corresponding point in treatment and disease progression as that of the patient of interest. In some embodiments, the refined nodal address assigned to the patient the patient of interest has an associated expected cost of treatment for the disease from diagnosis to death or cure, the associated expected cost of treatment determined by statistically analyzing prior cost of treatment from diagnosis to death or cure for patients in the prognosis or outcome based group of patients who were each assigned the same refined nodal address as that assigned to the patient of interest at diagnosis.

In some embodiments, the method further comprises accessing information regarding billed costs for treatment of the patient of interest and determining a total cost for treatment of the patient of interest over the clinically relevant period; and comparing the expected cost for treatment of the patient of interest over a clinically relevant period with the total cost for treatment of the patient of interest over the clinically relevant period. In some embodiments, the clinically relevant period is from diagnosis to death or cure.

In some embodiments, the method further comprises comparing one or more outcomes for the patient of interest to one or more historical outcomes for patients in a prognosis or outcome based group of patients who were each assigned the same refined nodal address as that assigned to the patient of interest at diagnosis or at progression to determine if the one or more outcomes for the patient of interest are trending away from a standard for the prognosis or outcome based group.

In some embodiments, the method further comprises where it is determined that one or more outcomes for the patient of interest are trending away from the standard for the prognosis or outcome based group, sending an alert to a health care provider or health payer of the patient of interest including information regarding the one or more outcomes that are trending away from the standard.

In some embodiments, the method further comprises where the total cost of treatment of the patient over the clinically relevant period exceeds the expected cost for treatment of the patient of interest over the clinically relevant period by over a threshold amount, sending an alert to a health care provider or health payer of the patient of interest.

In some embodiments, the method further comprises after accessing or receiving the second set of data, iteratively accessing updated or new data sets comprising personal health information associated with the patient; and after accessing or receiving each updated or new data set: assigning, based on the accessed or new data set, updated attributes for at least some of the set of preselected variables and/or attributes for preselected variables that did not previously have an assigned attribute; and where attributes are assigned for at least the minimum subset of the treatment relevant variables and at least the minimum subset of the prognosis or outcome relevant variables, assigning a refined nodal address or an updated refined nodal address to the patient of interest based on current assigned attributes for the set of treatment-relevant variables and current assigned attributes for the set of prognosis or outcome relevant variables.

In some embodiments, the method further comprises receiving or accessing information regarding a change in the set of preselected variables including the addition of one or more variables to the set of treatment relevant variables and/or to the set of prognosis or outcome relevant variables; assigning an attribute for at least one of the one or more variables added to the set of treatment relevant variables and/or to the set of prognosis or outcome relevant variables based on current personal health information associated with the patient of interest; and assigning a different refined nodal address to the patient of interest based on the assigned attributes for the treatment relevant variables and the prognosis or outcome relevant variables. In some embodiments, the second data set includes data indicating a progression of the disease after the first point in time or after the first period of time. In some embodiments, the first data set includes information regarding a first diagnosis and the second data set includes information regarding an updated diagnosis after the first diagnosis. In some embodiments, the second data set includes information regarding attributes for which no information or incomplete information was provided in the first data set. In some embodiments, the prognosis-related expected outcome with respect to occurrence of a defined end point event includes one or more of overall survival, progression free survival, or disease free survival. In some embodiments, the predetermined treatment plan information includes information regarding one or more bundles of predetermined patient care services, wherein providing the predetermined treatment plan information to the health care provider of the patient of interest comprises providing information regarding the one or more bundles of predetermined patient care services. In some embodiments, where the predetermined treatment plan information associated with the provisional nodal address assigned to the patient of interest changes before a treatment decision has been made or before a refined nodal address has been assigned to the patient of interest, the method further comprises providing current predetermined treatment plan information to the health care provider of the patient of interest.

In some embodiments, the method further comprises providing an alert to health care provider of the patient of interest that the predetermined treatment plan information associated with the provisional nodal address assigned to the patient of interest has changed.

In some embodiments, the method further comprises generating the provisional nodal address based on the assigned attributes for the set of treatment-relevant variables prior to assigning the provisional nodal address to the patient of interest.

In some embodiments, the method further comprises generating the refined nodal address based on the assigned treatment relevant variables and on the assigned prognosis or outcome relevant variables prior to assigning the refined nodal address to the patient of interest.

In some embodiments, the method further comprises: assigning the patient of interest to a prognosis or outcome based group based on the refined nodal address assigned to the patient of interest; measuring a behavioral variance for each of a plurality of medical care providers for a plurality of patients assigned to the prognosis or outcome based group; and identifying necessary care absent and/or unnecessary care being provided contributing to the measured behavioral variance for at least one of the medical care providers.

According to another aspect, the described invention provides a system for facilitating early treatment decisions and determining a prognosis-related expected outcome with respect to occurrence of a defined end point event for a patient of interest diagnosed with a disease, the system comprising: a computing system hosting an application and in communication with a database and one or more third party systems executing the application, the computing system configured: to access or receive a first data set comprising personal health information associated with the patient of interest at a first time or over a first period of time, the personal health information including information regarding phenotypic characteristics; to assign, based on the accessed or received first set of data, attributes for at least some of a set of preselected variables, the set of preselected variables including a set of treatment relevant variables and a set of prognosis or outcome relevant variables; where attributes are assigned for at least a minimum subset of the set of treatment-relevant variables and less than a minimum subset of the prognosis or outcome relevant variables, to assign a provisional nodal address to the patient of interest based on the assigned attributes for the set of treatment relevant variables, the provisional nodal address being associated with predetermined treatment plan information for facilitation of treatment decisions, the predetermined treatment plan information tailored to a specific combination of attributes embodied in the provisional nodal address; to provide to at least one third party system of the one or more third party systems of a health care provider of the patient the predetermined treatment plan information; to access or receive a second set of data including updated or additional personal health information associated with the patient of interest at a second time or over a second period of time later than the first time or the first period of time; to assign, based on the accessed or received second set of data, updated attributes for at least some of the set of preselected variables and/or new attributes for preselected variables that did not previously have an assigned attribute; where attributes are assigned for at least the minimum subset of the treatment relevant variables and at least the minimum subset of the prognosis or outcome relevant variables; to assign a refined nodal address to the patient of interest based on the current assigned attributes for the set of treatment relevant variables and the current assigned attributes for the set of prognosis or outcome relevant variables; and determine the prognosis-related expected outcome with respect to occurrence of the defined end point event for the patient of interest based on the refined nodal address assigned to the patient of interest.

In one embodiment, the minimum subset of the treatment relevant variables is the treatment relevant variables in the set of preselected variables required to provide preselected treatment relevant information tailored to a patient's specific combination of treatment relevant attributes to guide a treatment decision. In some embodiments, the minimum subset of the treatment relevant variables for the patient of interest depends, at least in part, on a cancer type and a treatment intent for the patient of interest. In some embodiments, the minimum subset of the treatment relevant variables includes a cancer type, a cancer stage, and a treatment intent, wherein what other of the treatment relevant variables are included in the minimum subset of the treatment relevant variables depends, at least in part, on the cancer type and the treatment intent for the patient of interest. In some embodiments, accessing or receiving the first data set comprising personal health information associated with the patient of interest at a first time or over a first period of time comprises accessing or receiving information regarding a cancer type and a treatment intent for the patient of interest; wherein the computing system is further configured to determine the minimum subset of the treatment relevant variables based on received information regarding the cancer type and the treatment intent for the patient of interest.

In some embodiments, the computing system is further configured to present to the patient and/or a health care provider for the patient a user interface for entry of data in the first data set. In some embodiments, the user interface guides the user in entry of at least the minimum subset of treatment relevant variables.

In some embodiments, the computing system is further configured to present to the patient and/or a health care provider for the patient a user interface for entry of data in the first data set; and to receive information regarding the cancer type of the patient of interest and the treatment intent for the patient of interest; and after the determination of the minimum subset of the treatment relevant variables based on the received information regarding the cancer type of the patient of interest and the treatment intent for the patient of interest, to guide entry of the rest of the minimum subset of the treatment relevant variables via the user interface. In some embodiments, the minimum subset of the prognosis or outcome relevant variables is all of the prognosis or outcome relevant variables in the set of preselected variables required for statistical analysis of prior outcomes. In some embodiments, the second set of data includes data obtained from health records of the patient of interest. In some embodiments, assigning, based on the accessed second set of data, updated attributes for at least some of the set of preselected variables and/or new attributes for preselected variables that did not previously have an assigned attribute comprises verifying and/or correcting detected issues in the second set of data to determine the updated or new attributes. In some embodiments, the first set of data includes data obtained from health records of the patient of interest.

In some embodiments, the computing system is further configured to assign the attributes for at least some of the set of preselected variables. In some embodiments, the prognosis-related expected outcome for the patient of interest is determined from a statistical analysis of prior prognosis-related outcomes for patients in a prognosis or outcome based group of patients who each were assigned the same refined nodal address as that assigned to the patient of interest at a corresponding point in treatment and disease progression as that of the patient of interest.

In some embodiments, the computing system is further configured to statistically analyze the prior outcomes for patients in the prognosis or outcome based group of patients to determine a current expected prognosis-related outcome for the patient of interest. In some embodiments, the current expected prognosis-related outcome is time to progression from start of second line therapy to start of third line therapy, and wherein the patients in the prognosis or outcome based group of patients are patients who were each assigned the same refined nodal address as that assigned to the patient of interest at the start of second line therapy.

In some embodiments, the computing system is further configured to conduct an updated statistical analysis of the prior outcomes for patients in the prognosis or outcome based group of patients to determine an updated current expected prognosis-related outcome and store information regarding the updated current expected prognosis-related outcome.

In some embodiments, the computing system is configured to conduct the updated statistical analysis periodically.

In some embodiments, the prognosis-related expected outcome for the patient of interest is determined from a statistical analysis of prior prognosis-related outcomes for patients in a prognosis or outcome based group of patients at least some of whom were assigned the same refined nodal address as that assigned to the patient of interest at a corresponding point in treatment and disease progression as that of the patient of interest.

In some embodiments, the computing system is further configured to transmit information regarding the prognosis-related expected outcome to a client device associated with a health care provider of the patient or a payer for health care of the patient of interest.

In some embodiments, the computing system is further configured: to access information regarding an outcome for the patient of interest; to compare the outcome for the patient of interest to the determined prognosis-related expected outcome for the patient of interest; and to transmit information regarding the comparison to a health care provider for the patient or to a health care payer for the patient of interest.

In some embodiments, the computing system is further configured to determine an expected cost of treatment of the patient of interest for the disease over a clinically relevant period based on cost of treatment for all patients assigned to a prognosis or outcome based group of patients who each were assigned the same refined nodal address as that assigned to the patient of interest at a corresponding point in treatment and disease progression as that of the patient of interest. In some embodiments, the refined nodal address assigned to the patient of interest has an associated expected cost of treatment for the disease from diagnosis to death or cure, the associated expected cost of treatment determined by statistically analyzing prior cost of treatment from diagnosis to death or cure for patients in the a prognosis or outcome based group of patients who were each assigned the same refined nodal address as that assigned to the patient of interest at diagnosis.

In some embodiments, the computing system is further configured to access information regarding billed costs for treatment of the patient of interest and to determine a total cost for treatment of the patient of interest over the clinically relevant period; and to compare the expected cost for treatment of the patient of interest over a clinically relevant period with the total cost for treatment of the patient of interest over the clinically relevant period. In some embodiments, the clinically relevant period is from diagnosis to death or cure.

In some embodiments, the computing system is further configured to compare one or more outcomes for the patient of interest to one or more historical outcomes for patients in a prognosis or outcome based group who were each assigned the same refined nodal address as that assigned to the patient of interest at diagnosis or at progression to determine if the one or more outcomes for the patient of interest are trending away from a standard for the prognosis or outcome based group.

In some embodiments, the computing system is further configured to determine whether one or more outcomes for the patient of interest are trending away from the standard for the prognosis or outcome based group, and where it is determined that the one or more outcomes for the patient of interest are trending away from the standard, to send an alert to a health care provider or health payer of the patient of interest including information regarding the one or more outcomes that are trending away from the standard.

In some embodiments, the computing system is further configured to determine whether the total cost of treatment of the patient over the clinically relevant period exceeds the expected cost for treatment of the patient over the clinically relevant period by over a threshold amount, and where the total cost of treatment exceeds the expected cost of treatment, to send an alert to a health care provider or health payer of the patient of interest.

In some embodiments, the computing system is further configured, after accessing or receiving the second set of data, to iteratively access or receive updated or new data sets comprising personal health information associated with the patient; and after accessing or receiving each updated or new data set: to assign, based on the accessed or new data set, updated attributes for at least some of the set of preselected variables and/or attributes for preselected variables that did not previously have an assigned attribute; and where attributes are assigned for at least the minimum subset of the treatment relevant variables and at least the minimum subset of the prognosis or outcome relevant variables, to assign a refined nodal address or an updated refined nodal address to the patient of interest based on current assigned attributes for the set of treatment-relevant variables and current assigned attributes for the set of prognosis or outcome relevant variables.

In some embodiments, the computing system is further configured to receive or access information regarding a change in the set of preselected variables including the addition of one or more variables to the set of treatment relevant variables and/or to the set of prognosis or outcome relevant variables; to assign an attribute for at least one of the one or more variables added to the set of treatment relevant variables and/or to the set of prognosis or outcome relevant variables based on current personal health information associated with the patient of interest; and to assign different refined nodal address to the patient of interest based on the assigned attributes for the treatment relevant variables and the prognosis or outcome relevant variables. In some embodiments, the second data set includes data indicating a progression of the disease after the first point in time or after the first period of time. In some embodiments, the first data set includes information regarding a first diagnosis and the second data set includes information regarding an updated diagnosis after the first diagnosis. In some embodiments, the second data set includes information regarding attributes for which no information or incomplete information was provided in the first data set. In some embodiments, the prognosis-related expected outcome with respect to occurrence of a defined end point event includes one or more of overall survival, progression free survival, or disease free survival. In some embodiments, the predetermined treatment plan information includes information regarding one or more bundles of predetermined patient care services, wherein providing the predetermined treatment plan information to the health care provider of the patient of interest comprises providing information regarding the one or more bundles of predetermined patient care services.

In some embodiments, before a treatment decision has been made or before a refined nodal address has been assigned to the patient of interest, where the predetermined treatment plan information associated with the provisional nodal address of the patient of interest changes, the computing system is further configured to provide current predetermined treatment plan information to the health care provider of the patient of interest.

In some embodiments, the computing system is further configured to provide an alert to health care provider of the patient of interest that the predetermined treatment plan information associated with the provisional nodal address assigned to the patient of interest has changed.

In some embodiments, the computing system is further configured to generate the provisional nodal address based on the assigned attributes for the set of treatment-relevant variables prior to assigning the provisional nodal address to the patient of interest.

In some embodiments, the computing system is further configured to generate the refined nodal address based on the assigned treatment relevant variables and on the assigned prognosis or outcome relevant variables prior to assigning the refined nodal address to the patient of interest.

In some embodiments, the computing system is further configured to assign the patient of interest to a prognosis or outcome based group based on the refined nodal address assigned to the patient of interest; to measure a behavioral variance for each of a plurality of medical care providers for a plurality of patients assigned to the prognosis or outcome based group; and to identify necessary care absent and/or unnecessary care being provided contributing to the measured behavioral variance for at least one of the medical care providers.

According to another aspect, the described invention provides a non-transitory computer readable medium comprising program instructions for facilitating early treatment decisions and determining a prognosis-related expected outcome with respect to occurrence of a defined end point event for a patient of interest diagnosed with a disease, wherein execution of the program instructions by one or more processors causes the one or more processors to perform the method of any one of the claims.

BRIEF DESCRIPTION OF THE DRAWINGS

The drawings are intended to illustrate the teachings described herein and are not intended to show relative sizes and dimensions, or to limit the scope of examples or embodiments. In the drawings, the same numbers are used throughout the drawings to reference like features and components of like function.

DESCRIPTION OF EMBODIMENTS

Figure 1:
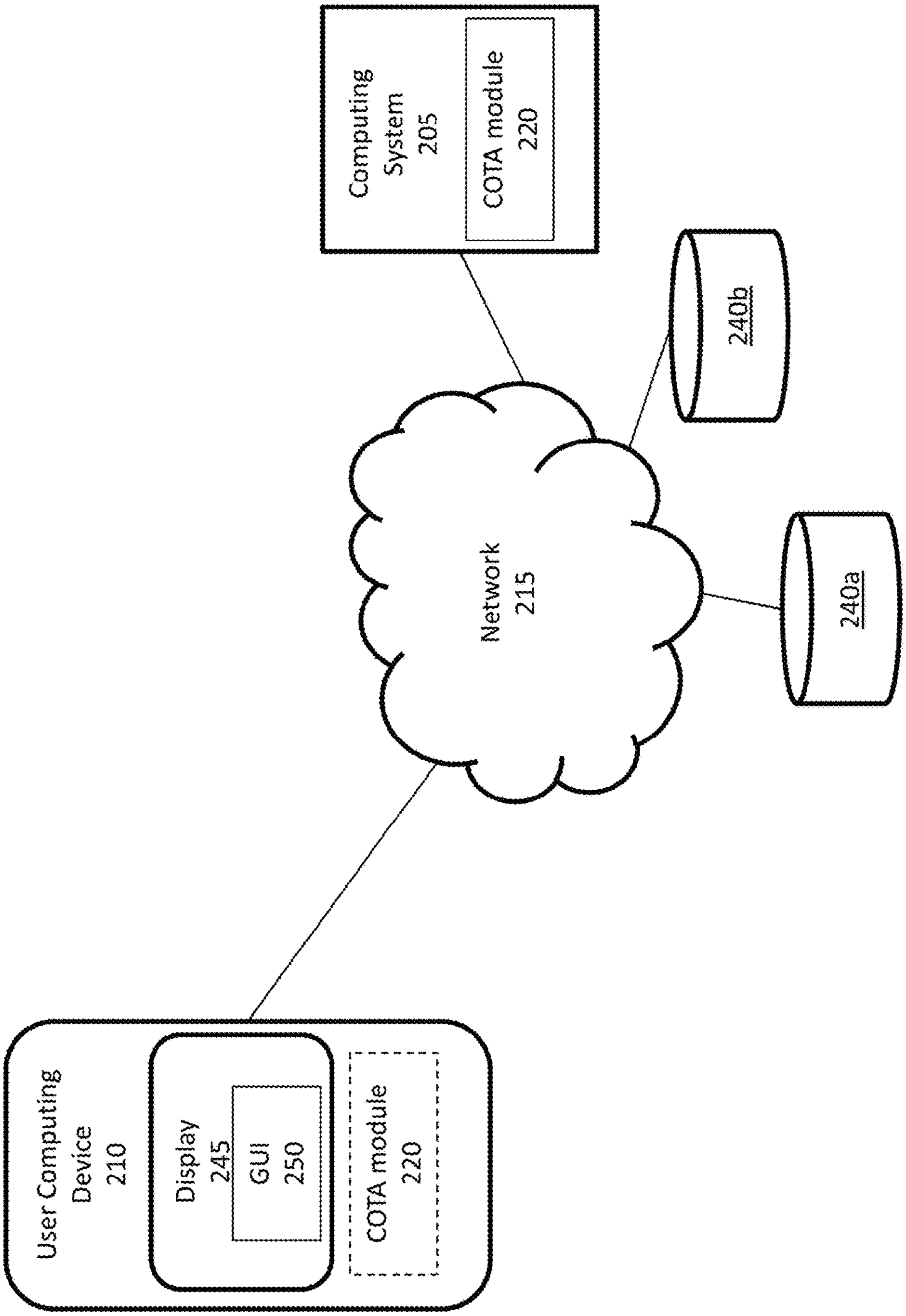
FIG. 1 schematically depicts a network diagram for providing a clinical outcome tracking and analysis (COTA) module to a user computing device in accordance with some embodiments of the present disclosure.

Embodiments are now discussed in more detail referring to the drawings that accompany the present application. In the accompanying drawings, like and/or corresponding elements are referred to by like reference numbers.

Described herein are a system, method, and non-transitory computer-readable medium that employ a provisional nodal address assigned to a patient of interest to assist health care providers in providing treatment plan information to guide treatment decisions for the patient of interest, and employ one or more refined nodal addresses that can each be used in determining an expected outcome for the patient of interest. In some embodiments, the refined nodal addresses can be used to assist payers in making payment decisions based on expected outcome, adjusted for risk. In some embodiments, the system, method and non-transitory computer-readable medium generate and assign provisional nodal addresses, and generate, assign, and update refined nodal addresses for patients. In some embodiments, the methods and systems consolidate information necessary for health care providers to make early treatment decisions based on an initial provisional nodal address associated with the patient of interest. In some embodiments, the systems and methods consolidate information necessary to make treatment decisions and information that is relevant to the patient's expected prognosis-related outcome in a refined nodal address and determine an expected prognosis-related outcome for the patient. In some embodiments, the systems and methods consolidate information regarding historical costs for a population of patients and determine cost to risk adjusted expected outcomes regarding payment decisions for insurance providers. Additionally, in some embodiments, the systems and methods update (e.g., automatically update, or periodically update) the refined nodal addresses based on the most current information available to the system. In this regard, the systems and methods increase operational efficiency as compared with conventional systems and, unlike conventional systems, reduce the need for repetitive querying and information retrieval from various different systems to determine treatment and payment decisions.

Embodiments described herein beneficially provide at least two different types of functionality in one integrated method or system. The provisional nodal addresses employed in methods and systems described herein facilitate early treatment decisions for a patient. For example, in some embodiments, the provisional nodal address assigned to a patient is associated with predetermined treatment plan information specific to the combination of treatment relevant attributes or parameters represented by the provisional nodal address. As used herein, the term "attributes" refers to values of predetermined variables, combinations of which are used to determine a refined nodal address and/or a provisional nodal address. The treatment plan information may include information regarding treatment plans and/or treatment strategies specific to all of the treatment relevant variables or attributes of the patient, as described below. In some embodiments, the treatment plan information includes information regarding one or more bundles of predetermined patient care services. For example, in some embodiments, the predetermined treatment plan information may be information regarding one or more bundles of predetermined patient care services. The bundles of predetermined patient care services may include a recommended course of treatment tailored to the patient's specific attributes for treatment relevant variables or parameters. In some embodiments, the predetermined treatment plan information associated with the provisional nodal address assigned to the patient is provided to a healthcare provider of the patient or a healthcare payer of the patient. Further, in some embodiments, as additional or updated information relevant to treatment of the patient is received prior to assigning a refined nodal address to the patient and prior to a treatment decision being made for the patient, the provisional nodal address is updated or changed as needed based on the additional or updated information relevant to treatment. If the updated or changed nodal address is associated with different treatment-related information, such as a different bundle of predetermined patient care services, information regarding the different treatment-related information, such as information regarding the different bundle of predetermined patient care services, is provided to a healthcare provider of the patient or to a payer for healthcare of the patient. In some embodiments, the provisional nodal address is only employed for guiding early or initial treatment decisions (e.g., within a short period of time after diagnosis) when a refined nodal address has not yet been assigned, and a refined nodal address later assigned to the patient is used for guiding treatment decisions after assignment of the refined nodal address.

In some embodiments, the provisional nodal address is assigned within 2 days of diagnosis, within 3 days of diagnosis, within 4 days of diagnosis, within 5 days of diagnosis, within 6 days of diagnosis, within 7 days of diagnosis, within 8 days of diagnosis, within 9 days of diagnosis, within 10 days of diagnosis, within 11 days of diagnosis, within 12 days of diagnosis, or within 13 days of diagnosis. In some embodiments, the refined nodal address is assigned within 14 days of diagnosis, within 18, days of diagnosis, within 22 days of diagnosis, within 26 days of diagnosis, within 30 days of diagnosis, within 34 days of diagnosis, within 38 days of diagnosis or more.

In some embodiments, initial data regarding a patient will be accessed by, received by, or provided to the system or for the method at or shortly after diagnosis of the patient (e.g., within 2 days of diagnosis, within 3 days of diagnosis, within 4 days of diagnosis, within 5 days of diagnosis, within 6 days of diagnosis, within 7 days of diagnosis, within 8 days of diagnosis, within 9 days of diagnosis, within 10 days of diagnosis, within 11 days of diagnosis, within 12 days of diagnosis, or within 13 days of diagnosis). At the time at which a provisional nodal address is assigned, the patient data provided, received, or accessed may include sufficient information to determine or guide determination of a recommended course of treatment for the patient, but insufficient information to provide a prognosis-related expected outcome with respect to occurrence of a defined end point event (e.g., overall survival, progression free survival, or disease free survival) for the patient. Instead of waiting to receive information relevant to the prognosis-related expected outcome, but not relevant to early treatment recommendations, before assigning the patient a nodal address for determining a recommended course of treatment, assigning a provisional nodal address that only incorporates treatment relevant information to the patient enables the system or method to assist health care providers or health care payers in guiding treatment decisions for the patient, especially early in the disease process after diagnosis. In some embodiments, a first set of data including personal health information regarding the patient that is used to assign the provisional nodal address is obtained via a user interface from the patent, from a health care provider for the patient, or both. The user interface may be configured to guide the patient or the health care provider in providing information regarding at least a minimum set of treatment relevant variables for assignment of the provisional nodal address. This may enable rapid or on demand assignment of the provisional nodal address and rapid access to treatment information associated with the provisional nodal address. In some embodiments, at least some of the variables included in the minimum set of treatment relevant variables for assignment of the provisional nodal address may depend on values of some of the treatment relevant variables for the patient (e.g., cancer type and treatment intent). In some embodiments, the first set of data includes data obtained from health records of the patient.

Additional functionality is provided by the system or method through the use of refined nodal addresses. In some embodiments, after additional information regarding the patient is accessed or received that includes at least a minimum amount of information relevant to a prognosis-related expected outcome, the patient is assigned a refined nodal address that is used to determine a prognosis-related expected outcome for the patient. In some embodiments, the refined nodal address is used for determining a risk adjusted expected outcome for the patient. In some embodiments, a provisional nodal address is assigned to a patient at or shortly after diagnosis even if the system or method receives or accesses sufficient initial information to assign a refined nodal address, and the provisional nodal address is used to guide treatment decisions. In other embodiments, if the initial information provided is sufficient to assign a refined nodal address to the patient, a refined nodal address is assigned to the patient and only the portion of the refined nodal address including the treatment relevant variables is used for providing predetermined treatment plan information (e.g., information regarding one or more bundles of predetermined patient care services) to the healthcare provider of the patient or to the payer for healthcare of the patient.

In some embodiments, a refined nodal address assigned to the patient of interest is associated with a prognosis or outcome based group of patients. In some embodiments, the prognosis-related expected outcome for the patient of interest is determined by statistically analyzing prior prognosis-related outcomes for patients in the outcome based or prognosis based group. In some embodiments, the prognosis or outcome based group of patients includes patients who were or are assigned the same refined nodal address as that assigned to the patient of interest at the corresponding point in each patient's disease progression (e.g., progression through cancer) as that of the patient of interest. In some embodiments, only one refined nodal address is associated with a prognosis or outcome based group of patients. For example, in some embodiments, each patient in the prognosis or outcome based group of patients for determining a prognosis-related expected outcome for the patient of interest is or was assigned the same specific refined nodal address as that of the patient of interest at a corresponding point in treatment and disease progression as that of the patient of interest. In other embodiments, more than one refined nodal address is associated with the same prognosis or outcome based group of patients for determining a prognosis-related expected outcome for the patient of interest. For example, where the number of prior patients assigned a refined nodal address is relatively small, the small number of patients significantly impacting the reliability of a statistical analysis based only on prior patients assigned the particular refined nodal address, patients who were assigned to multiple refined nodal addresses having differences in variables that less relevant to prognosis or outcome may be combined into one prognosis or outcome based group of patients for analysis.

In some embodiments, a statistical analysis of historical costs for patients in the outcome based or prognosis based group associated with the refined nodal address assigned to the patient of interest is used to determine expected costs for treatment of the patient over a period of treatment. In some embodiments, insufficient numbers of prior patients may have been assigned a single refined nodal address to conduct a treatment-based statistical analysis of patients assigned the single refined nodal address. In such embodiments, a treatment-based statistical analysis of prior patients who have the same attributes for variables used in the provisional nodal address, or who were assigned the same provisional nodal address, may enable the statistical analysis to be conducted, as patients assigned different refined nodal addresses may have common treatment relevant variables and attributes and/or may have been assigned the same provisional nodal address. In some embodiments, a treatment-based statistical analysis can be conducted based on a treatment-based group that is associated with multiple refined nodal addresses, where the variables whose attributes differ in the multiple refined nodal addresses are not relevant to treatment or are less relevant to treatment.

The present application describes assigning a provisional nodal address or a refined nodal address to a patient of interest based on attributes assigned to preselected variables from personal health information associated with the patient of interest. This may also be described as assigning the patient to a provisional nodal address or to a refined nodal address. In some embodiments, this may also be described as assigning a provisional nodal address or a refined nodal address to the personal health information associated with the patient of interest.

Various embodiments are disclosed herein; however, it is to be understood that the disclosed embodiments and user interfaces shown are merely illustrative of the disclosure that can be embodied in various forms. In addition, each of the examples given in connection with the various embodiments is intended to be illustrative, and not restrictive. Further, the figures are not necessarily to scale, some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

Embodiments are described below with reference to block diagrams and operational illustrations of methods and systems. It is understood that each block of the block diagrams or operational illustrations, and combinations of blocks in the block diagrams or operational illustrations, can be implemented by means of analog or digital hardware and computer program instructions. These computer program instructions can be provided to one or more processors of a general purpose computer, special purpose computer, ASIC, or other programmable data processing apparatus or multiple programmable data processing apparatuses, such that the instructions, which execute via one or more processors of the computer or other programmable data processing apparatus(es), implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Although described with respect to cancer conditions, the described clinical outcome therapeutic analysis can be used for any clinical condition, e.g., cardiovascular disease, metabolic disease (diabetes), immune mediated diseases (e.g., lupus, rheumatoid arthritis), organ transplantation; neurodegenerative disorders; pulmonary diseases, infectious diseases, and hepatic disorders. A practitioner would know the parameters of each such condition. In some embodiments, the methods and systems are specific to cancer conditions.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

As used herein, a patient of interest refers to the patient whose personal health information is accessed or received, and who is assigned a provisional and/or a refined nodal address or is assigned to a provisional and/or a refined nodal address. The phrase "of interest" is merely used to differentiate this patient from other patients who may be included in a prognosis or outcome based group of patients (e.g., for determining a prognosis-related expected outcome for the patient of interest).

FIG. 1 schematically depicts a network diagram of computing systems, devices, networks and databases that could be employed in connection with embodiments described herein. The depicted network diagram shows a computing system 205 (also referred to below as server 205) communicating with a user computing device (also referred to herein as client device) 210 over network 215 to provide a clinical outcome tracking and analysis (COTA) module 220 to the user computing device 210 in accordance with one embodiment. The computing system 205 may generate and/or serve content such as web pages, for example, to be displayed by a browser (not shown) of user computing device 210 over network 215 such as the Internet. In one embodiment, the COTA module 220 is a web page (or is part of a web page) and is accessed by a user of the user computing device 210 via a web browser. In another embodiment, the COTA module 220 is a software application, for example, software installed on the user computing device or a mobile "app", that can be downloaded to the user computing device 210 from the computing system 205 or from a third party computing system. In a further embodiment, the COTA module 220 provides a graphical user interface for enabling the functionality described herein, when executed on the user computing device 210. As an example, the computing system 205 can host the COTA module 220 and the user computing device 210 can execute an instance of the COTA module. The COTA module 220 can be a web-based application or non-web-based application. In some embodiments, the user computing device is a computing device of a healthcare provider, of a healthcare system, of a healthcare payment system, or of a patient. In some embodiments, different aspects of the COTA module 220 may execute on multiple different user computing devices that all may be associated with one entity, such as with the healthcare provider, or that may be associated with different entities, such as a client device associated with the patient and another client device associated with the healthcare provider.

A computing device embodied fully or in part as computing system 205 and/or user computing device 210 may be capable of sending or receiving signals, such as via a wired or wireless network, or may be capable of processing or storing signals, such as in memory as physical memory states. Devices and systems capable of operating as computing system 205 include, but are not limited to, as examples, dedicated rack-mounted servers, desktop computers, laptop computers, set top boxes, integrated devices combining various features, such as two or more features of the foregoing devices, or the like. Embodiments of computing system 205 may vary widely in configuration or capabilities, but generally may include one or more central processing units and memory. Computing system 205 may also include one or more mass storage devices, one or more power supplies, one or more wired or wireless network interfaces, one or more input/output interfaces, or one or more operating systems, such as Windows® Server, Mac® OS X®, Unix®, Linux®, FreeBSD®, or the like. Computing system 205 may include multiple different computing devices. Computing system 205 may include multiple computing devices that are networked with each other. Computing system 205 may include networks of processors or may employ networks of remote processors for processing (e.g., cloud computing).

The computing system 205 may include a device that includes a configuration to provide content via a network to another device. The computing system 205 may further provide a variety of services that include, but are not limited to, web services, third-party services, audio services, video services, email services, instant messaging (IM) services, SMS services, MMS services, FTP services, voice over IP (VOIP) services, calendaring services, photo services, or the like. Examples of content may include text, images, audio, video, or the like, which may be processed in the form of physical signals, such as electrical signals, for example, or may be stored in memory, as physical states, for example. Examples of devices that may operate as or be included in computing system 205 include desktop computers, multiprocessor systems, microprocessor-type or programmable consumer electronics, etc.

In one embodiment, the computing system 205 hosts or is in communication with one or more databases 240*a*, 240*b*. The database(s) 240*a*, 240*b* may be stored locally or remotely from the computing system 205. In one embodiment, the COTA module 220 accesses or searches or sorts the data stored in one or more of the database(s) 240*a*, 240*b*. The COTA module 220 may also retrieve information over network 215 (e.g., from the Internet). Databases 240*a*, 240*b* may individually or collectively store patient data or other pertinent medical information. For example, other pertinent medical information stored in the database or retrieved by the COTA module can include information related to the definition of or identification of preselected variables relevant for treatment or prognosis of a disease or disorder. In some embodiments, the information related to the identification of preselected variables relevant for treatment or prognosis of a disease or disorder may be based on information from experts in their respective fields (e.g., oncologists with more than 5, 10, 15, 20, 30, etc. years of experience). In some embodiments, data is entered into database(s) 240*a*, 240*b* and/or the COTA module 220 manually, automatically, or both. The database(s) 240*a*, 240*b* individually or collectively can be configured to store one or more of personal health information (PHI) associated with each patient in a group of patients, preselected variables, attributes for the preselected variables, bundles of predetermined patient care services, diagnosis information, provisional nodal addresses, refined nodal addresses, and prognosis or outcome based group information. In some embodiments, the one or more databases 240*a*, 240*b* can include multiple different databases. The multiple different databases can store different subsets of the information, different types of information, information from different health providers, information from different types of systems, or any other division of the information. In some embodiments, database(s) 240*a*, 240*b* are stored across multiple different storages. In some embodiments, databases 240*a*, 240*b* are stored in one or more storages that are remote from each other. The multiple different databases or storages can each be accessed by and/or provide information to the COTA module 220, either directly or indirectly.

A network may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

A wireless network may couple client devices with a network 215. A wireless network 215 may employ stand-alone ad-hoc networks, mesh networks, Wireless LAN (WLAN) networks, cellular networks, or the like. A wireless network 215 may further include a system of terminals, gateways, routers, or the like coupled by wireless radio links, or the like, which may move freely, randomly or organize themselves arbitrarily, such that network topology may change, at times even rapidly. A wireless network 215 may further employ a plurality of network access technologies, including Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network 215 may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

In one embodiment, a user computing device 210 is a computer. In one embodiment, the user computing device 210 is a terminal for a computer system. In one embodiment, the user computing device 210 is a tablet. In one embodiment, the user computing device 210 is a smartphone. The user computing device 210 can be any other suitable computing device or computing system.

In one embodiment, some or all of the COTA module 220 may be implemented in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs). Example embodiments may be implemented in digital electronic circuitry, or in computer hardware, firmware, software, or in combinations of them. Example embodiments may be implemented using at least one computer program product, for example, a computer program tangibly embodied in an information carrier, for example, in a machine-readable medium for execution by, or to control the operation of, data processing apparatus, for example, a programmable processor, a computer, or multiple computers.

In some embodiments, the COTA module 220 enables effective management of patient care, resulting in better clinical outcomes at controlled costs. In one embodiment, the COTA module 220 is a connector or interface between third parties and medical professionals (e.g., oncologists) including medical providers. In one embodiment, the COTA module 220 is an analytic tool that is configured to sort cancers and cancer patients to the highest level of clinical and molecular fidelity relevant to treatment decisions and relevant to prognosis-related predicted outcomes. In some embodiments, the COTA module 220 tracks outcomes, such as overall survival (OS) (meaning the length of time from either the date of diagnosis or the start of treatment for a disease, such as cancer, that patients diagnosed with the disease are still alive, for which the end-point event is death from any cause), Progression free survival (PFS) (meaning the length of time during and after the treatment of a disease, such as cancer, that a patient lives with the disease but it does not get worse, and which uses progression of a disease as an end-point, e.g., tumor growth or spread), disease-free survival (in cancer, meaning the length of time after primary treatment for a cancer ends that the patient survives without any signs or symptoms of that cancer, for which the end point event is relapse) and cost, in real-time. In some embodiments, methods and systems generate and assign provisional nodal addresses, and generate, assign, and update refined nodal addresses to assist healthcare providers in making treatment decisions, including early treatment decisions immediately after diagnosis, and to assist healthcare providers and/or healthcare payers by providing information regarding expected prognosis-related outcome specific to the patient. In some embodiments, the expected prognosis-related outcome can be used for outcome adjusted risk analysis in making decisions regarding payment for treatment.

As noted above, the user computing device 210, or one of multiple computing devices 210, can be operated by any of patients, health care provider systems, payers (e.g., insurance companies), and medical professionals in various embodiments. The patients, health care provider systems, medical professionals, or insurance company can execute an instance of the COTA module 220 on the user computing device 210 to interface with the computing system 205. The COTA module 220 can render a GUI 250 on the display 245. It can be appreciated, that, in some embodiments, the GUI 250 can be different for each type of user. For example, in some embodiments, patients, health care provider systems, medical professionals, or insurance companies may each be presented a different GUI 250. In some embodiments, some aspects of the system or method may be executed on a user computing device 210 associated with a health care provider, and other aspects of the system or method may be executed on a user computing device 210 associated with a patient or with a health care payer.

In one embodiment, the COTA module 220 can alert the user of the user computing device 210 (e.g., medical professional, health care provider, health care system, health care payer) at key moments to provide relevant information. In some embodiments, the COTA module 220 can also enable communication and collaboration between medical professionals, health care systems, health care payer systems, as well as content publishing (e.g., by medical professionals or health care systems). In one embodiment, COTA module 220 can enable medical professionals to execute at-risk contracts (e.g., bundled payments) with payers.

Although the COTA module 220, systems and methods, are described herein with respect to cancer, the COTA module 220, systems and methods, can be utilized advantageously to manage any disease or condition as explained above.

Figure 2:
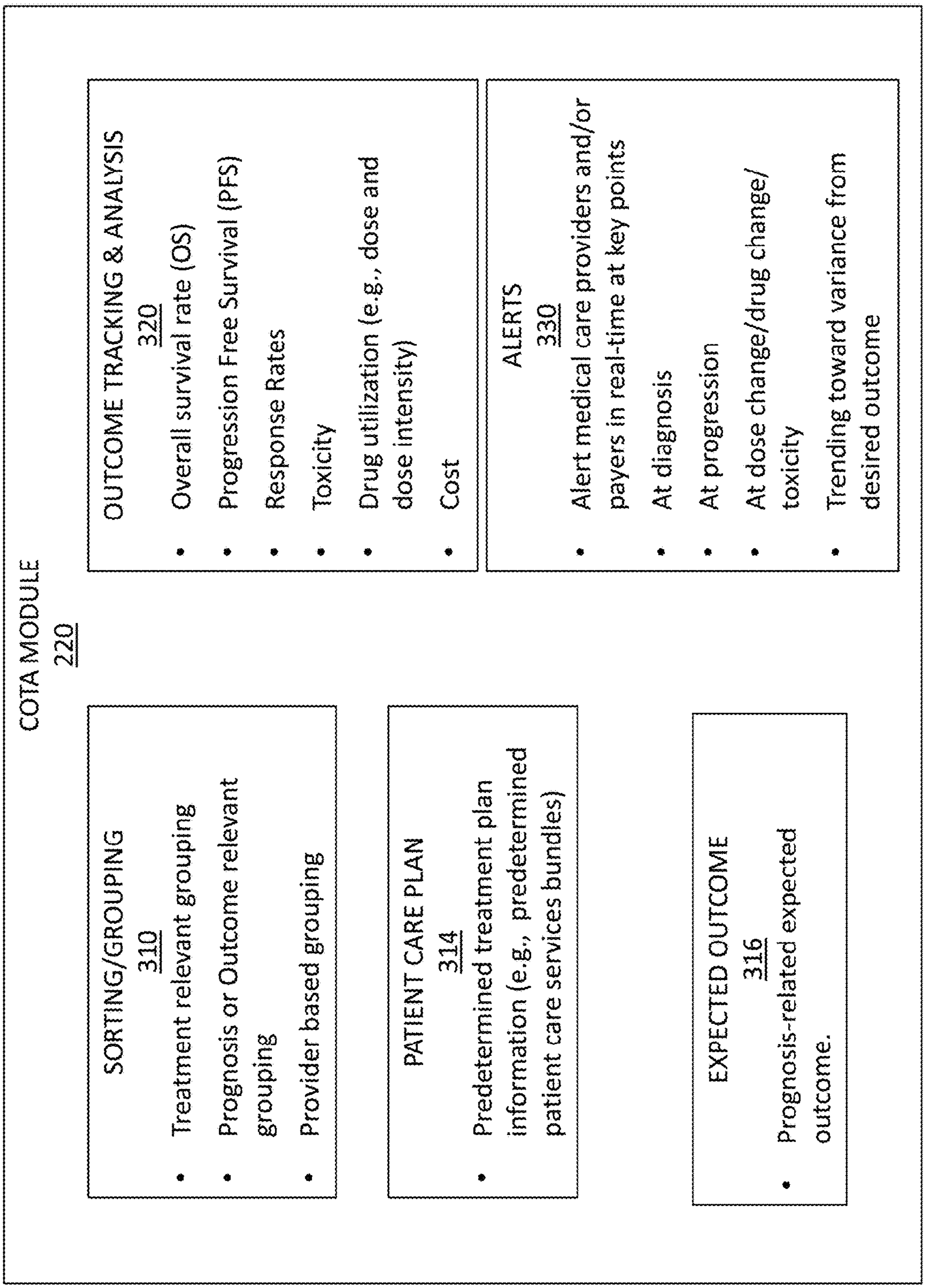
FIG. 2 schematically depicts some functions provided by the COTA module in accordance with some embodiments of the present disclosure.

FIG. 2 is a block diagram illustrating some functions 300 provided by the COTA module 220, in accordance with one embodiment. In one embodiment, the COTA module 220 performs sorting/grouping 310, which sorts, groups, and/or identifies patients satisfying one or more parameters. The parameters may be parameters relevant to determining a course of treatment for a patient, parameters relevant to an expected or actual outcome for the patient, parameters relating to a treatment provided to the patient, parameters relevant to a health care provider or a health care payer for a patient, or other potentially relevant parameters. Parameters may include, for example, demographic parameters, e.g., sex, age, ethnicity, comorbidities, tobacco use, medical record number, source of insurance, primary care medical professional, referring medical professional, hospital, approved service vendors (e.g., pharmacy), disease specific clinical and molecular phenotype, therapy intent, stage of therapy with respect to progression of disease, and biomarkers. The parameters may be a simple indicator (e.g., positive, negative, not accessed), a numerically based parameter (e.g., tumor size), a standards based parameter (e.g., tumor grade), etc. In some embodiments, the parameters may be received by the COTA module 220 as a user selected input. In some embodiments, the user may be a health care provider for a patient or patients, a medical professional treating a patient or patients, a health care provider system for a patient or patients, a payer for health care services for a patient or patients, or a patient. In some embodiments, the parameters for grouping or sorting may be received or accessed by the COTA module 220 in a manner other than a user selected input (e.g., automatically or periodically based on a query from another system, or based on information stored in a database). In some embodiments, a user selected input may identify a patient and the sorting, grouping, or identification identifies a group of patients having the same treatment relevant parameters as the identified patient (e.g., a treatment based group of patients). In some embodiments, the COTA module 220 may provide individual/and or collective information regarding patients in the group of patients having the same treatment relevant parameters as the identified patient without providing any personally identifiable information regarding patients in the group. In some embodiments, a user selected input may identify a patient (e.g. a patient of interest) and the sorting, grouping, or identification identifies a group of patients having the same prognosis or outcome relevant parameters as the identified patient (e.g., a prognosis or outcome based group of patients). In some embodiments, the COTA module 220 may provide individual/and or collective information regarding patients in the group of patients having the same prognosis or outcome parameters as the identified patient without providing any personally identifiable information regarding patients in the group. In some embodiments, the sorting or grouping is based, at least in part, on a provisional nodal address assigned to the identified patient or patient of interest, as explained in further detail below. In some embodiments, the sorting or groups is based, at least in part, on a refined nodal address that is assigned to or was assigned to identified patient or patient of interest at some point in disease progression, as explained in further detail below. In some embodiments, the sorting or grouping may be based, at least in part, on the provisional nodal address or the refined nodal address that is or was assigned to the identified patient or patient of interest at some point in disease progression.

In some embodiments, methods and systems may sort patients to the highest level of clinical and/or molecular fidelity using a sorting or grouping functionality 310 of the COTA module 220 because each patient has different mortality, morbidity, treatments and costs associated with expected outcomes. The term "highest level of clinical and/or molecular fidelity" refers to the highest level of patient information available according to the latest scientific and/or medical guidelines as accepted in its pertinent field. For example, where there are, e.g., 10 tests available for lung cancer, results of the 10 tests represent the highest level of clinical and/or molecular fidelity for lung cancer. The COTA module 220 may sort patients with lung cancer with any combination of those 10 results. The COTA module 220 may include additional scientific and/or medical guidelines as they become accepted in the pertinent field. In one embodiment, the COTA module 220 collects all information that impacts survival and/or prognosis and/or treatment of a patient based on the latest scientific and/or medical guidelines. In some embodiments, the sorting is conducted using a provisional nodal address or a refined nodal address as described below. In some embodiments, at the time of diagnosis, some information relevant to prognosis or outcome may not be known, but patients may still be sorted to the highest level of clinical and/or molecular fidelity for parameters or variables relevant to early treatment decisions using the provisional nodal address using the sorting or grouping functionality 310 of the COTA module 220. In some embodiments, at the time of diagnosis or shortly after diagnosis, some information relevant to treatment on a longer time scale and relevant to prognosis or outcome may not be available. Although this information may be relevant to some treatment decisions, guidance for early treatment decisions should not be held up waiting for this information to become available. In some embodiments, the provisional nodal address enables patients to be sorted or matched to guidance for recommended treatment based on information regarding a minimum subset of treatment relevant variables using the sorting or grouping functionality 310. In some embodiments, a refined nodal address enables patients to be sorted using the sorting or grouping functionality 310, and analyzed using an expected outcome functionality 160 of the COTA module with respect to information including a minimum subset of prognosis and outcome relevant variables. In some embodiments, a variable may be both a treatment relevant variable and a prognosis and outcome relevant variable.

In some embodiments, a provisional nodal address is assigned to a patient at or shortly after diagnosis, and a refined nodal address is assigned to a patient after diagnosis and, at least, at each subsequent identified disease progression. Thus, different refined nodal addresses may be assigned to a patient over time (e.g., as a disease progresses, as treatment intent changes, etc.). During analysis, the relevant nodal address for the patient of interest depends on the particular goal of the analysis. For example, if interested in an expected time for the patient of interest to progress from start of second line therapy to start of the third line therapy, the relevant refined nodal address would be the refined nodal address of the patient of interest at the start of second line therapy. Similarly, for an outcome or prognosis based group of patients whose historical data would be analyzed to address this question, in some embodiments, each patient in the outcome or prognosis based group of patients would have had the same refined nodal address as that of the patient of interest at the start of that patient's second line therapy.

In some embodiments, the COTA module provides patient care plan information 314 specific to all the treatment relevant attributes or variables of a patent. In some embodiments, the patient care plan information is predetermined treatment plan information specific to the combination of treatment relevant attributes or parameters represented by the provisional nodal address. The predetermined treatment plan information may include information regarding treatment plans and/or treatment strategies specific to all of the treatment relevant variables or attributes of the patient, or at least the minimum subset of the treatment relevant attributes, as described below. In some embodiments, the treatment plan information includes information regarding one or more bundles of predetermined patient care services. The bundles of predetermined patient care services may include a recommended course of treatment tailored to the patient's specific attributes for treatment relevant variables or parameters. In some embodiments, the predetermined treatment plan information associated with the provisional nodal address assigned to the patient of interest is provided to a healthcare provider of the patient or a healthcare payer of the patient. As used herein, the term "treatment relevant variable" refers to a variable that is relevant for guiding an early treatment decision. A minimum subset of the treatment relevant variables is the subset of treatment relevant variables required to provide a recommended course of treatment tailored to the patient's information available at a point in time and to the treatment intent. A variable that may be relevant to treatment and is relevant to prognosis or treatment, but is not required to provide an accurate recommended course of treatment and may or may not be available shortly after diagnosis, may be considered a treatment relevant variable that is not in the minimum subset required for treatment and a prognosis or outcome based variable, or may just be considered a prognosis or outcome based variable. The COTA module assigns a provisional nodal address and a refined nodal address to a patient based on received or accessed data including personal health information associated with the patient as described further below.

In some embodiments, each provisional nodal address is associated with predetermined treatment plan information (e.g., one or more bundles of predetermined patient care services). In some embodiments, only one provisional nodal address is associated with particular predetermined treatment plan information. In some embodiments, one or more provisional nodal addresses are associated with the same predetermined treatment plan information (e.g., information regarding particular one or more bundles of patient care services). In some embodiments, each refined nodal address is associated with predetermined treatment plan information (e.g., information regarding one or more bundles of predetermined patient care services). In some embodiments, more than one refined nodal address is associated with the same predetermined treatment plan information (e.g., the same information regarding one or more bundles of predetermined patient care services). The predetermined treatment plan information associated with a provisional nodal address or a refined nodal address will be updated as needed over time to reflect current standards and guidelines for treatment of a patient having the particular combination of treatment relevant attributes corresponding to the provisional nodal address or the refined nodal address.

In some embodiments, upon accessing or receiving an identification of a patient, the COTA module 220 determines or identifies the provisional nodal address assigned to the patient and provides the predetermined treatment plan information (e.g., the information regarding the one or more bundles of predetermined patient care services) associated with the provisional nodal address (patient care plan functionality 314). In some embodiments, where sufficient initial information is provided or accessed by the system to assign a refined nodal address at a particular start date of a particular analysis, the COTA module 220 provides the predetermined treatment plan information (e.g., information regarding the one or more bundles of predetermined patient care services) associated with the refined nodal address at that time. As noted above, the treatment plan information may include information regarding treatment plans/and or treatment strategies specific to all of the treatment relevant variables or attributes of the patient, as described below. In some embodiments, the treatment plan information includes information regarding one or more bundles of predetermined patient care services.

In some embodiments, the COTA module 220 provides prognosis-related expected outcome information specific to prognosis and outcome relevant variables and attributes of the particular patient via an expected outcome functionality 316 of the COTA module 220. The prognosis-related expected outcome information may be determined for a patient of interest based on the refined nodal address assigned to the patient of interest. For a prognosis-related expected outcome, the outcome is with respect to occurrence of a defined end point. For example, when the prognosis-related expected outcome is overall survival, the defined end point is death from any cause. As another example, when the prognosis-related expected outcome is progression free survival, the end point is progression of the disease, e.g., tumor growth or spread. As another example, when the prognosis-related expected outcome is disease-free survival, the end point is relapse.

Further, in some embodiments the COTA module 220 performs outcome tracking and analysis 320. In some embodiments, providing the prognosis-related expected outcome information 316 is part of the outcome tracking and analysis 320. In other embodiments, providing the prognosis-related expected outcome information 316 may be separate from outcome tracking and analysis 320. In some embodiments, the COTA module 220 tracks outcomes in real time. In some embodiments, the COTA module 220 tracks outcomes periodically. In some embodiments, the COTA module 220 tracks outcomes on demand or as needed. In one embodiment, the outcome tracking includes any or all of the parameters progression free survival, overall survival, performance status/quality of life metrics, incidence/severity of toxicity, (e.g., the degree to which a substance or drug can damage an individual), death, and drug utilization (e.g., delivered dose intensity, dose interval and duration of therapy). Other types of outcomes are also contemplated.

Overall survival may be a trial endpoint, which is usually expressed as a period of time (survival duration), e.g., in months. Frequently, the median is used so that the trial endpoint can be calculated once 50% of subjects have reached the endpoint. An example is disease free survival, which is usually used to analyze the results of the treatment for the localized disease which renders the patient apparently disease free, such as surgery or surgery plus adjuvant therapy. In disease-free survival, the event is relapse rather than death. The people who relapse are still surviving but they are no longer considered disease-free.

Progression free survival is the length of time during and after medication or treatment during which the disease being treated (e.g., cancer) does not get worse. It is sometimes used as a metric to study the health of a person with a disease to try to determine how well a new treatment is working.

The element ECOG performance status/quality of life metrics refers to a method by which the quality of life of the patient over time can be tracked. It is part of the demographic parameter disease specific clinical molecular phenotype, i.e., the stage of a patient's health at the start of therapy, and can be used for sorting. For example, ECOG performance status refers to scales and criteria used by doctors and researchers to assess how a patient's disease is progressing, assess how the disease affects the daily living abilities of the patient, and determine appropriate treatment and prognosis. See Oken, M M, et al, "Toxicity and response criteria of the eastern cooperative oncology group," Am. J. Clin. Oncol. (1982) 5: 649-55. ECOG has values from 0-5, where 0 means the patient is fully active, able to carry on all pre-disease performance without restriction; 1 means restricted in physically strenuous activity but ambulatory and able to carry out work of a light or sedentary nature, e.g., light house work, office work; 2 means Ambulatory and capable of all self-care, but unable to carry out any work activities, up and about more than 50% of waking hours; 3 means capable of only limited self-care, confined to bed or chair more than 50% of waking hours; 4 means completely disabled, cannot carry on any self-care, totally confined to bed or chair; and 5 means dead. A comparison of ECOG at start of therapy with ECOG after therapy reflects some aspects of the effect of the therapy.

In one embodiment, exemplary parameters of the outcome toxicity to therapy are incidence and severity.

In one embodiment, systems and methods enable increased accuracy in at risk financial contracting between payers and providers so the parties can reduce treatment variability, waste and inefficiency while still delivering on the intended outcome.

In some embodiments, the COTA module 220 can also transmit communications, such as alerts 330, to medical professionals (e.g., physicians) (or, in another embodiment, to a patient's insurance company or any other payer entity) in real-time at key points, such as, e.g., at diagnosis, at progression, at dose change/drug change/toxicity, and/or trending towards variance from desired or expected outcome. In one embodiment, the COTA module 220 provides alerts to medical professionals that identify a specific patient for which the medical professional is searching. For example, the COTA module 220 may provide an alert in real time to a pharmaceutical company that is looking for specific patients to administer a specific (e.g., new) drug or drug candidate. The alert may identify a specific patient that is a good candidate for the specific drug. As another example, an alert may be provided to inform a care provider that an outcome of a patient is deviating from an expected outcome for patients having similar treatment and prognosis relevant parameters so that a review of treatment of the patient and possible modification of patient treatment may be undertaken.

As used herein, the term "real-time" or "real time" means without perceivable delay or information that is delivered immediately after collection or processing. These terms also include a time delay introduced by automated processing (e.g., near real-time).

Figure 3A:
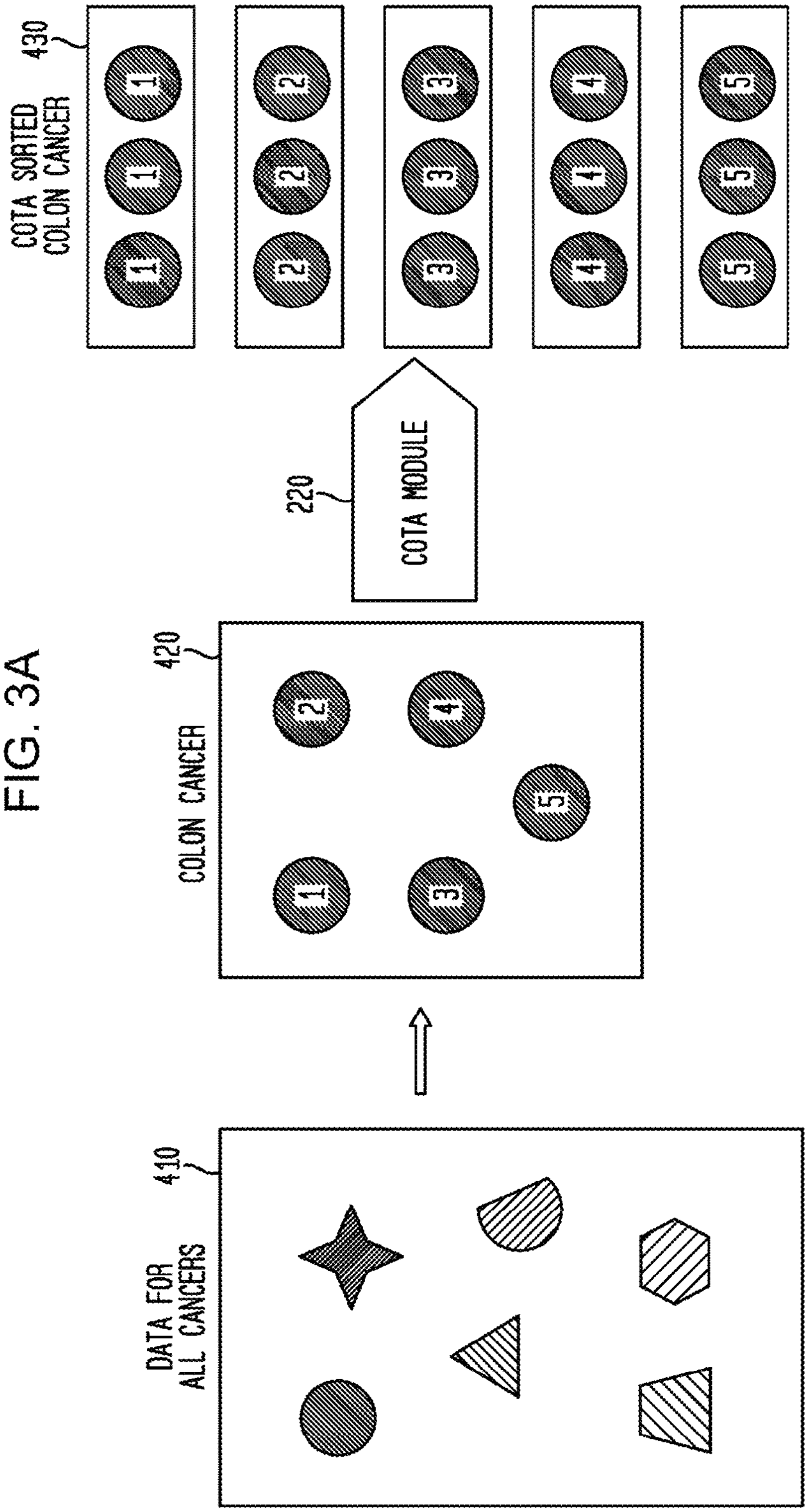
FIG. 3A is a block diagram illustrating use of the COTA module to sort data associated with colon cancer patients in accordance with an embodiment of the present disclosure.

FIG. 3A is a block diagram illustrating sorting data associated with colon cancer patients in accordance with one embodiment. Although described with respect to colon cancer, the description and figure can apply to any type of cancer, or, in another embodiment, any type of disease for which there is data associated with patients.

Data 410 associated with cancer patients is gathered for all cancers (or, in another embodiment, for more than one type of cancer, or, in other embodiments, for all cardiovascular diseases, or pulmonary diseases, or gastrointestinal diseases, or neurological diseases, etc.), and this data 410 is narrowed to a subset 420 relating to, e.g., patients with colon cancer. In one embodiment, the subset 420 of data relating to colon cancer is then analyzed and sorted by the COTA module 220 to produce a sorted colon cancer data set 430. The sorted colon cancer data set 430 can include one or more groupings, where each grouping includes data associated with patients having the same type of specific colon cancer. Thus, the COTA module 220 enables the sorting of patients with like cancers, and data from patients with like cancers to the highest level of fidelity relevant for diagnosis, treatment, and prognosis.

The COTA module 220 classifies, sorts, and facilitates the grouping of types of patients based on combinations of values of or attributes assigned to preselected variables that are embodied in nodal addresses. The preselected variables can include treatment relevant variables and prognosis or outcome relevant variables. The COTA module 220 can generate and assign unique provisional nodal addresses and refined nodal addresses, which embody unique combinations of values of the preselected variables. The provisional nodal address or refined nodal address assigned to a patient, or to which a patient is assigned, embodies a specific combination of values for the preselected variables. In the case of a provisional nodal address, the provisional nodal address may include values for only a subset of the preselected classification variables, for example, only the minimum subset of the treatment relevant variables, which are useful for a medical professional to make an early treatment decision at point of care.

Personal health information for each patient is used to determine the values of the preselected variables, which are referred to as attributes herein that are used to assign the provisional nodal address and the refined nodal address for the patient. In some embodiments, at least some of the personal health information, such as the initial treatment relevant information for assignment of the provisional nodal address, may be entered or provided by a medical services provider in a structured form. In some embodiments, at least some of the personal health information may be accessed from data from a health record of the patient. In some embodiments, at least some of the personal health information used to determine attributes for a refined nodal address is accessed from or obtained from a health record of the patient.

Typically, patient information is stored in electronic medical records (EMRs). EMRs, however, often contain too much information and it is therefore difficult for a medical professional to locate specific information of interest from the large amount of information stored in EMRs. Further, most of the information in EMRs is not relevant to the information for which the medical professional is searching. Unlike EMRs, whose goal is to capture all or most of the data associated with a patient coming into a doctor's office and the patient leaving the doctor's office, the COTA module 220 is targeted, as the module 220 enables a user to locate specific data relevant to diagnosis and prognosis associated with particular patients.

In some embodiments, information accessed or received for treatment relevant variables for determination of a provisional nodal address may be received by a user selection (e.g., via a web browser, software executing on a client device, or via an app). In some embodiments, at least some of the data that the COTA module 220 receives is via a web page, and is discrete (e.g., typically provided by a user selecting one or more choices in a menu, via one or more check boxes or a button, etc.). In some embodiments, at least some of the patient data is received as data in structured fields. In some embodiments, information accessed or received relevant to variables for a determination of a refined nodal address may be provided, in part, as data from a medical record for the patient. In some embodiments, the COTA module 220 accesses unstructured personal health information and identifies and selectively extracts data relevant to diagnosis and prognosis. See, for example, U.S. Patent Application Publication No. US 2018/0121618 A1, entitled "SYSTEM AND METHOD FOR EXTRACTING ONCOLOGICAL INFORMATION OF PROGNOSTIC SIGNIFICANT FROM NATURAL LANGUAGE," published May 3, 2018, which is incorporated by reference herein in its entirety. In some embodiments, methods for obtaining initial data after diagnosis may be different, at least in part, than methods for obtaining later data relevant to prognosis or outcome.

In one embodiment, data can be ingested into the system via a human user or a technical process, e.g., an API. In some embodiments, a layer of the COTA module 220 can parse and assess the data as it is ingested. For example, the COTA module 220 can check whether the data is correct, corrupt, completeness of the data, format of the data, spelling, as well as other factors to verify the integrity of the data. In some embodiments, the COTA module 220 can correct detected issues with the data. In some embodiments, the COTA module 220 assesses the data, e.g., whether it is correct, whether it is corrupt, what information is there, what information is missing/holes in the information, how it is formatted, spelling, etc., and corrects any problems with the information it detects to date. In some embodiments, checking, verification and/or correction of detected issues in the data occurs, at least in part, during ingestion of the data. In some embodiments, checking, verification and/or correction of detected issues in the data occurs, at least in part, after ingestion of the data. The COTA module 220 can store the ingested data in the database(s) 240*a*, 240*b*. Some methods for checking and verifying input data are described in US 2018/0121618 A1, which is incorporated by reference herein in its entirety. In some embodiments, the data accessed or received relevant to variables for determination of a refined nodal address may be subjected to checking, verification and/or correction of detected issues in the data, before and/or after ingestion of data from the medical record.

A level of checking, verification, and/or correction of detected issues in the data may be different for data provided or accessed for initial determination of a provisional nodal address than for determination of a refined nodal address. This may be due in part to a different format, method or mechanism for entering or obtaining data for the two different types of nodal addresses in some embodiments. In some embodiments, as noted above, a more structured format may be employed for initially obtaining information for treatment relevant variables. This may facilitate efficient assignment of a provisional nodal address and rapid or immediate on demand access to predetermined treatment plan information (e.g., one or more bundles of predetermined patient services) that may be associated with the provisional nodal address to guide treatment decisions early (e.g., at diagnosis, shortly after diagnosis, during a first appointment after diagnosis). In some embodiments, a structured format may also be employed for a user to enter information for some prognosis or outcome relevant variables. In other embodiments, at least some of the data for prognosis or outcome relevant variables may be provided as medical record data that may include data in a non-structured format. This type of data may require more checking, verification and/or correction of detected issues in the data. Further, initial assignment of the refined nodal address may be less time sensitive, as it is not being used to guide early treatment decisions. In some embodiments, if the initial information received or accessed includes information sufficient to assign attributes for at least the minimum subset of treatment relevant variables and the minimum subset of prognosis or outcome relevant variables, a refined nodal address may be assigned to the patient without a provisional nodal address having been assigned to the patient.

The COTA module 220 assigns a provisional nodal address and/or a refined nodal address to a set of personal health information regarding a patient based on values, referred to as attributes, of the preselected variables included in the provisional nodal address or in the refined nodal address. In some embodiments, after a refined nodal address is assigned, the provisional nodal address is no longer used, e.g., the provisional nodal address is only used to guide the healthcare professional making treating decisions at the point of care shortly after diagnosis. In some embodiments, after a refined nodal address is assigned, the refined nodal address can be used to access predetermined treatment plan information associated with the refined nodal address assigned to the patient.

As noted above, preselected variables can include treatment relevant variables and prognosis or outcome relevant variables. In some embodiments, at least some treatment relevant variables are also prognosis or outcome relevant variables. A provisional nodal address includes attributes corresponding to at least a minimum subset of the treatment relevant preselected variables. For a provisional nodal address to be assigned to a patient or to data records associated with a patient, personal health information associated with the patient that is supplied to the system or method or accessed by the system or method must include sufficient information to assign attributes to at least the minimum subset of the treatment relevant variables. In some embodiments, which variables are included in the minimum subset of the treatment relevant variables depends on the cancer type and or more of the cancer stage and the treatment intent, as described in further detail below. In some embodiments, the minimum subset of the treatment relevant variables is less than all of the treatment relevant variables and a provisional nodal address is assigned when at least the minimum subset of the treatment relevant variables are assigned even if all of the treatment relevant variables are not assigned. In some embodiments the minimum subset of the treatment relevant variables is all of the treatment relevant variables, and attributes must be assigned to all of the treatment relevant variables for a provisional nodal address to be assigned. As explained above, a variable that is relevant to treatment (e.g., relevant to later stages of treatment), but whose value may not be available at or shortly after diagnosis (e.g., within days of diagnosis) and that is not required for determining an accurate early treatment recommendation may be considered a treatment relevant variable that is not included in the minimum subset in some embodiments. If the variable is also relevant to prognosis and outcome, in some embodiments where the minimum subset of the treatment relevant variables includes all the treatment relevant variables, this variable may be considered only a prognosis and outcome relevant variable and not a treatment relevant variable even though it has some relevance to treatment. Thus, the decision of whether a variable is a considered a treatment relevant variable within the set of preselected variables and/or as part of the minimum subset of treatment relevant variables depends on how relevant the variable is for providing an accurate recommendation for a course of treatment, and the likelihood that information regarding the variable will be available for most patients in time to guide an early treatment decision, and may also be dependent on values of one or more other variables, such as, for some cancers, cancer type and treatment intent. An early treatment decision may be a treatment decision made within 3 days of diagnosis, within 5 days of diagnosis, within 7 days of diagnosis, within 10 days of diagnosis, within a week of diagnosis, within 2 weeks of diagnosis, within 3 weeks of diagnosis, or within a month of diagnosis.

In some embodiments, the treatment relevant variables, the prognosis or outcome relevant variables or both are selected by a group of national experts (e.g., a national panel of subspecialists), who meet periodically (e.g., monthly). These experts are aware of all key literature in the disease and all key biomarkers, and maintain a list of the preselected variables determined based on published literature and their own expertise. In some embodiments, the experts categorize the preselected variables as relevant to treatment, or prognosis or outcome, or both. If a variable is relevant to treatment and relevant to prognosis or outcome, it is considered a treatment relevant variable for purposes of determining whether at least a minimum subset of the treatment relevant variables are assigned, and for purposes of assigning a provisional nodal address.

Updated and/or additional personal health information associated with a patient is supplied to the system, received by the system, or accessed by the system at a later time or over a later period of time after the initial nodal address is assigned. In some embodiments, the initial nodal address may be a provisional nodal address where at least a minimum subset of the treatment relevant variables, but less than the minimum subset of the prognosis or outcome relevant variables are assigned, or may be a refined nodal address where at least the minimum subset of the treatment relevant variables and the minimum subset of the prognosis or outcome relevant variables are assigned. If the initial nodal address assigned was a provisional nodal address and the updated and/or additional personal information includes sufficient information to assign attributes to at least the minimum subset of the treatment relevant variables and to at least a minimum subset of the prognosis or outcome relevant variables, the patient, or the personal health information associated with the patient, is assigned a refined nodal address.

In some embodiments, if new or updated attributes are assigned for at least some of the treatment relevant variables based on the new or updated personal health information, but the updated and/or additional personal health information in combination with the initial personal health information does not enable attributes to be assigned for at least the minimum subset of the prognosis or outcome relevant attributes, the patient will be assigned an updated provisional nodal address. In other embodiments, if new or updated attributes are assigned for at least some of the variables based on the new or updated personal health information, but the updated and/or additional personal health information does not enable attributes to be assigned for at least the minimum subset of the prognosis or outcome relevant variables, the system or method does not assign an updated provisional nodal address, but instead waits for additional information that, in combination with the previously received or accessed information, would be sufficient to assign a refined nodal address. If the initial nodal address assigned was a refined nodal address and the new or updated personal health information includes new or updated values for one or more of the treatment relevant variables or the prognosis or outcome relevant variables, the patient may be assigned an updated refined nodal address based on the new or updated values.

Upon receipt of additional subsequent personal health information over time, a refined nodal address may be assigned to the patient (if the patient was not previously assigned a refined nodal address), or the refined nodal address assigned to the patient may be updated.

For example, in one embodiment, personal health information regarding a patient of interest is provided to or accessed by a method or system at or shortly after diagnosis of the patient and the personal health information provided includes information regarding attributes for at least the minimum subset of the treatment relevant preselected variables, but includes information regarding less than the minimum subset of prognosis or outcome relevant variables. A provisional nodal address is assigned to the patient of interest based on attributes for the treatment relevant variables. At a later time, additional personal health information (e.g., additional test results) regarding the patient of interest is provided to or accessed by the method or system and the additional personal health information includes sufficient information regarding attributes for at least the minimum subset of the prognosis or outcome relevant variables for the patient of interest to be assigned a refined nodal address based on attributes for the treatment relevant variables and the attributes for the prognosis or outcome relevant variables, and the patient of interest is assigned the refined nodal address based on the additional personal health information alone or in combination with the initial personal health information.

In one embodiment, the provisional nodal address and the refined nodal address are used to classify like data or like patients. For example, because patients assigned the same provisional nodal address all have the same attributes for treatment relevant variables, an analysis of prior or current treatment for all patients assigned the same provisional nodal address enables a comparison of like patients with respect to treatment. In some embodiments, an analysis may be performed with respect to a treatment relevant group, where each patient in the treatment relevant group is included in the treatment relevant group based on the provisional nodal address that is or was assigned to the patient. In some embodiments, a patient may alternatively be assigned to a treatment relevant group based on treatment relevant variables of a refined nodal address assigned to the patient at or shortly after diagnosis, or at some other point in disease progression relevant to the analysis. As explained in further detail below, patients included in a treatment relevant group or a prognosis or outcome relevant group are assigned based on the nodal address (e.g., the refined nodal address) assigned to the patient at a particular point or stage in the disease progression of the patient, which is determined based on the goal of the analysis for the treatment relevant group or the prognosis or outcome relevant group.

As another example, because patients assigned the same refined nodal address all have the same attributes for treatment relevant variables and for prognosis or outcome relevant variables, an analysis of prior or current outcome with respect to all patients who are or were assigned the same refined nodal address at a particular point in disease progression reduces or eliminates the effect of biological variability on outcome, leaving health care provider performance as a major source of variability in outcome. Further, determination of an expected prognosis-related outcome for a patient of interest may be based on prior outcomes for a prognosis or outcome based group of patients, where each patient in prognosis or outcome based group was assigned the same refined nodal address as that of the patient of interest at a corresponding point in disease progression as that of the patient of interest. In some embodiments, more than one refined nodal address may be included in the group for analysis of prior or current outcome. For example, if a treatment relevant parameter is not relevant for outcome, different refined nodal addresses with different values of the treatment relevant parameter may be grouped together for the analysis. In some embodiments, the prognosis or outcome based group of patients may include some patients who were assigned different refined nodal addresses at a corresponding point in disease progression from that assigned to the patient of interest, where the different refined nodal addresses have different values of a variable or variables not relevant or less relevant to prognosis or outcome or to a particular type of prognosis or outcome.

For example, because of the nature of ordering diagnostic tests and waiting for results, some of the test results, which may be relevant to treatment, but more relevant to prognosis or outcome, may not be available at the time of diagnosis or shortly after diagnosis (e.g., within days of diagnosis or within a week of diagnosis). Nevertheless a provisional nodal address can be assigned to the patient based on the limited subset of treatment attributes then available assuming that information is provided or can be accessed regarding attributes for at least the minimum subset of treatment relevant variables. The test results not commonly available at or shortly after the time of diagnosis may be characterized as prognosis or outcome relevant variables in some embodiments. At a later time when additional test results are available, a refined nodal address can be assigned to the patient of interest based on information from the additional test results. Over time, additional patient information may become available, which correlates to treatment, prognosis (can address how far the disease has progressed and correlate that to survival) and historical cost of care. Accordingly, each provisional nodal address and refined nodal address is an identifier of the patient at a particular point in time or in a particular period of time, like a snapshot of the patient at the particular point in time or in a particular period of time. After assignment of the provisional nodal address, the patient is assigned a refined nodal address based on additional information, which is updated over time based on new or changed personal health information for the patient. In some embodiments, the provisional nodal addresses and refined nodal addresses enable a user to easily and efficiently compare like patients to like patients with respect to variables relevant for treatment and/or prognosis or outcome during analysis. This specificity of comparison enables minimizing biological variability of outcome during an analysis and, as a consequence, may provide greater precision regarding the effect of therapeutic agents, treatment or interventions on outcome.

The refined nodal addresses and provisional nodal addresses can be stored in the one or more databases **240*a*, 240*b*. Information regarding a provisional nodal address assigned to a particular patient and or a refined nodal address assigned to the particular patient and corresponding to a point or period in the patient's disease progression can be stored in the one or more databases 240*a*, 240*b***. Information regarding other patients, which may include historical cost information, can also be stored in the one or more databases 240*a*, 240*b*. The COTA module 220 associates each provisional nodal address with a specified combination of attributes for each treatment relevant variable in at least the minimum subset of treatment relevant variables and associates each refined nodal address with a specified combination of attributes for each treatment relevant variable in at least the minimum subset of treatment relevant variables and for each prognosis or outcome relevant variable in at least the minimum subset of prognosis or outcome relevant variables.

The provisional nodal address is by definition based only on attributes for treatment relevant variables. As noted above, in some embodiments, the treatment relevant variables are selected based on the expertise of a panel of experts and published literature that impact treatment decisions. In general, the minimum set of treatment relevant variables required to assign a provisional nodal address includes variables whose values are known at the time of diagnosis or shortly after the time of diagnosis that are relevant to treatment decisions. As noted above, which variables are included in the minimum subset of treatment relevant variables may depend on values of one or more treatment relevant variables, e.g., for cancer, the minimum subset of treatment relevant variables may depend on the cancer type, cancer stage, and/or treatment intent. Values for at least some of the prognosis or outcome relevant variables may be unknown at the time of diagnosis. As noted above, some variables may be both treatment relevant variables and prognosis or outcome relevant variables.

Based on the acquisition of, receipt of, or access to additional personal health information about the patient that impacts treatment decisions over time, in some embodiments, the provisional nodal address assigned to the patient is updated based on new or changed values for treatment relevant variables. In some embodiments, based on the acquisition of, receipt of, or access to additional personal health information, a refined nodal address or an updated refined is assigned to the patient based on values/attributes for the treatment relevant variables and attributes/values for the prognosis or outcome relevant variables. Expected outcome can be determined based on the refined nodal address assigned to the patient using prior outcome data for patients who were or are assigned the same refined nodal address as that assigned to the patient of interest at a corresponding point in disease progression. Further, an expected cost of treatment for the patient of interest can be determined based on historical cost data for other patients who were assigned the same refined nodal address as that assigned to the patient of interest at the same point in disease progression as that of the patient of interest. In some embodiments, the comparison is with patients who were assigned the same refined nodal address as that of the patient of interest at the same point in disease progression and treatment as that of the patient of interest. In some embodiments, an expected total cost of care is determined, where a "total cost" is the cost of care from diagnosis to death or cure. By determining the expected total cost of care using historical cost information for patients assigned the same refined nodal address as that assigned to the patient of interest at the corresponding point in disease progression as the patient of interest, the determined expected total cost of care takes into account risk associated with the patient of interest's particular combination of treatment and prognosis and outcome relevant attributes.

As explained above, in some embodiments, the COTA module 220 associates each nodal address (e.g., provisional nodal address and/or refined nodal address) with a combination of specified attributes for at least some of the preselected variables. As explained above, the provisional nodal address includes attributes for only treatment relevant variables, but the refined nodal address includes attributes for treatment relevant variables and prognosis or outcome relevant variables. The preselected variables can be factors related to a patient and a disease such as a cancer associated with the patient. The preselected variables can include variables relevant to diagnosis, treatment and prognosis of a specific disease or disorder, of a grouping of similar diseases or disorders, or of a category of diseases or disorders. As an example, in some embodiments, the preselected variables can include diagnoses, demographics, outcomes, phenotypes, etc.

In some embodiments, the preselected variables are defined by or identified by a group of experts in the relevant field(s) (e.g., oncologists with more than 5, 10, 15, 20, 30, etc. years of experience). In some embodiments, the preselected variables are defined or identified based, at least in part, on information regarding current medical knowledge and treatment and/or information from experts in the relevant field. In some embodiments, definition or identification of the preselected variables to be included in the provisional nodal addresses and refined nodal addresses are updated based on new information regarding current medical knowledge and treatment and/or updated information from experts in the field. In some embodiments, the definition or identification of the preselected variables is updated on a periodic schedule. In some embodiments, the definition or identification is updated as needed based on newly available information.

The COTA module 220 can store the definition or identification of the preselected variables in one or more databases 240*a*, 240*b*. It can be appreciated that the definition of preselected variables can change over time for any given disease. The preselected variables include treatment relevant variables and prognosis or outcome relevant variables, as described above and in more detail below.

The definition or identification of the preselected variables may be specific to the disease or disorder. In some embodiments, the treatment relevant variables and the prognosis or outcome relevant variables may be specific to the type of cancer (e.g., breast cancer, colon cancer, prostate cancer, rectal cancer, lung cancer, etc.). For example, for breast cancer, treatment relevant variables may include estrogen receptor (ER) status, human epidermal growth factor 2 (HER2) status, stage, and ECOG. Prognosis or outcome relevant variables may include information regarding genetic testing results, such as an Ocotype DX score, or information regarding comorbidities. In some embodiments, genetic testing results such as the Oncotype DX score, which will likely not be available shortly after diagnosis, may be considered a prognosis or outcome relevant variable, but not a treatment relevant variable.

As noted above, which variables are included in the minimum subset of treatment relevant variables may depend on some treatment relevant variables, such as for cancer, cancer type, stage, and/or treatment intent. Even for a single specific disease or disorder such as breast cancer, the identification of the minimum set of treatment relevant variables may be specific to a stage and/or treatment intent.

For example, for breast cancer, the minimum set of treatment relevant variables may depend on whether the treatment intent is adjuvant therapy (meaning additional cancer treatment given after the primary treatment to lower the risk that the cancer will come back; adjuvant therapy may include chemotherapy, radiation therapy, hormone therapy, targeted therapy, or biological therapy), neoadjuvant therapy (meaning treatment given as a first step to shrink a tumor before the main treatment, which is usually surgery, is given; examples of neoadjuvant therapy include chemotherapy, radiation therapy, and hormone therapy), or therapy for metastatic cancer. For example, the minimum set of treatment variables for breast cancer where the treatment intent is adjuvant therapy may include: therapy type, sex, tumor node metastasis (TNM) stage, ECOG status, treatment relevant co-morbidity type (meaning an illness other than the principal diagnosis that influences the outcome of treatment), histologic grade, histology, human epidermal growth factor receptor 2(Her 2) status, (estrogen receptor (ER) status, progesterone receptor (PR) status, whether there is extensive lymphovascular invasion, and menopausal status. With regard to treatment relevant co-morbidity type, for example, a patient with severe underlying COPD is not a good candidate for resection of a lung malignancy and therefore their chance of cure is decreased. Similarly, a diagnosis of congestive heart failure precludes some cancer treatments. Summary comorbidity measures, for example, the Charlson Index, Adult Comorbidity Evaluation 27 (ACE-27), attempt to assess the combined impact of different diseases. See Geraci, J M et al, J. Clin. Oncol. (2005) 23(30): 7399-7404, which is incorporated by reference herein in its entirety. The additional prognosis or outcome relevant variables may include: patient preference for treatment, genomic test results such as BRCA 1 mutation status, BRCA 2 mutation status, and Partner and Localizer of BRCA2 (PALB 2) mutation status, genetic testing results such as Oncotype DX recurrence score (for an invasive breast cancer), Oncotype DX DCIS (for ductal carcinoma in situ (DCIS) only), and the Breast Cancer Index test, whether patient is African American, and age. In some embodiments, some of the aforementioned variables, such as one or more of BRCA 1 mutation status, BRCA 2 mutation status, and PALB 2 mutation status, and genetic testing results such as Oncotype DX recurrence score (for an invasive breast cancer), Oncotype DX DCIS (for ductal carcinoma in situ (DCIS) only), and the Breast Cancer Index test, may be considered treatment relevant variables that are not included in the required minimum subset of treatment relevant variables in addition to being prognosis or outcome relevant variables, such that a provisional nodal address may be assigned even if attributes are not assigned for these variables. In other embodiments, one or more of BRCA 1 mutation status, BRCA 2 mutation status, and PALB 2 mutation status, and genetic testing results such as Oncotype DX recurrence score (for an invasive breast cancer), Oncotype DX DCIS (for ductal carcinoma in situ (DCIS) only), and the Breast Cancer Index test may only be considered prognosis and outcome relevant variables and not considered treatment relevant variables.

As another example, the minimum set of treatment relevant variables for breast cancer where the treatment intent is neoadjuvant therapy may include: therapy type, sex, TNM stage (meaning a system to describe the amount and spread of cancer in a patient's body T, which describes the size of the tumor and any spread of cancer into nearby tissue; N, which describes spread of cancer to nearby lymph nodes; and M which describes metastasis or spread of cancer to other parts of the body), ECOG status, treatment relevant co-morbidity type, Her 2 status, ER status, PR status, and menopausal status. The additional prognosis or outcome relevant variables may include: patient preference for treatment, genomic test results such as BRCA 1 mutation status, BRCA 2 mutation status, PALB 2 mutation status, genetic testing results such as the Breast Cancer Index test, whether the patient is African American, age, histologic grade, histology, and whether there is extensive lymphovascular invasion.

As another example, the minimum set of treatment relevant variables for breast cancer where the treatment intent is therapy for metastatic cancer may include: sex, ECOG status, treatment relevant co-morbidity type, Her 2 status, ER status, PR status, and menopausal status. The prognosis or outcome relevant variables may include: patient preference for treatment, genomic test results such as BRCA 1 mutation status, BRCA 2 mutation status, PALB 2 mutation status, whether the patient is African American, age, and metastatic site.

As another example, for adjuvant therapy of Stages I-IIIC prostate cancer, the minimum set of treatment relevant variables may include: ECOG status, TNM stage, Gleason score, which ranges from 1-5 and describes how much the cancer from a biopsy looks like healthy tissue (lower score) or abnormal tissue (higher score), and prostate-specific antigen (PSA) test results. For therapy for metastatic prostate cancer, the minimum set of treatment relevant variables may include: ECOG status, TNM stage, and progression track.

As another example, for adjuvant therapy of colon cancer other than Stage II, the minimum set of treatment relevant variables may include: ECOG status, TNM stage, and comorbidity type. For adjuvant therapy of colon cancer for Stage II, the minimum set of treatment relevant variables may include: ECOG status, TNM stage, comorbidity type, microsatellite instability (MSI) status (meaning a hypermutable phenotype caused by the loss of DNA mismatch repair activity; see Boland, C R and Goel, A., Gastroenterology (2010) 138(6): 2073-87; doi: 10.1053/j.gastro.2009.12.064)), whether fewer than 12 nodes were sampled, obstruction, perforation, and T stage. T0 (carcinoma in situ or intramucsosal carcinoma (Tis) means that the cancer has not grown beyond the inner layer (mucosa) of the colon or rectum. colon or rectum. T1 means the cancer has grown through the muscularis mucosa into the submucosa (T1). T2 means the cancer has also grown into the muscularis propria. NO means that cancer has not spread to nearby lymph nodes. M0 means the cancer has not spread to distant sites. T3 means the cancer has grown into the outermost layers of the colon or rectum but has not gone through them, it has not reached nearby organs, it has not spread to nearby lymph nodes (N0), and it has not spread to distant sites (M0). T4a means the cancer has grown through the wall of the colon or rectum but has not grown into other nearby tissues or organs (T4a), and it has not yet spread to nearby lymph nodes (N0) or to distant sites (M0). T4(b) means the cancer has grown through the wall of the colon or rectum and is attached to or has grown into other nearby tissues or organs (T4b), and it has not yet spread to nearby lymph nodes (NO) or to distant sites (M0). (https://www.cancer.org/cancer/colon-rectal-cancer/detection-diagnosis-staging/staged.html). For therapy for metastatic colon cancer, the minimum set of treatment relevant variables may include: ECOG status, TNM stage, progression track, MSI status, KRAS mutation status, NRAS mutation status, BRAF mutation status, and tumor sidedness.

As another example, for neoadjuvant and adjuvant therapy of rectal cancer, the minimum set of treatment relevant variables may include: ECOG status, TNM stage, and location. For therapy for metastatic rectal cancer, the minimum set of treatment relevant variables may include:

ECOG status, TNM stage, progression track, MSI status, KRAS mutation, NRAS mutation, and BRAF mutation.

As another example, for adjuvant or neoadjuvant treatment of non-small cell lung cancer (NSCLC), the minimum set of treatment relevant variables may include: TNM stage, histology, ECOG status, and comorbidities. For treatment of metastatic NSCLC that is symptomatic and needs immediate treatment, the minimum set of treatment relevant variables may include: histology, comorbidities, and ECOG status. For treatment of NSCLC that is not symptomatic and/or does not need immediate treatment, the minimum set of treatment relevant variables may include: histology, comorbidities, ECOG status, programmed death-ligand 1 (PD-L1) expression, EGFR mutation status, and anaplastic lymphoma kinase (ALK) mutation status. For treatment of small cell lung cancer (SCLC), the minimum set of treatment relevant variables may include: ECOG status, comorbidity, and TNM stage.

Figure 3B:
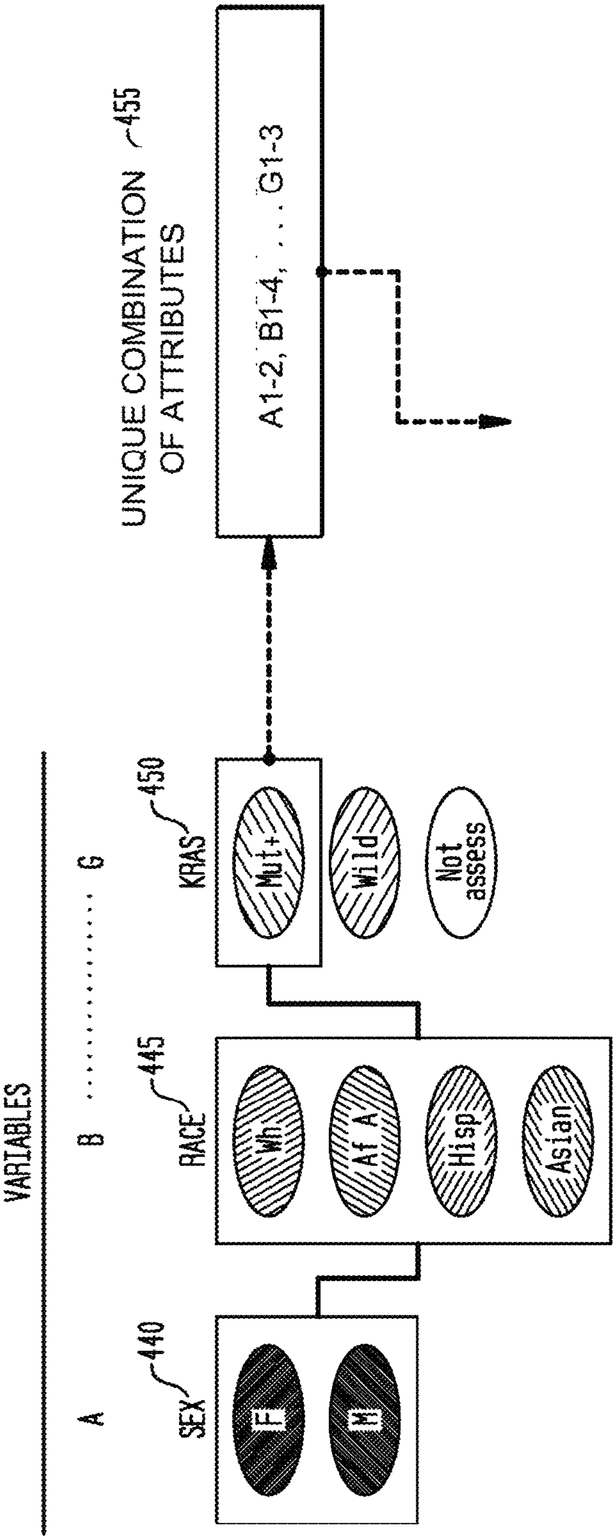
FIG. 3B schematically depicts aspects of the COTA module sorting data by employing unique combinations of attributes corresponding to nodal addresses in accordance with an embodiment of the present disclosure.

FIG. 3B is a flow diagram of assigning a provisional nodal address or a refined nodal address in accordance with some embodiments. In one embodiment, as described above, the COTA module 220 can ingest data, confirm the integrity of the data, validate, and/or correct the data, and store the data in a database 240*a*, 240*b* prior to assignment of a refined nodal address. In some embodiments, the COTA module may receive or access data input via user selections and perform more limited confirmation and validation of the data prior to assignment of a provisional nodal address.

The data ingested or accessed by the COTA module includes personal health information (PHI) associated with a patient. As used herein, PHI refers to any information in a medical record or designated record set that can be used to identify an individual patient and that was created, used, or disclosed in the course of providing a health care service such as diagnosis or treatment. Examples of personal identifiers in PHI include, without limitation, name, all geographical subdivisions smaller than a state, including street address, city, county, precinct, zip code; all elements of dates (except year) for dates directly related to an individual, including birth date, admission date, discharge date, date of death, and age and all elements of date (including year) indicative of such age; phone numbers; fax numbers; electronic mail addresses; social security numbers, medical record numbers; health plan beneficiary numbers; account numbers; certificate/license numbers; vehicle identifiers and serial numbers, including license plate numbers; device identifiers and serial numbers; web Universal Resource Locators (URLs); Internet Protocol (IP) address numbers; biometric identifiers, including finger and voice prints; full face photographic images and any comparable images; and any other unique identifying number, characteristic, or code (but not the unique code assigned by the investigator to code the data). The PHI can include phenotypic characteristics of patients. A phenotype is the composite of a person's observable characteristics or traits, such as its morphology, development, biochemical or physiological properties, phenology, behavior, and products of behavior. Phenotypes result from the expression of a person's genes as well as the influence of environmental factors and the interactions between the two.

In some embodiments, a user, such as a health care provider, patient, or payer/insurance company, can input PHI of a patient into the GUI 250 rendered by the COTA module 220. As an example, the PHI can be uploaded using specified file formats. In some embodiments, at least some of the PHI can be received or accessed based on user selections of values for at least some variables, e.g., via selections from options in a graphical user interface of a web browser, an application, or a mobile app. The computing system 205 can receive the PHI via the COTA module 220 and store the PHI in the database. In other embodiments, the COTA module may access storage including a copy of PHI regarding one or more patients and may obtain PHI regarding the one or more patients in this manner. The COTA module 220 can receive or access an initial set of PHI for patients and subsequently receive updated sets of PHI.

For example, PHI for a patient can be input into a browser, at least in part. In other embodiments, at least some of the PHI is retrieved from a database including stored patient data. In some embodiments, the PHI is sent to a classification layer that determines attributes for at least some of the predetermined variables based on the PHI. In some embodiments, the classification layer also performs checking, verification and correction of at least some of the data prior to or during determination of the attributes. Based on the attributes of at least some of the predetermined variables, a provisional nodal address or a refined nodal address is determined for the patient data and the provisional nodal address or the refined nodal address is assigned to the patient. In some embodiments, once the provisional nodal address or refined nodal address is assigned, each time that a user accesses the COTA module, the COTA module provides access to personal health information regarding the patient and information regarding associations for the nodal address assigned to the patient based on the PHI (e.g., through a graphical user interface) or information regarding the nodal address itself. In some embodiments, the COTA module enables efficient comparison of PHI regarding a particular patient to information regarding other patients having or who had like attributes for some or all of the predetermined variables encoded in the nodal address at a corresponding point in progression as the particular patient. In some embodiments, the comparison is with other patients who were assigned the same refined nodal address as that assigned to the particular patient at a corresponding point in both disease progression and treatment.

In one embodiment, the COTA module 220 can access or receive an initial set of PHI for a patient. The COTA module 220 can assign attributes for at least some of a set of preselected variables based on values in the PHI for the preselected variables. In some embodiments, attributes can be designated inputs assigned for the preselected variables. For example, attributes can be one or more selections from a specified list or menu. Alternatively, the attributes can be alphanumeric input. As noted above, in some embodiments, attributes are determined, at least in part, from PHI included in one or more unstructured documents in a natural language.

FIG. 3B is a flow diagram of COTA classifying and sorting as described above through creation of nodal addresses embodying different unique combinations of attributes in accordance with one embodiment. As shown in FIG. 3B, as an example, with reference to FIG. 3B, the set of preselected variables can include sex or gender 440 (variable A), race 445 (variable B), variables C, D, E, and F, which are not identified, and KRAS 450 (variable G). K-Ras is a protein that in humans is encoded by the KRAS gene. The protein product of the normal KRAS gene performs an essential function in normal tissue signaling, and the mutation of a KRAS gene is an important step in the development of many cancers.

In some embodiments, the COTA module analyzes the classified and sorted data 430 with respect to combinations of attributes for the set of preselected variables (e.g., variables 440, 445, 450) to identify each a unique combination of attributes in the classified and sorted data. Each unique combination of attributes 455 is embodied in or represented by a unique nodal address. In some embodiments, the format of the nodal addresses indicates the value of each attribute in the preselected variables for the unique combination. The data for a particular patient corresponding to a particular point in time or a particular period in time is assigned one of the unique nodal addresses, either a provisional nodal address or a refined nodal address. Multiple different patients can be assigned the same provisional nodal address or the same refined nodal address. As explained above, the nodal addresses can be used to filter and sort the data. The variables may include, e.g., diagnoses, demographics, outcomes, phenotypes, etc. A phenotype is the composite of a person's observable characteristics or traits, such as its morphology, development, biochemical or physiological properties, phenology, behavior, and products of behavior. Phenotypes result from the expression of a person's genes as well as the influence of environmental factors and the interactions between the two. In some embodiments, nodal addresses enable efficient partitioning of data into clinically relevant groupings.

As noted above, the unique combination of attributes for the preselected variables 455 is represented as a nodal address within the COTA module 220. In one embodiment, the nodal address is represented as a list of the attributes for the predetermined variables (as a function of a letter representing the variable and a number representing the selection of the attribute for that variable). For example, as shown in FIG. 3B, the unique combination of attributes 455 represented as a nodal address includes A1-2 (A represents the sex or gender variable, and 1-2 represents Female and Male patients) shown with a block around both Female and Male variables of Sex variable A. The unique combination of attributes 455 also includes B1-4 with B representing the Race variables and 1-4 representing the different options for the Race variable. The unique combination of attributes 455 also includes G representing the KRAS variable and numbers 1-3 representing different options for the KRAS variable. Thus, in some embodiments, the unique combination of variables 455 can have a node address of A1-2, B1-4, . . . G1-G3 (e.g., A1, B2, . . . G1).

In another embodiment, the refined nodal address or provisional nodal address is represented as a plurality of strings of digits separated by periods, where each string of digits indicates one or more preselected variables and attributes assigned to the variables (e.g., disease, phenotype, therapy type, progression/track, sex, etc.). For example, a first string of digits may represent a particular disease, a second string of digits may represent a type of the disease, a third string of digits may indicate a subtype of the disease, and a fourth string of digits may indicate a phenotype. Thus, in this example, the first string of digits may be 01 indicating cancer, the second string of digits may be 02 indicating breast oncology, a third string of digits may be 01 indicating breast cancer, and a fourth string of digits may be 1201 representing particular characteristics of a phenotype such that the nodal address is 01.02.01.1201. It should be understood that the refined nodal address or provisional nodal address may include any number of strings of digits and is not limited to four strings. Further, the refined nodal address and the provisional nodal address are not limited to being represented by a string of digits. Provisional nodal addresses and refined nodal addresses can be represented in any format as long as the format conveys the information that characterizes and identifies the combination of attributes of the preselected variables that are represented by the nodal address.

Figure 3C:
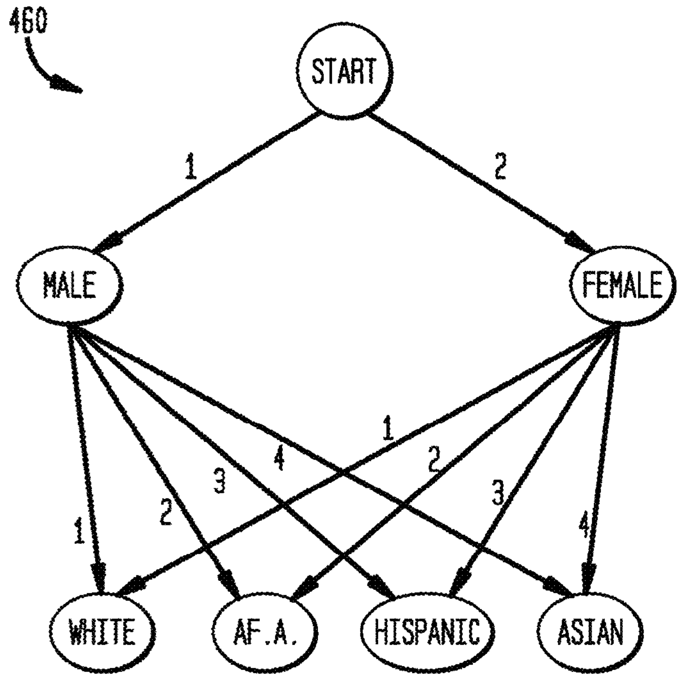
FIG. 3C is a block diagram illustrating a directed graph for determining a string of digits representing phenotype characteristics for nodal addressing in accordance some embodiments of the present disclosure.

In one embodiment, the string of digits representing the phenotype may be provided by representing characteristics of the phenotype as a directed graph. FIG. 3C schematically depicts a directed graph 460 showing characteristics of a phenotype to provide a string of digits representing the phenotype in accordance with one embodiment. The directed graph 460 includes nodes depicted as ovals representing phenotypes and edges representing relationships between nodes. The graph is traced starting from root "start" node to nodes for a selected phenotype. Each edge is associated with a number. The string of digits representing the phenotype for the node address is provided as a combination of the numbers. For example, the string of digits for selected phenotype characteristics of male and white would be represented as 11. Other types of combinations may also be employed. Advantageously, representing characteristics of the phenotype as a directed graph allows for the addition of other nodes corresponding to other phenotypes without changing the entire structure. FIG. 3C includes one way of graphically depicting the directed graph. One of ordinary skill in the art will understand that the directed graph may be graphically depicted in different ways.

The nodal address representing the unique combination of attributes 455 provides the COTA module 220 with the ability to match resources and alerts specific to each phenotype where relevant. Resources can be information, content, link to live support, etc. In some embodiments, each patient is categorized into one or more refined nodal addresses and/or into a provisional nodal address, assuming that sufficient PHI is provide to categorize the patient. In one embodiment, resources get "tagged" with appropriate, relevant nodal addresses. In some embodiments, nodal addresses are fungible over time to stay current with scientific/medical advances.

As explained above, when personal health information (PHI) is initially provided for or by a patient a patient of interest, the PHI may not include sufficient information to determine attributes for all of the predetermined variables in a refined nodal address; however, the PHI may include sufficient information to determine attributes for at least a minimum subset of treatment relevant variables. A provisional nodal address can be assigned to the patient of interest based on the attributes for at least the minimum subset of treatment relevant variables. This provisional nodal address can be used to provide relevant treatment information for the patient of interest and to compare treatment of the patient of interest with treatment of similar patients even though values are not known for all the predetermined variables associated with a refined nodal address. The provisional nodal address can include incomplete or absent attributes for one or more of treatment relevant variables not in the minimum subset of treatment relevant variables. The minimum subset of treatment relevant variables may be a specified subset of treatment relevant variables with assigned attributes. As explained above, which treatment relevant variables are included in the minimum subset of treatment relevant variables may depend on at least some of the treatment relevant variables, e.g., a cancer type, a cancer stage, and/or a treatment intent.

As described above, a refined nodal address can embody at least a minimum number subset of treatment relevant variables with assigned attributes and at least a minimum subset of prognosis or outcome relevant variables with assigned attributes. The minimum subset of treatment relevant variables may be a specified subset of treatment relevant variables with assigned attributes and the minimum subset of prognosis or outcome relevant variables with assigned attributes may be a specified subset of prognosis or outcome relevant variables.

As described above, the COTA module 220 can assign attributes for the some or all of the preselected variables based on the initial PHI received for a patient. In some embodiments, the COTA module 220 can determine that attributes have been assigned for at least a minimum subset of treatment relevant variables, but that attributes have been assigned a less than a minimum subset of prognosis or outcome relevant variables. In response to determining that attributes have been assigned for at least a minimum subset of treatment relevant variables but for a less than a minimum subset of prognosis or outcome relevant variables, the COTA module 220 can assign a provisional nodal address to the patient based on the attributes assigned to the minimum subset of treatment relevant variables from the database 240. In some embodiments, the provisional nodal address can includes one or more treatment relevant preselected variables with unassigned attributes. In some embodiments, the provisional nodal address assigned to the patient was previously generated based on personal health information from another patient. In some embodiments, the provisional nodal address is newly generated based on assigned attributes for the patient, and then the newly generated the provisional nodal address is assigned to the patient.

Each provisional nodal address and/or refined nodal address may be associated with predetermined treatment plan information (e.g., one or more bundles of predetermined patient care services). As explained above, in some embodiments, only one provisional nodal address and/or only one refined nodal address is associated with particular predetermined treatment plan information. In other embodiments, more than one refined nodal address is associated with particular predetermined treatment plan information. Where the predetermined treatment plan information includes one or more bundles of predetermined patient care services, each bundle may also be associated with one or more provisional nodal addresses or one or more refined nodal addresses. The predetermined treatment plan information (e.g., the services in each bundle of predetermined patient care services) may be determined by one or more medical professionals, a hospital, a group, a payer (e.g., an insurance company, etc.) to optimize patient care and/or cost. In one example, a bundle may indicate a number of imaging scans, a drug or choice of drugs, a schedule of when to administer the drugs, an operation or procedure, a number and frequency of follow up visits, etc. The bundling of patient care services may be particularly useful for risk contracting. For example, each bundle corresponding to a provisional or refined nodal address (associated with a particular disease) may have a predetermined cost allowing a user (e.g., doctor, patient, etc.) to choose an appropriate bundle. The cost may be determined or negotiated based on historical data associated with that particular disease or refined or provisional nodal address.

As described above, challenges in value-based models for payment for health services include the difficulty in determining an accurate expected outcome for a patient that takes into account non-care related variables that can affect clinical outcome for the particular patient, and difficulties in determining an accurate estimate of expected cost of treatment for a patient. By incorporating or embodying information regarding all variables relevant to treatment and prognosis, the refined nodal address can be used to reliably estimate a prognosis-related outcome for a patient. The COTA module generates reliable prognosis related outcome information and estimated cost information for a refined nodal address using previously acquired information regarding a prognosis based or outcome based cohort (group of people treated as a group) that is grouped based on one or more refined nodal addresses assigned to the patients in the group at a particular point in disease progression. Analysis of prior data from this cohort provides an estimated outcome associated with the refined nodal address and estimated costs at different points in treatment associated with the refined nodal address. In some embodiments, statistical analysis of the prior outcomes for the group is done dynamically when needed. In some embodiments, the statistical analysis can be performed when new relevant information regarding a patient in the group is obtained or when a new patient is added to the group. In some embodiments, statistical analysis of the prior outcomes for the group is conducted periodically and stored, or is conducted on demand. When or how often the statistical analysis is conducted may be different for different outcomes.

Advantageously, in some embodiments, the predetermined treatment plan information (e.g., the bundling of services) provides cost certainty to an insurance company and/or hospital for a particular disease. This may also reduce the cost of processing and maintaining records. Additionally, medical professionals will know ahead of time the predetermined course of treatment, which provides incentives to physicians to obtain better outcomes at lower costs.

In one embodiment, the COTA module 220 can retrieve the predetermined treatment plan information associated with the respective provisional nodal address or refined nodal address from the database 240. The COTA module 220 can transmit the predetermined treatment plan (e.g., information regarding bundles of predetermined care services) to a healthcare provider of the patient of interest. As an example, a healthcare provider can execute an instance of the COTA module 220 on a user computing device 210. The COTA module 220 can render a GUI 250 on the user computing device 210 for the healthcare provider. The computing system 205 can transmit the predetermined treatment plan information (e.g., information regarding the bundles of predetermined care services) to the healthcare provider using the COTA module 220. The predetermined treatment plan information can be rendered on the GUI 250 on the user computing device 210 for the healthcare provider. Alternatively, or additionally, the predetermined treatment plan information can be provided as one or more transmitted documents, as one or more documents for download, as one or more document provided as an attachment to an electronic communication, or in any other suitable format or by any other suitable method.

In some embodiments, the COTA module 220 can receive updated and/or new PHI for patients over time. The COTA module 220 can update the attributes assigned to the preselected variables based on the updated and/or new PHI for the patients. Based on the updated attributes assigned to the preselected variables, the COTA module 220 can assign a new or different provisional nodal address or to a new or different refined nodal address to a patient. In some embodiments, the new or different provisional nodal address or the new or different refined nodal address was previously generated. In some embodiments, the new or different provisional nodal address or the new or different refined nodal address is newly generated based on the updated attributes assigned to the preselected variables. In one embodiment, the predetermined treatment plan information (e.g., the one or more bundles of predetermined patient care services) associated with a provisional nodal address or with a refined nodal address can be updated or changed. In some embodiments, each time predetermined treatment plan information (e.g., information regarding the one or more bundles of predetermined patient care services) associated with a refined nodal address or a provisional nodal address is updated or changed, the COTA module 220 can automatically transmit information regarding the updated or changed predetermined treatment plan information to health care providers for patients currently assigned the refined or provisional nodal address associated with the updated or changed bundles of one or more predetermined patient care services.

In some embodiments, the predetermined variables to be included in a provisional nodal address or in a refined nodal address change, e.g., due to changes in understanding regarding variables relevant to the disease. For example, a group of experts may determine based on their own experience and/or developments reported in papers or publications that that new or different variables should be included in the treatment relevant variables or in the prognosis or outcome relevant variables. In such a case, patients may be reassigned a new current revised refined nodal address or a new current revised provisional nodal address based on the new set of predetermined variables. In some embodiments, the revised refined nodal address or the revised provisional nodal address is only employed on a going forward basis and revised nodal addresses are not assigned for past points in time for a patient. In some embodiments, the system or method maintains a mapping of how the prior nodal addresses relate to the revised nodal addresses to enable analysis based on historical patient data that included the prior nodal addresses. In other embodiments, the system may reevaluate historical patient data and assign revised nodal addresses corresponding to past or outdated medical information for a patient or patients.

Figure 4A:
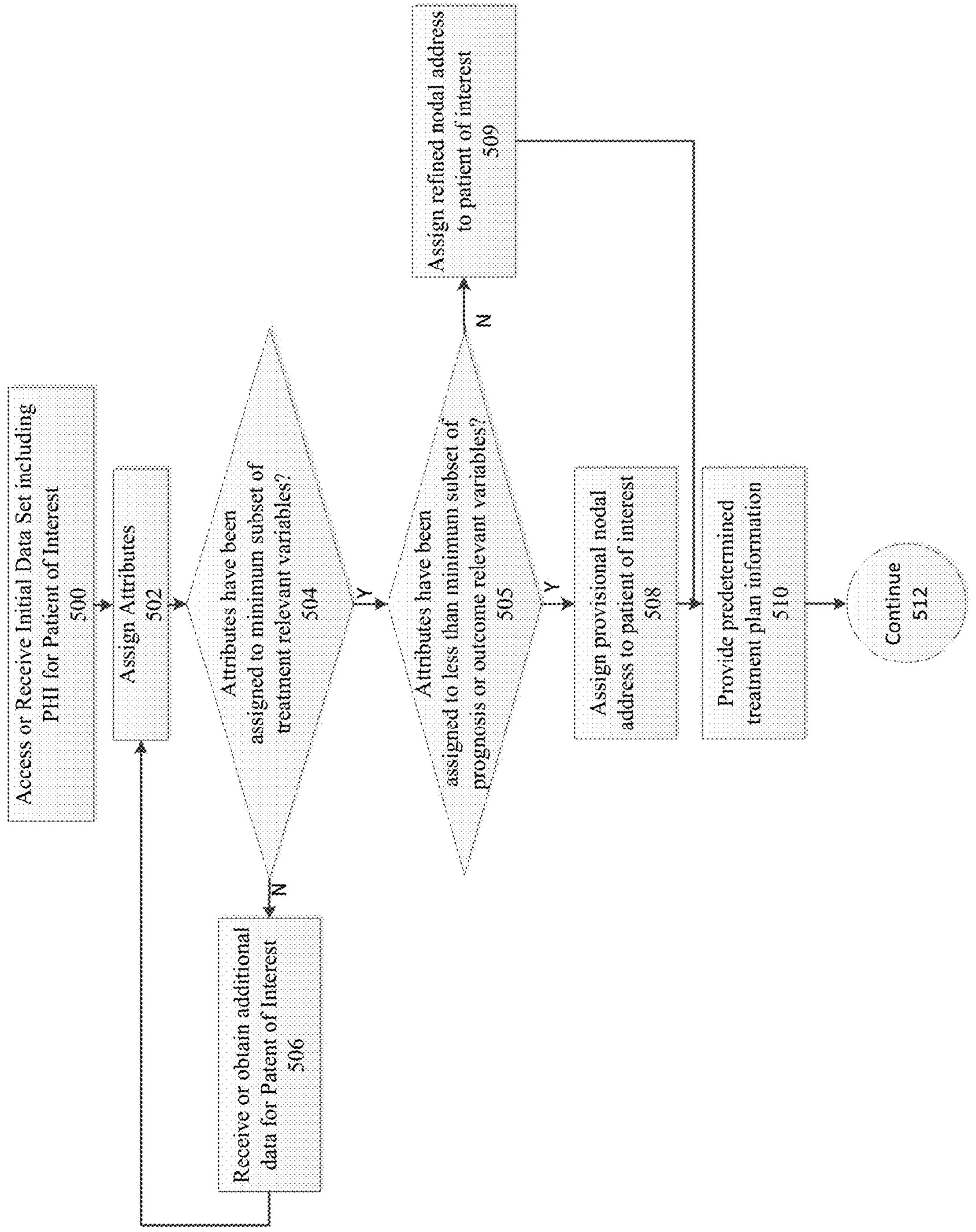
FIG. 4A is a flowchart schematically illustrating a method of assigned a provisional nodal address and/or a refined nodal address to a patient of interest and providing predetermined treatment plan information based on the assigned provisional or refined nodal address in accordance with some embodiments.

FIG. 4A is a flowchart illustrating an exemplary process executed by the COTA module 220 in accordance with an exemplary embodiment. In operation 500, the COTA module 220 accesses or receives an initial data set, which may be described as a first data set, including PHI for a patient of interest. The initial data set includes PHI associated with the patient of interest at a first time or over a first period of time. The PHI can include information associated with phenotypic characteristics of the patient. In some embodiments, the COTA module 220 accesses or receives the initial data set stored in a database 240*a*, 240*b*. In some embodiments, at least some of the initial data set is transmitted from a user computing device 210 being operated by a patient, health care/medical care provider, or insurance company. In operation 502, the COTA module 220 assigns attributes for at least some of a set of preselected variables using the PHI in the initial data set for the patient of interest. In some embodiments, the COTA module 220 can retrieve the preselected variables for a specified disease or group of diseases from the database 240 or a different database. In some embodiments, the COTA module 220 employs a graphical user interface that guides entry of at least some data in the initial data set. In some embodiments, the set of preselected variables can include a set of treatment relevant variables and a set of prognosis or outcome relevant variables. In operation 504, the COTA module 220 can determine whether attributes have been assigned to at least a minimum subset of the set of treatment relevant variables. In some embodiments, the COTA module 220 employs a graphical user interface that guides entry of at least some data for the minimum subset of the treatment relevant variables. In some embodiments, entry of data for one or more of the minimum set of treatment relevant variables (e.g., a cancer type, a cancer stage, and/or a treatment intent) may determine which variables are included in others of the minimum set of treatment relevant variables as explained above and below. In some embodiments, the method includes operation 505, in which the COTA module 220 determines whether attributes have been assigned to at least a minimum subset of the set of prognosis or outcome relevant variables. In some embodiments, operation 504 and operation 505 may be combined in one operation.

An identification or definition of the minimum subset of treatment relevant variables and minimum subset of prognosis or outcome relevant variables can be predefined, and can be stored in a database. In some embodiments, which variables are included in the minimum subset of treatment relevant variables may depend on values of one or more of the treatment relevant variables. For example, in cancer, which variables are included in the minimum subset of treatment relevant variable may depend, at least in part, on the cancer type, cancer stage, and/or treatment intent. In some embodiments, the system or methods may rely on stored identifications of different variables included in minimum subsets of treatment relevant variables for different cancer types, cancer stages, treatment intents or combinations of the aforementioned.

In some embodiments, an identification or definition of the minimum set of treatment relevant variables may be determined, at least in part, based on current medical knowledge. In some embodiments, an identification or definition of the minimum set of treatment relevant variables may be determined, at least in part, by one or more medical professionals.

In some embodiments, if it is determined that attributes have not been assigned to the minimum subset of the treatment relevant variables needed to make a treatment decision in operation 504, the method proceeds to operation 506, and the COTA module 220 waits to receive, access, or obtain further data including PHI for the patient of interest to assign further attributes for the minimum subset of treatment relevant variables. In some embodiments, in operation 506, the COTA module 220 can check to see if there is any new or updated information associated with the PHI of the patient. In some embodiments the COTA module 220 receives the new or updated information associated with the PHI of the patient. In some embodiments, the new or updated information is pushed to the COTA module. In some embodiments the new or updated information associated with the PHI of the patient is pulled by the COTA module. In some embodiments, if attributes have been assigned to less than the minimum subset of treatment relevant variables in operation 504, the system or method may provide a notification or information to a user of the system (e.g., a health care provider or payer) that insufficient information was provided to assign a provisional nodal address.

In some embodiments, where it is determined that attributes have been assigned to at least the minimum subset of the treatment relevant variables in operation 504, the method proceeds straight to operation 508 in which a provisional nodal address is assigned to the patient of interest. In other embodiments, where it is determined that attributes have been assigned to at least the minimum subset of the treatment relevant variables in operation 504, the method further determines whether attributes have been assigned to less than a minimum subset of the prognosis or outcome relevant variables in operation 505. Where attributes have been assigned to at least the minimum subset of the treatment relevant variables in operation 504 and have been assigned to less than the minimum subset of prognosis or outcome relevant variables in 504, the method proceeds to operation 508 in which a provisional nodal address based on the treatment relevant variables is assigned to the patient of interest.

In some embodiments, the provisional nodal address was previously generated based specific attributes assigned to the preselected variables for another patient. The previously generated provisional nodal address can be stored in the database 240. The COTA module 220 can query the database 240 using the assigned attributes to the minimum subset of treatment relevant variables to retrieve the provisional nodal address. In some embodiments, the provisional nodal address is newly generated based on the specific attributes assigned to the preselected variables. In some embodiments, the provisional nodal address includes an indication that one or more of the treatment relevant preselected variables have not yet been assigned and/or are missing. Where initial information regarding a patient is provided to the COTA module at or shortly after diagnosis, the initial information provided will often include sufficient information to assign attributes to at least the minimum subset of the treatment relevant variables, but not include sufficient information to assign attributes to at least the minimum subset of the prognosis or outcome related variables, resulting in a provisional nodal address being assigned to the patient based on the initial information in operation 508.

The provisional nodal address can be associated with predetermined treatment plan information (e.g., information regarding one or more bundles of predetermined patient care services). The COTA module 220 can retrieve information regarding the predetermined treatment plan information (e.g. information regarding one or more bundles of predetermined patient care services) from the database 240 based on the assigned provisional nodal address. In operation 510, the COTA module 220 can transmit and/or provide the predetermined treatment plan information associated with the one or more bundles of patient care services to a health care provider of the patient of interest. As an example, the COTA module 220 can transmit the predetermined treatment plan information (e.g., information regarding the one or more bundles of predetermined patient care services) to a health care provider of the patient of interest operating a user computing device 210 executing an instance of the COTA module 220.

In the event that the initial data set includes information sufficient to assign attributes to a minimum subset of the treatment relevant variables and to assign attributes to at least the minimum subset of the prognosis or outcome relevant variables, a refined nodal address is assigned to the patient of interest in operation 509 in accordance with some embodiments. Specifically, where attributes have been assigned to at least the minimum subset of treatment relevant variables in operation 504 and attributes have been assigned to at least the minimum subset of the prognosis or outcome based variables in 505, a refined nodal address may be assigned to the patient of interest 509 without provisional nodal address being assigned in some embodiments. The refined nodal address—like the provisional nodal addresses—can be associated with predetermined treatment plan information (e.g., information regarding one or more bundles of predetermined patient care services). After assignment of the refined nodal address 509, the COTA module 220 can provide and/or transmit predefined treatment plan information (e.g., information regarding one or more bundles of predetermined patient care services) associated with the refined nodal address assigned to the patient of interest in operation 510. In such embodiments, the predetermined treatment plan information 510 can be provided based on the refined nodal address assigned to the patient of interest.

Figure 4B:
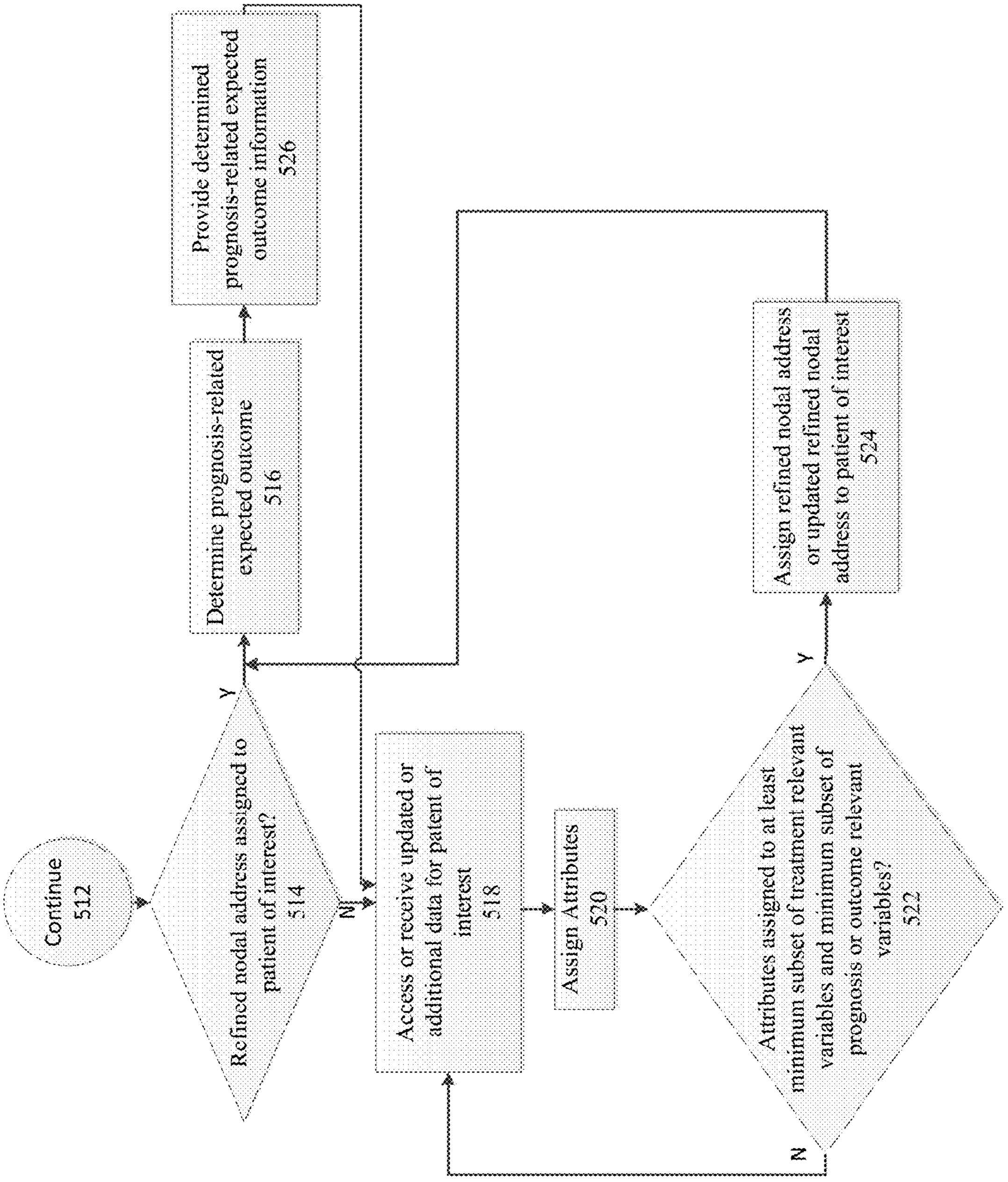
FIG. 4B is a flowchart schematically illustrating a method including accessing or receiving updated or additional data for the patient of interest and assigning a refined nodal address or updating an assigned refined nodal address to the patient of interest, determining a prognosis-related expected outcome based on the refined nodal address, and providing the determined prognosis-related outcome information for the patient of interest in accordance with some embodiments.

After the predetermined treatment plan information is provided in operation 510, the method continues 512 to the flow chart depicted in FIG. 4B. In operation 514, if a refined nodal address has been assigned to the patient of interest, the method proceeds to determining a prognosis-related expected outcome for the patient of interest based on the refined nodal address assigned to the patient of interest in operation 516. In some embodiments, the determined prognosis-related expected outcome information may be provided to a health care provider of the patient of interest, to a health care payer of the patient of interest, and/or to the patient of interest based in operation 526.

In operation 518, the COTA module 220 accesses or receives new or updated information associated with the PHI of the patient of interest. For example, the system may access or receive a second set of data including updated and/or additional personal health information associated with the patient of interest at a second time or over a second period of time later than the first time or first period of time corresponding to the initial data In some embodiments the COTA module 220 receives the new or updated information associated with the PHI of the patient. In some embodiments, the new or updated information is pushed to the COTA module. In some embodiments, the new or updated information associated with the PHI of the patient is pulled by the COTA module. In response to or after accessing and/or receiving, new or updated information association with the PHI for the patient of interest in operation 518, the process can proceed to operation 520 in which the COTA module 220 assigns attributes for the preselected variables based on the new or updated PHI. It can be appreciated that the COTA module 220 can change attributes already assigned to preselected variables and/or assign attributes to preselected variables which were previously unassigned in operation 502 of FIG. 4A. If attributes have not been assigned to at least the minimum subset of treatment relevant variables and the minimum subset of the prognosis or outcome relevant variables in operation 522, the method proceeds again to accessing or receiving updated or additional data for the patient of interest in operation 518.

If attributes have been assigned to at least the minimum subset of treatment relevant variables and the minimum subset of the prognosis or outcome relevant variables in operation 522, the method proceeds to assigning a refined nodal address to the patient of interest in operation 524, and determining a prognosis-related expected outcome for the patient of interest based on the refined nodal address in operation 526. In some embodiments, information regarding the prognosis-related expected outcome is provided to or displayed for a health care provider of the patient of interest or a health care payer for the patient of interest in operation 526.

In some embodiments, the method continues with, the COTA module 220 accessing or receiving new or updated personal health information for the patient of interest in operation 518. It can be appreciated that each time the COTA module 220 accesses, retrieves, or receives updated or new data associated with the PHI of the patient, the COTA module 220 can assign updated or new attributes for the preselected variables, and a new or updated refined nodal address can be assigned to the patient of interest in operation 524 based on the updated or new attributes assigned to the preselected variables. In some embodiments, an updated prognosis-related expected outcome will be determined based on the new or updated refined nodal address in operation 516. In some embodiments, the determined updated prognosis-related output information may be provided to a health care provider of the patient of interest. In some embodiments, this updating of the attributes and the refined nodal address continues throughout treatment of the patient or throughout the life of the patient. In some embodiments, in response to failing to access, receive, or retrieve any new or updated PHI data for the patient, the COTA module 220 can end the process. In some embodiments, the COTA module checks for, accesses, or is provided with any available additional data periodically or on a schedule. In some embodiments, the COTA module conducts additional iterations of updating the refined nodal address based on updated or additional data, periodically, according to a schedule, or whenever additional data is accessed or received for the patient of interest.

In one embodiment, the initial information associated with the PHI for the patient, received, accessed, or retrieved by the COTA module 220 can be PHI for the patient at a first point in time and subsequently received, accessed, or retrieved new or updated information associated with PHI for the patient can be PHI for the patient at a second point in time later than the first point in time. The subsequently received, accessed, or retrieved new or updated information associated with PHI for the patient can be progression of a disease such as cancer with which the patient of interest is diagnosed.

In one embodiment, the initial information associated with the PHI for the patient, received, accessed, or retrieved by the COTA module 220 can be associated with an initial diagnosis for the patient and subsequently received, accessed, or retrieved new or updated information associated with PHI for the patient can be associated with subsequent diagnosis information.

It can be appreciated that each time the COTA module 220 accesses, retrieves, or receives, updated or new information associated with the PHI of the patient, the COTA module 220 can assign updated or new attributes for the preselected variables, and an updated provisional nodal address can be assigned to the patient of interest (if a treatment decision at point of care has not been made and if a refined nodal address has not be assigned to the patient) or a refined nodal address or an updated refined nodal address based on the updated or new attributes assigned to the preselected variables can be assigned to the patient of interest. Further, new predetermined treatment plan information or a new prognosis-related expected outcome can be provided to the health care provider of the patient of interest or to a health care payer for the patient of interest based on the updated provisional nodal address or new or updated refined nodal address assigned to the patient of interest. It can be appreciated that each new or updated refined or provisional address assigned to the patient can be previously generated for specific attributes assigned to the treatment relevant variables and/or prognosis or outcome variables.

As noted above, the refined nodal address can be used to determine a prognosis-related expected outcome with respect to occurrence of a defined end point event for a patient diagnosed with a disease in operation 516. In operation 516 of FIG. 4B, the determined prognosis-related expected outcome for the patient of interest may be obtained from a statistical analysis of prior prognosis-related outcomes for patients in a prognosis or outcome based group of patients who were assigned the same refined nodal address as that assigned to the patient of interest at a corresponding point in disease progression, or at a corresponding point in both treatment and disease progression, as that of the patient of interest for the relevant analysis. For example, the system or method may have access to historical patient data for a prognosis or outcome based group of patients. In some embodiments, each patient in the prognosis or outcome based group of patients is or was assigned the same refined nodal address as that assigned to the patient of interest at a corresponding point in disease progression as that of the patient of interest for the relevant analysis. In other embodiments, at least some, but not all of the patients in the prognosis or outcome based group of patients are or were assigned the same refined nodal address as that assigned to the patient of interest at the corresponding point in disease progression as that for the relevant analysis.

The relevant point in disease progression or disease progression and treatment at which a patient is or was assigned a refined nodal address for outcome-based analysis depends on the particular goal or type of the analysis. For example, as noted above, if interested in an expected time for a patient of interest to progress from start of second line therapy to start of the third line therapy, the relevant refined nodal address would be the refined nodal address of the patient of interest at the start of second line therapy. Similarly, for an outcome or prognosis based group of patients whose historical data would be analyzed to address this question, in some embodiments, each patient in the outcome or prognosis based group of patients would have had the same refined nodal address as that of the patient of interest at the start of that respective patient's second line therapy.

In some embodiments, when determining risk adjustments, the method or system would use a group of patients who were or are all assigned the same refined nodal address as that assigned to the patient of interest as a corresponding point in disease progression, or in both treatment and disease progression, as the patient of interest. In some embodiments, the group of patients may include more than one refined nodal address where the differences in the refined nodal addresses would not significantly impact the risk adjustment analysis. In some embodiments, statistical analysis of historical prognosis-related outcomes for the prognosis or outcome based group of patients who were assigned the same refined nodal address as that of the patient of interest at particular point in disease progression can be used to provide an expected prognosis-related outcome for a patient of interest assigned the refined nodal address at the particular point in disease progression. Similarly, a statistical analysis of historical cost data at a particular point in treatment for the prognosis or outcome based group of patients who were assigned a refined nodal address at a particular point in treatment and disease progression can provide information regarding an expected cost at the corresponding particular point in treatment for a patient of interest assigned the same refined nodal address at the corresponding particular point in treatment and disease progression. In some embodiments, statistical analysis for prior outcomes is performed dynamically when needed. In some embodiments, statistical analysis for a prior outcome associated with patients who were assigned a particular refined nodal address can be stored. In some embodiments, the statistical analysis can be performed periodically, at different intervals, or on demand.

As described above, in one embodiment, the initial information associated with the PHI for the patient, received, accessed, or retrieved by the COTA module 220 can be PHI for the patient at a first point in time or for a first period of time and subsequently received, accessed, or retrieved new or updated information associated with PHI for the patient can be PHI for the patient at a second point in time or second period of time later than the first point in time or first period of time. The subsequently received, accessed, or retrieved new or updated information associated with PHI for the patient can include information regarding progression of a disease such as cancer with which the patient is diagnosed.

In one embodiment, the initial information associated with the PHI for the patient, received, accessed, or retrieved by the COTA module 220 can be associated with an initial diagnosis for the patient and subsequently received, accessed, or retrieved new or updated information associated with PHI for the patient can include with subsequent diagnosis information.

In some embodiments, a method further includes comparing one or more outcomes for the patient of interest to one or more one or more historical outcomes for patients in a prognosis or outcome based group who were assigned the same refined nodal address as that assigned to the patient of interest at diagnosis or at progression to determine if the one or more outcomes for the patient of interest are trending away from a standard for the prognosis or outcome based group. In some embodiments, where it is determined that one or more outcomes for the patient of interest are trending away from the standard for the prognosis or outcome based group, the method also includes sending an alert to a health care provider or health payer of the patient of interest including information regarding the one or more outcomes that are trending away from the standard.

In some embodiments, the COTA module 220 can measure a behavioral variance for each medical care provider for each patient for the prognosis or outcome based group by comparing differences between one medical care provider and another medical care provider(s), in treating, testing, following-up, complying with prescribed medicines, and/or cost for each patient in the patient population assigned the refined nodal address in accordance with some embodiments. Biological variance between patients is removed because any two patients who were assigned the same refined nodal address at the same point in disease progression had the same relevant biological attributes by definition. Therefore any differences in the outcome of these patients at a given point in time can be attributed to the way they are being treated. If the system or method is used to compare doctor Y, who is treating patients who were or are assigned refined nodal address A and doctor Z who is also treating patients who were or are assigned nodal address A, the patients treated by doctor Y may have statistically different clinical outcomes than the patients treated by doctor Z despite the same expected prognosis for both groups due to the common refined nodal address. Differences in outcome between one medical care provider and another (in treating, testing, following up, complying with prescription medicines) are used to identify necessary care that is absent and the presence of unnecessary care contributing to differences between healthcare providers. Alerts may be provided to a medical provider who is deviating from the standard to enable the medical provider to self-correct by providing necessary care that was previously absent and/or by reducing unnecessary care to reach the standard. In some embodiments, the COTA module 220 can identify necessary care absent and/or unnecessary care being provided contributing to the measured behavioral variance for at least one of the medical care providers. In accordance with some embodiments, because patients at the same refined nodal address are grouped, like patients can be compared to like patients with respect to treatment, outcome and costs. For example, by comparing both costs and outcomes across patients that were each assigned the same refined nodal address, the system can be used to identify a particular patient whose treatment costs were much higher than the group, but whose outcomes were not better than the group. The system could send an alert to a payer of medical care of the particular patient whose treatment costs were high that it may be possible to achieve the same outcome at lower cost.

Figure 4C:
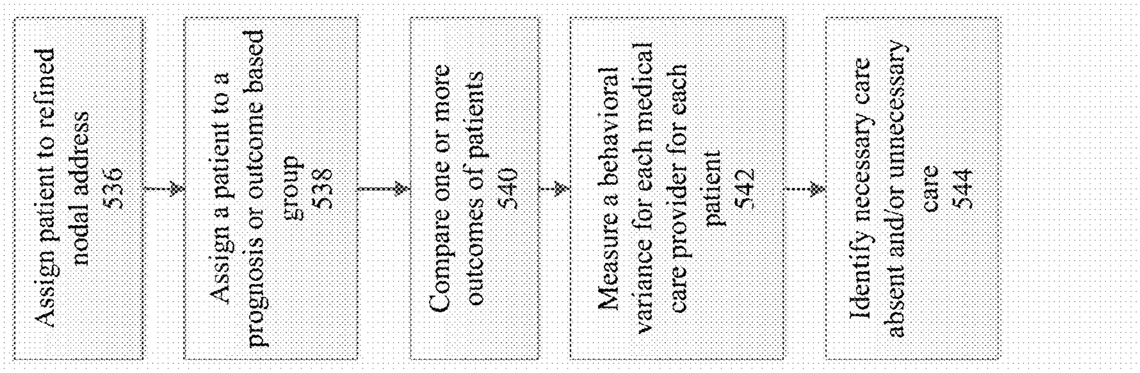
FIG. 4C is a flowchart illustrating a method including measuring a behavioral variance for each medical care provider for each patient and identifying necessary care absent and/or unnecessary care provided in accordance with some embodiments.

FIG. 4C is a flow chart of a method for identifying necessary care absent/and or unnecessary care provided by a medical care provider in accordance with some embodiments. The patient of interest is assigned to a nodal address in operation 536 as described above. The patient of interest is then assigned to a prognosis or outcome based group based on the refined nodal address assigned to the patient of interest in operation 538 as described above. A behavioral variance for each of a plurality of medical care providers for a plurality of patients assigned to the prognosis or outcome based group is measured in operation 542. Based on the behavioral variance, necessary care absent and/or unnecessary care being provided that contributes to the measured behavioral variance for at least one of the medical care providers is identified in operation 544.

Figure 4E:
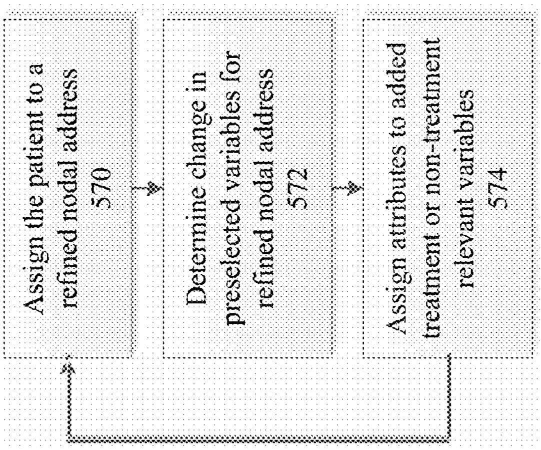
FIG. 4E is a flowchart illustrating a method including determining a change in preselected variables included in a refined nodal address and assigning a revised refined nodal address to the patient of interest based on the change in preselected in accordance with some embodiments.
Figure 4D:
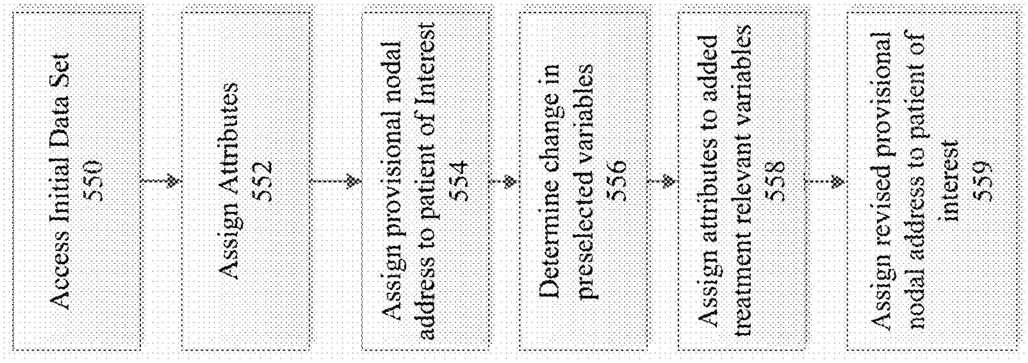
FIG. 4D is a flowchart illustrating a method including determining a change in preselected variables included in a provisional nodal address and assigning a revised provisional nodal address to the patient of interest based on the change in preselected variables in accordance with some embodiments.

FIG. 4D is a flowchart illustrating a process performed by the COTA module 220 in accordance with an exemplary embodiment. As described above, a provisional nodal address can embody values or attributes of treatment relevant preselected variables. As noted above, in some embodiments, the preselected variables are defined by or identified by a group of experts in the relevant field(s) (e.g., oncologists with more than 5, 10, 15, 20, 30, etc. years of experience). In some embodiments, the preselected variables are defined or identified based, at least in part, on information regarding current medical knowledge and treatment and/or information from experts in the relevant field. In some embodiments, definition or identification of the preselected variables to be included in the provisional nodal addresses and refined nodal addresses are updated based on new information regarding current medical knowledge and treatment and/or updated information from experts in the field on a going forward basis. In some embodiments, the definition or identification of the preselected variables is updated on a periodic schedule. In some embodiments, the definition or identification is updated as needed based on newly available information. In some embodiments, the preselected variables can include treatment and prognosis or outcome relevant variables for which attributes are necessary to provide assistance in making treatment and payment decisions.

In operation 550, the COTA module 220 can access an initial data set including PHI for a patient. In operation 552, the COTA module 220 can assign attributes for at least some of a set of preselected variables using the PHI for the patient. The COTA module 220 can retrieve the preselected variables for a specified disease from the database 240. The set of preselected variables can include a set of treatment relevant variables and a set of prognosis or outcome relevant variables.

In operation 554, in response to the COTA module 220 being able to assign attributes to the minimum subset of the set of treatment relevant variables and less than the minimum subset of the prognosis or outcome relevant variables, the COTA module 220 can assign a provisional nodal address to a patient based on the assigned attributes for the set of treatment relevant variables. In operation 556, the COTA module 220 determines that a change in the preselected variables for the particular disease (i.e., cancer) of the patient has occurred, or accesses or receives information that a change in the preselected variables has occurred, before a treatment decision has been made at point of care, or in some embodiments, before a refined nodal address has been assigned. The change can be an addition to or a change in the set of treatment relevant variables or the minimum set of treatment relevant variables for a provisional nodal address. For example, the preselected variables may be updated on a going-forward basis based on new data, new scientific discoveries or new developments in treatment. In some embodiments the update to the preselected variables may be entered through an instance of the COTA module 220 executing on a user computing device 210. In some embodiments, updates to the preselected variables may be made to a database including the preselected variables using another method and information regarding the update is supplied to the COTA module. Alternatively, or in addition, in some embodiments, the COTA module 220 can receive input from various sources updating the preselected variables.

In operation 558, the COTA module 220 can assign attributes for one or more of the treatment relevant variables added to the preselected variables based on the most current information associated with PHI for the patient available to the COTA module 220. In response to assigning attributes for the one or more treatment relevant variables added to the preselected variables, the process can proceed to operation 559, at which point the COTA module 220 can assign a revised provisional nodal address to the patient based on the attributes assigned to the newly added treatment relevant variables if a treatment decision has not yet been made, or in some embodiments, if a refined nodal address has not yet been assigned. It can be appreciated that the COTA module 220 can assign a revised provisional nodal address to the patient if a treatment decision has not yet been made, or in some embodiments, before a refined nodal address has been assigned, each time the preselected treatment relevant variables for provisional nodal addresses are changed. It can be appreciated, the COTA module 220 can generate the revised provisional nodal address prior to assigning the revised provisional nodal address to the patient, if needed. For example, in some embodiments, the revised provisional nodal address may have already been generated for some other patient having the same values for the treatment relevant variables and the previously generated revised provisional nodal address is assigned to the patient of interest.

FIG. 4E is a flowchart illustrating a process performed by the COTA module 220 in accordance with an exemplary embodiment. As described above, a refined nodal address can embody at least a minimum subset of treatment relevant variables and at least a minimum subset of prognosis or outcome relevant variables of the preselected variables. The preselected variables can be defined or selected as described above. The preselected variables can include treatment and prognosis or outcome relevant variables for which attributes are necessary to provide assistance in making treatment and payment decisions.

In operation 570, the COTA module 220 assigns a refined nodal address to the patient of interest based on the assigned attributes for at least the minimum subset of treatment relevant variables and the minimum subset of prognosis or outcome relevant variables as explained above. In operation 572, the COTA module 220 can determine whether a change in the preselected variables for the particular disease (i.e., cancer) of the patient has occurred or can receive or access information regarding a change in the preselected variables included in the refined nodal address. The change can be an addition to the set of treatment relevant variables and/or set of prognosis or outcome relevant variables. The predetermined variables can be updated on a going-forward basis as described above. In operation 574, the COTA module 220 can assign attributes for one or more of the treatment relevant variables or prognosis or outcome relevant variables added to the preselected variables based on the most current information associated with PHI for the patient available to the COTA module 220. In response to assigning attributes for the one or more treatment and/or prognosis or outcome relevant variables added to the preselected variables, the process can return to operation 570, at which point the COTA module 220 can assign a revised refined nodal address to the patient of interest on a going forward basis based on the attributes assigned to the newly added treatment and/or prognosis or outcome relevant variables to the preselected variables. It can be appreciated that in some embodiments, the COTA module 220 can assign a revised refined nodal address to a patient on a going forward basis at diagnosis and at each subsequent progression depending on the start date of the particular analysis and on how attributes of the predetermined variables have changed.

Some personal health information for a patient does not change. Other personal health information for a patient changes over time. In some embodiments, the COTA module groups personal health information by relevant point in time or relevant period of time and assigns a provisional nodal address or a refined nodal address to the grouped information regarding the relevant point in time or relevant period of time. In some embodiments, the provisional nodal address is only employed until a refined nodal address is assigned. After assignment of a refined nodal address, the provisional nodal address is no longer employed and all later points in time or later periods of time with respect to disease progression will be assigned an appropriate refined nodal address.

In some embodiments, grouped personal health information relevant to a different point in time or period in time may be assigned the same refined nodal address or a different refined nodal address depending on the start date of the particular analysis and on how attributes of the predetermined variables have changed. Thus, in some embodiments, the assigned provisional or refined nodal address may be described as a nodal address associated with or assigned to a patient at a point in time or period of time, or a nodal address associated with or assigned to personal health information of the patient at a point in time or a period of time. In some embodiments, a refined nodal address is assigned to a patient, at least, at or shortly after diagnosis and at each subsequent identified disease progression. This grouping of personal health information by relevant point or period of time and assignment of nodal addresses based on the relevant health information at that time facilitates comparison between like patients who each have or had the same values of relevant variables at a relevant corresponding point in each patient's disease progression, even if different refined nodal addresses were or are later assigned to the patients based on values of the variables for the patients changing over time. The relevant corresponding point in disease progression depends on the type of analysis being employed.

In some embodiments, the refined nodal addresses enable clinically relevant groups of patients to be identified for analysis. Analyzing the data records may include tracking (e.g., in real time) clinical outcomes of patients having with the disease. The outcomes may include, for example, delivered dose intensity, therapeutic agents received, dose, dose interval, and dose duration, incidence and severity of toxicity, cost, progression free survival (PFS), overall survival (OS), response rates, etc. The COTA module 220 may compare the tracked outcomes between patients. The COTA module 220 may also determine, based on the tracking, whether a specific doctor associated with a tracked patient is treating the patient in accordance with treatment techniques of other doctors treating other (similar) patients. In one embodiment, the COTA module 220 determines this based on the outcomes of many patients whose similarity is determined based on the provisional nodal address or the refined nodal address assigned to the patient.

In another example, analysis based on refined nodal addresses can provide an expected prognosis-related outcome associated with a refined nodal address, as described above. In some embodiments, this expected prognosis-related outcome for a refined nodal address can be compared with a standard prognosis-related expected outcome that is an average, a median, or other statistically determined value or range for a population having a variety of different relevant biological factors to determine whether a patient assigned the refined nodal address is likely to have an prognosis-related outcome that is better or worse than the standard prognosis-related outcome (e.g., poor, good, average, or better than average).

In an outcomes-based payment model, payers are looking to incentivize favorable outcomes. However, if an expected outcome is not based on all relevant biological factors, but instead based on merely an average of a population having a variety of different relevant biological factors, then a provider could be punished for a patient not achieving the average expected outcome, when the cause of the patient not achieving the expected outcome is due to biological factors and not patient treatment and care. Similarly, a provider could receive a bonus for a better than expected outcome, when the cause of the patient having better than expected results is due to biological factors and not patient treatment and care. When employing analysis based on refined nodal addresses, which includes information regarding all available relevant treatment related variables and all available prognosis or outcome relevant variables, patients are grouped and analyzed to determine a reasonable and accurate expected outcome specific to a patient's combination of biologically relevant variables, so that payers can increase or decrease payment based on achieving or failing to achieve the reasonable and accurate expected outcome tailored to the patient. In some embodiments, a standard outcome based on patients with different values for biologically relevant variables may be employed, and the refined nodal address used to determine the probability that an expected outcome for a patient assigned the refined nodal address would be about the same as the standard outcome, worse than the standard outcome, or better than the standard outcome.

As described above, analysis based on refined nodal addresses can also provide an expected cost of treatment at various points in treatment associated with a refined nodal address. This enables the system/method to provide cost estimates specific to a patient's particular combination of biologically relevant variables that can be used by payers for implementing reasonable bundled payment/episode of care models.

As noted above, some values-based models for reimbursement for health care require determination of a prognosis-related outcome for a patient and/or an expected cost of treatment for the patient over a clinically relevant period. Unfortunately, some conventional systems base an expected outcome solely on billing codes, which may be useful for providing an average expected outcome for a patients with a particular disease, but do not take into account non-care and treatment related differences in prognosis based on biological differences between patients. Such systems have no ability to provide an accurate prognosis for an individual patient with a particular disease, such as breast cancer. For example, one population, such as the population of patients with breast cancer, can be composed of multiple subgroups with different expectations for survival. Those expectations for survival can be correlated with a poor, good, average, or better than average prognosis. If payment were based on a comparison of an individual patient's outcome with the average outcome for all breast cancer patients, this would result in under compensation for all patients whose outcome is worse than average, even those that had a poor prognosis at the outset, and overcompensation for all patients whose outcome is better than average, even those that had a good prognosis. Similarly, such systems have no ability to provide an accurate estimate for the treatment cost required to obtain such a prognosis.

A refined nodal address embodies and summarizes all biological variables related to treatment and prognosis for a patient assigned the refined nodal address. Refined nodal addresses enable grouping of patients by variables relevant to treatment and diagnosis, and corresponding grouping of patients that all have the same risk/prognosis. By analyzing historical data for the appropriate grouping of patients, an expected outcome specific to the patient's treatment and prognosis relevant attributes can be obtained. In some embodiments, patients assigned multiple different refined nodal addresses during the course of the disease having a similar prognosis may be combined into a single prognosis or outcome based group, such as a poor risk, average risk, or good risk grouping. Further, where the historical data regarding the group of patients includes historical cost information, a cost estimate for care over a clinically relevant period can be determined.

By grouping patients based on treatment and prognosis relevant attributes, the refined nodal address enables determination of an accurate and reasonable expectation of prognosis and cost so that payers can increase or decrease payment based on achieved results related to patient care instead of related the patient's own underlying biological factors.

In another embodiment, analyzing the data records may include updating (e.g., in real time) at least some of the data records based on the tracked outcomes. For example, the COTA module 220 may determine that patient ABC had colon cancer, was prescribed and has taken medication XYZ for two years, and is now in remission for the past 3 years. If the COTA module 220 determines this information from the tracking of patient ABC, the module 220 can update the data record associated with patient ABC with this information. Further, the COTA module 220 can receive information regarding costs related to treatment of patient ABC and update records regarding treatment costs for patient ABC over time.

In other embodiments, analyzing the data records includes performing an analysis to determine patient survival rate, such as, e.g., by creating a Kaplan Meier curve. A Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. Other types of analyses are also contemplated. In some embodiments, the data records to be compared may be selected based on the refined nodal addresses assigned to the data record for each patient or assigned to each patient at a given point in time during the course of the disease, limiting the comparison to patients having similar attributes relevant to treatment or prognosis for the particular disease or disorder at the same point in disease progression or treatment.

To facilitate analyzing, the COTA module 220 may also include an analysis tool that may be executed by or accessed via the user computing device 210. This analysis tool may be a user interface that is accessible via a web page, a tab on an existing web page, a software application, an app, etc. The user interfaces as depicted in the figures herein are exemplary. This analysis tool may enable a user to compare, analyze, or further sort the data records.

In some embodiments, the COTA module 220 provides a communication based on the analysis. The communication may be in the form of an alert to a user. In one embodiment, the COTA module 220 may communicate the classified and sorted data records and/or the updated data records to the user computing device 210. For example, the COTA module 220 communicates a table, chart, list, link, etc. that enables the user to access the sorted or updated data records. In another embodiment, the COTA module 220 may transmit advertisements with (e.g., related to) the data records to the user computing device 210. In other embodiments, the COTA module 220 may identify a specific patient as a candidate for a specific treatment or drug. This information may be valuable to, e.g., a pharmaceutical company, a health plan, a managed care consortium, an insurer, etc. The COTA module 220 may transmit the communication to the user computing device 210 or any other entity (e.g., via network 215).

Figure 5:
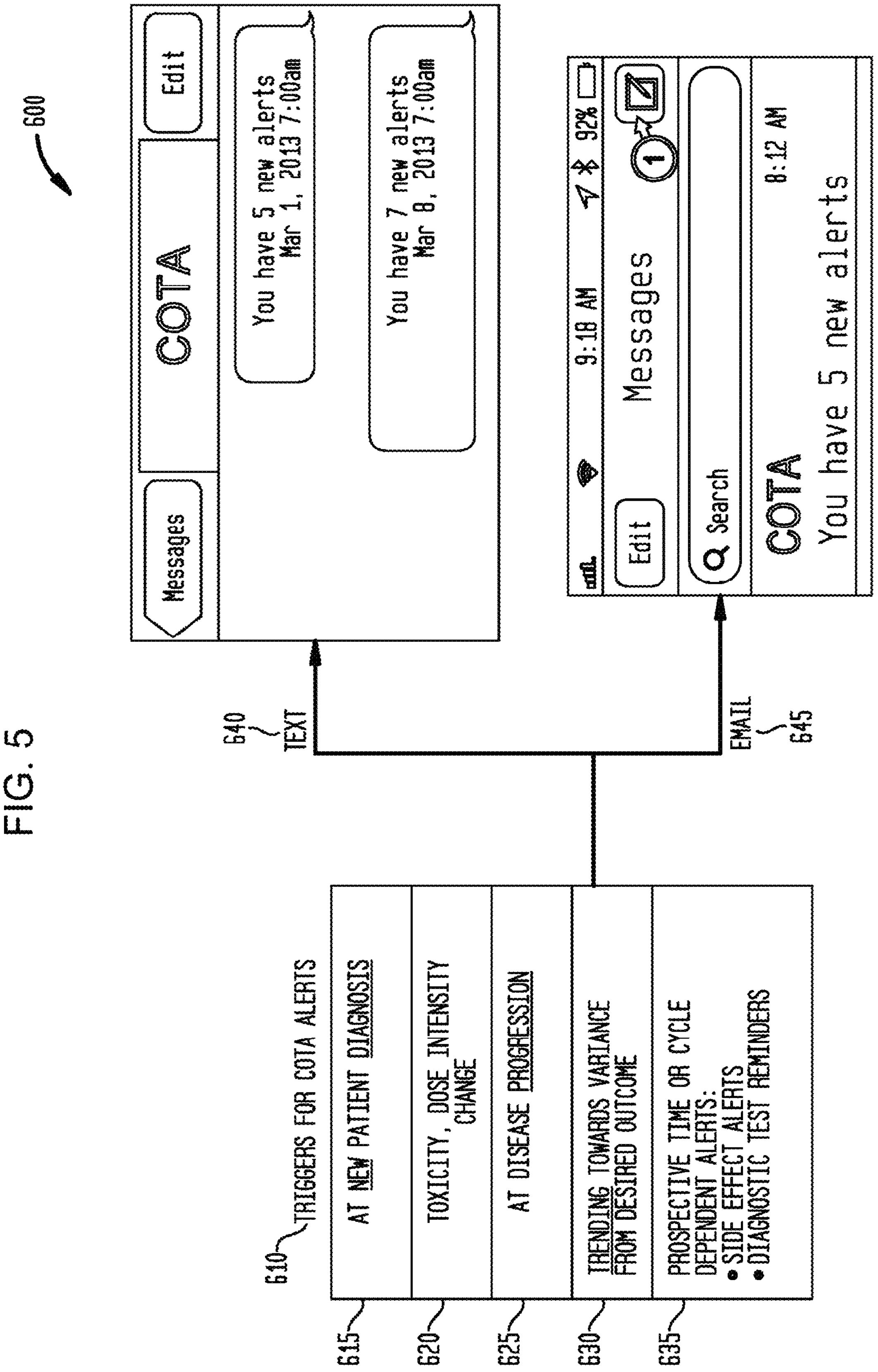
FIG. 5 depicts a flow diagram of the COTA module transmitting alerts in response to triggers in accordance with an embodiment of the present disclosure.

FIG. 5 illustrates a flow diagram 600 of alerts provided by the COTA module 220 in accordance with an embodiment. In one embodiment, physicians or other medical professionals are alerted based on their preferences. These preferences can be set by the medical professional/physician and can include, for example, triggers 610 for the alerts and/or the technique used to provide the alert. As an example, physicians or other medical professionals can set the preferences using the COTA module 220 executed on their respective user computing device 210. A trigger for an alert can include, for example, at new patient diagnosis 615, an update to a diagnosis, a real-time scheduled event, changes to group membership (e.g., a new gene identified which might change grouping, and/or someone leaving the group), toxicity and/or dose intensity change 620, at disease progression 625, administration of a particular drug, trending towards variance from desired outcome 630, and/or prospective time or cycle dependent alerts 635 (e.g., side effect alerts and/or diagnostic test reminders). The alert may include a text message 640 or an email 645 sent to the user computing device 210. Other types of alerts are also contemplated, such as, e.g., a telephone call to the user computing device 210, an update on a web page, a social media update, a message sent using, e.g., Twitter®, Facebook®, or other social media site, adding content to a software library or web page, and/or any other message or communication sent to or accessed by the user computing device 210. Although described above as providing alerts, a trigger can be any action that results in the COTA module 220 performing any other action.

In one embodiment, alerts can also include information regarding, and/or be triggered by a new refined nodal address being assigned to a patient, for example, at progression. Additionally or alternatively, alerts can include information regarding, and/or be triggered by new predetermined treatment plan information for a patient based on either a change in the new or updated provisional or refined nodal address or a change in the predetermined treatment plan information (e.g., information regarding a bundle of one or more patient care services) associated with the provisional or refined nodal address. In some embodiments, the alerts can be triggered by a change in the preselected variables for a particular disease.

Figure 6:
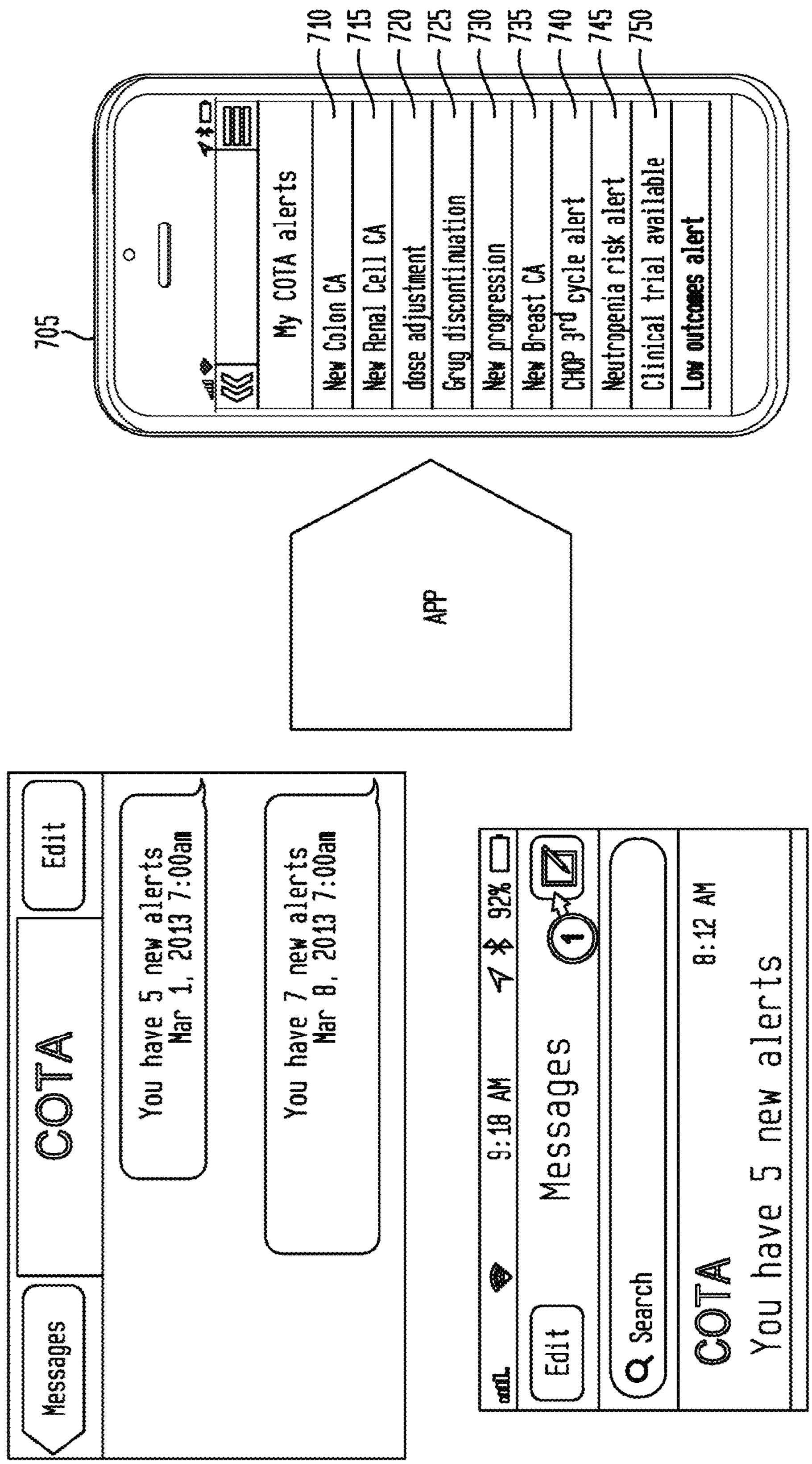
FIG. 6 schematically depicts a mobile device organizing received alerts in accordance with an embodiment of the present disclosure.
Figure 7:
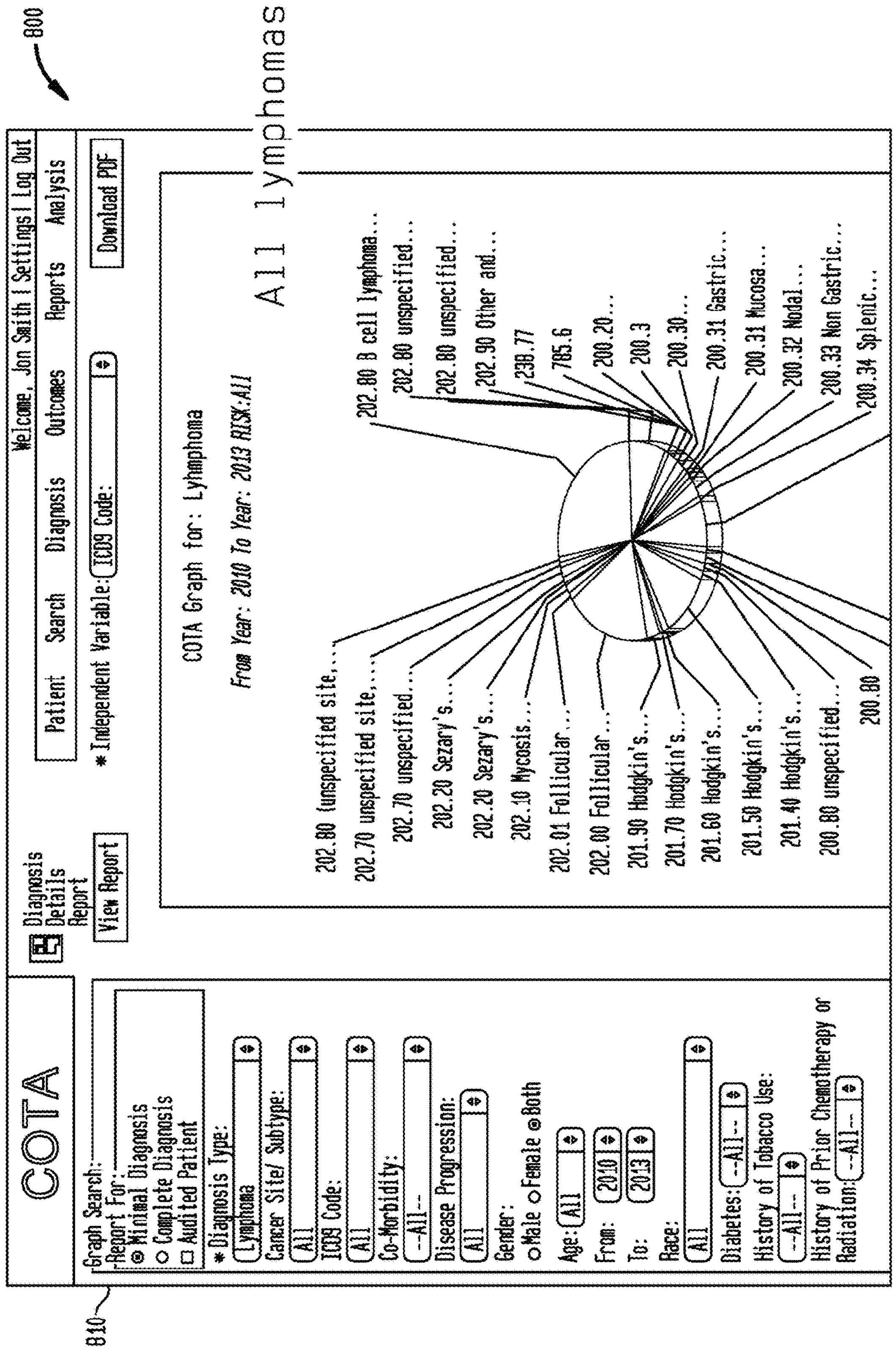
FIG. 7 depicts a graphical representation of incidence of disease by cancer subtype provided by a COTA module in accordance with an embodiment of the present disclosure.

FIG. 6 is a graphical representation illustrating a mobile device 705 (e.g., user computing device 210) organizing alerts received by the device 705 in accordance with one embodiment. As shown in FIG. 7, the COTA alerts received are listed by a title or subject, such as New Colon CA 710, New Renal Cell CA 715, Dose Adjustment 720, Drug Discontinuation 725, New Progression 730, New Breast CA 735, CHOP 3rd cycle alert 740, Neutropenia risk alert 745, and Clinical trial available 750. CHOP is an abbreviated name of a combination of drugs used in chemotherapy, which includes cyclophosphamide (Cytoxan/Neosar), doxorubicin (or Adriamycin), vincristine (Oncovin), and prednisolone, and is used, for example, to treat non-Hodgkin lymphoma.

The COTA module 220 can provide specific disease data sets (e.g., on demand and in real time) including, for instance, incidence of disease (e.g., by a COTA sort), progression free survival by progression status, and/or overall survival. In one embodiment, the COTA module 220 can provide a drug utilization data set, such as data associated with a full or partial therapy, toxicity, and/or a change in therapy.

FIG. 7 shows a graphical representation 800 of incidence of disease by cancer subtype that can be provided by the COTA module 220 in accordance with one embodiment. Here, the COTA graph 800 is for lymphoma from years 2010 to 2013. A user can utilize a graph search input section 810 to narrow the information that is graphed. The graph search input section 810 can include, for example, a selection of what to report for (e.g., minimal diagnosis, complete diagnosis, and/or audited patient, diagnosis type, cancer site/subtype, ICD9 (International Classification of Diseases, Ninth Revision) code, Co-Morbidity, Disease Progression, Gender, Age, Date Range, Race, Diabetes, History of Tobacco Use, History of Prior Chemotherapy or Radiation, etc.).

Figure 8:
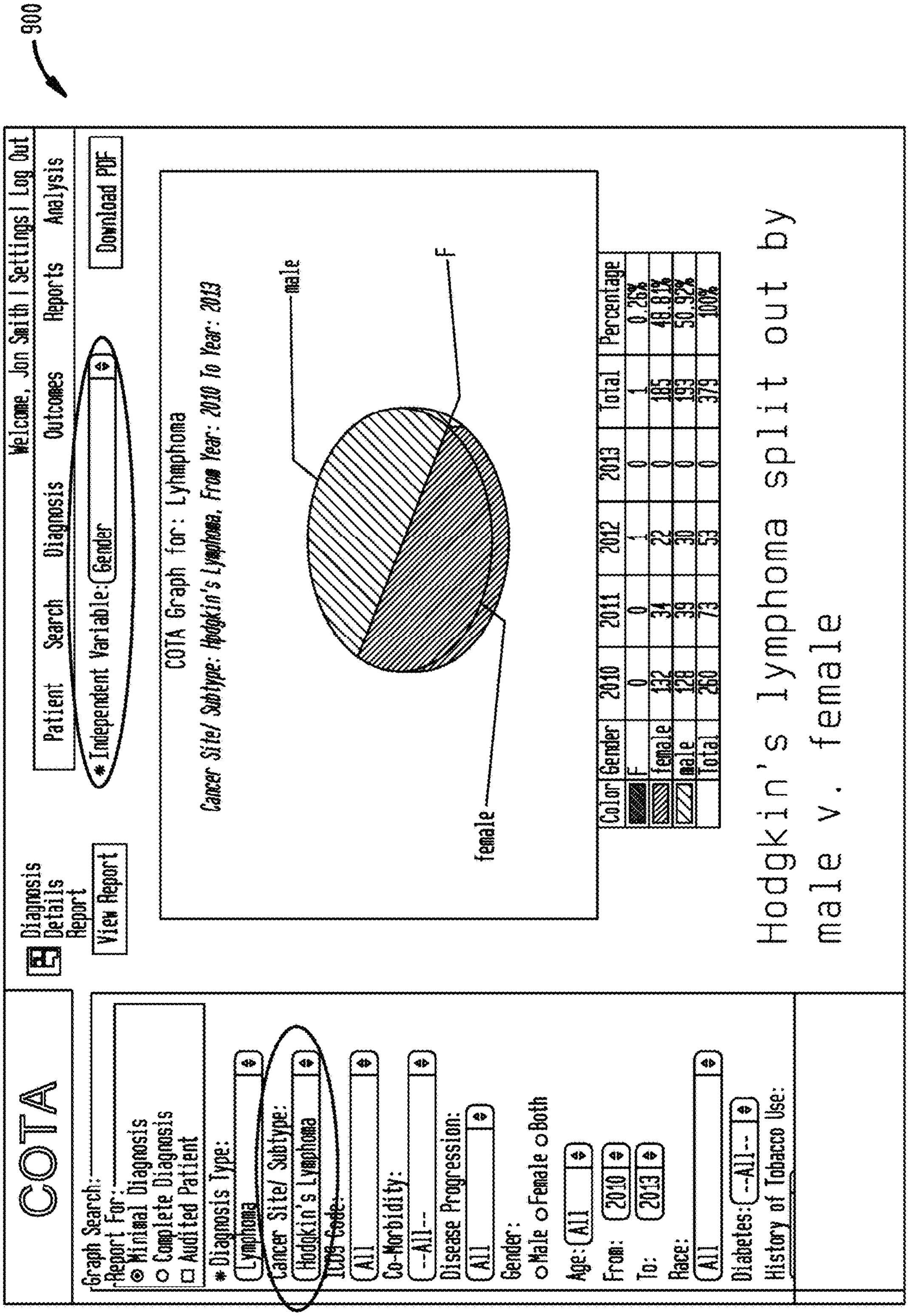
FIG. 8 is a graphical representation of a search refined by variables input into the COTA module in accordance with an embodiment of the present disclosure.
Figure 9:
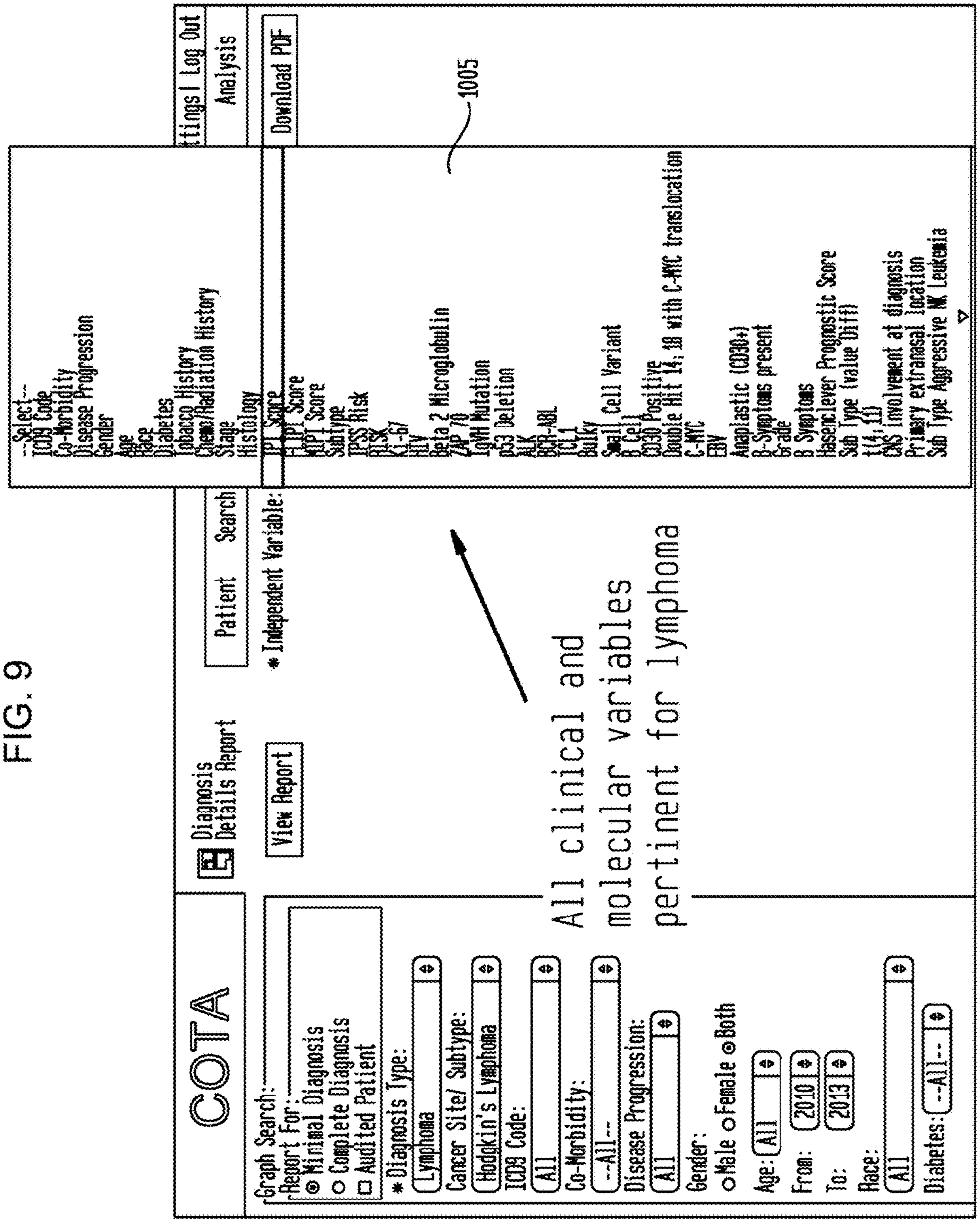
FIG. 9 depicts a graphical user interface including a listing of a plurality of variables pertinent to a particular disease in accordance with an embodiment of the present disclosure.

FIG. 8 shows a graphical representation 900 of a sort based on variables input into the COTA module 220 that can be provided by the COTA module 220 in accordance with one embodiment. The graphical representation 900 shows a COTA graph for Hodgkin's Lymphoma from years 2010-2013 split out by male vs. female. The graphical representation 900 shows statistics 910 of the different patients who had this disease that were graphed in representation 900. FIG. 9 shows an exemplary listing of a plurality of clinical and molecular variables 1005 pertinent to a particular disease (here, variables shown are for lymphoma) in accordance with one embodiment.

Figure 10:
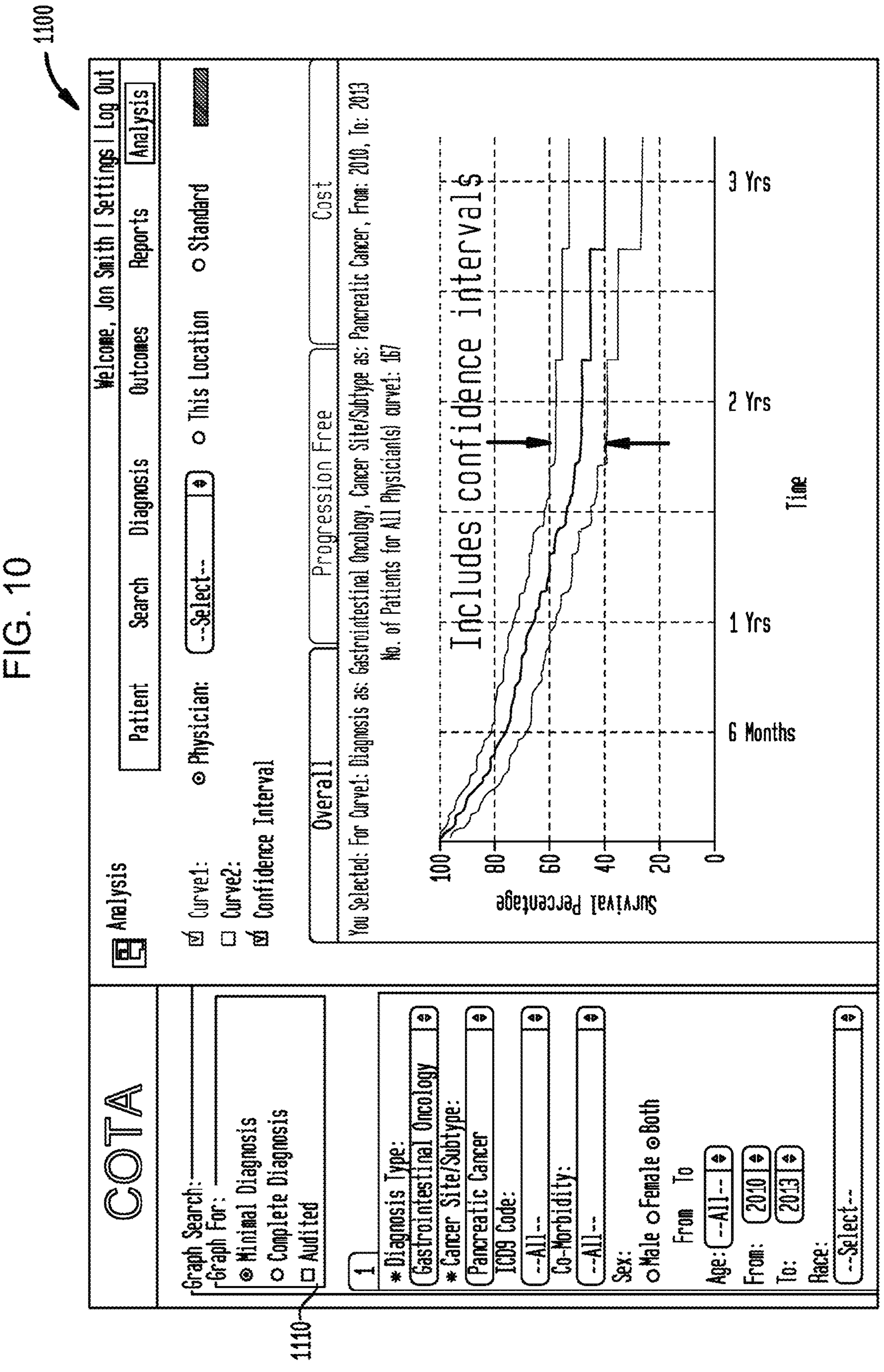
FIG. 10 depicts a graphical user interface including real-time Kaplan Meier curves with confidence intervals for pancreatic cancers in accordance with an embodiment of the present disclosure.

FIG. 10 shows a graphical representation 1100 including real-time Kaplan Meier curves with confidence intervals for pancreatic cancers that can be provided by the COTA module 220 in accordance with one embodiment. As described above, a Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. The user indicates variables for his graph search in graph search input section 1110.

Figure 11:
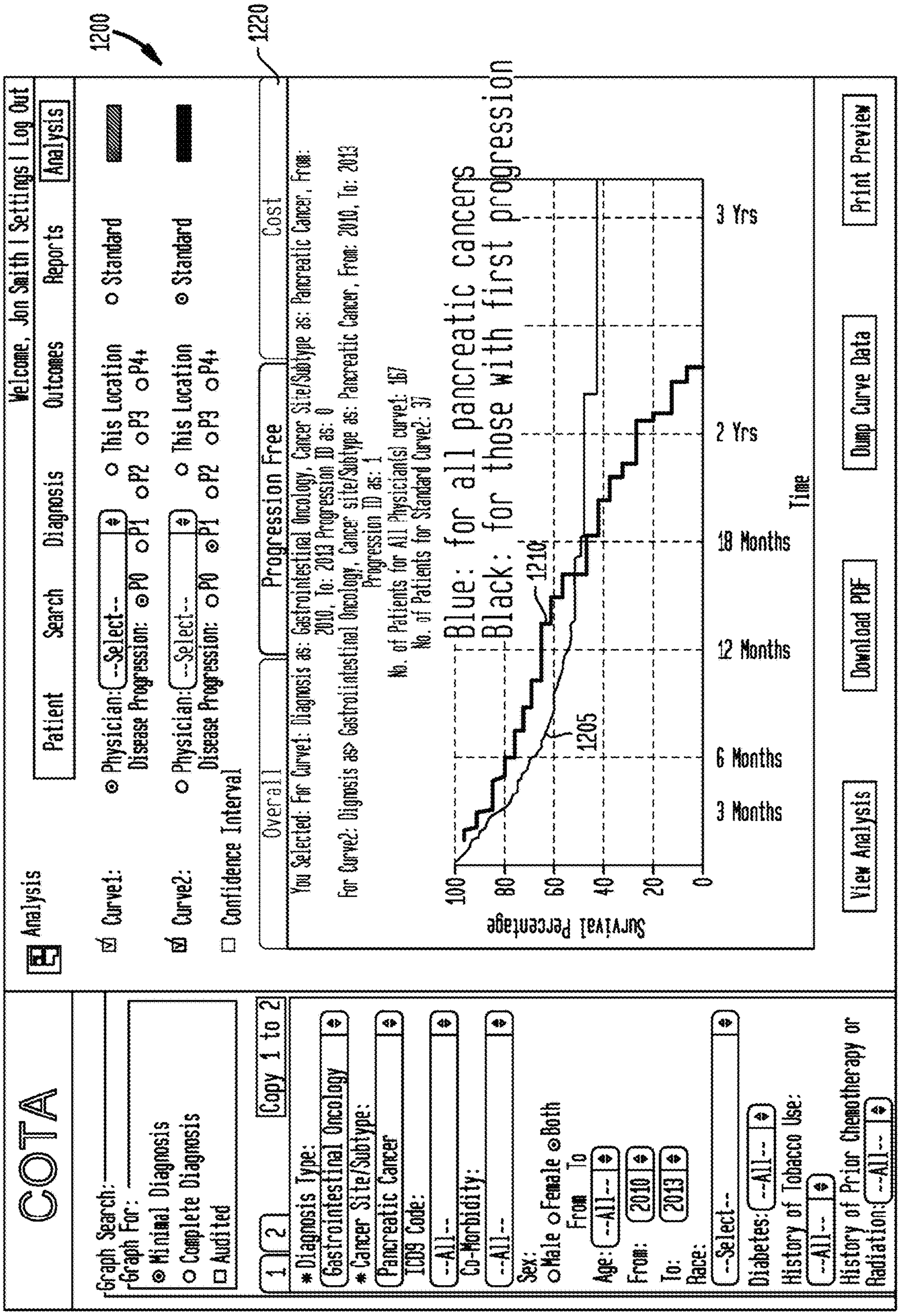
FIG. 11 depicts a graphical user interface including Kaplan Meier curves by disease progression in accordance with an embodiment of the present disclosure.

FIG. 11 is a graphical representation 1200 showing Kaplan Meier curves for disease progression that can be provided by the COTA module 220 in accordance with one embodiment. Line 1205 is for all pancreatic cancers, and bold line 1210 is for those with first progression.

Figure 12:
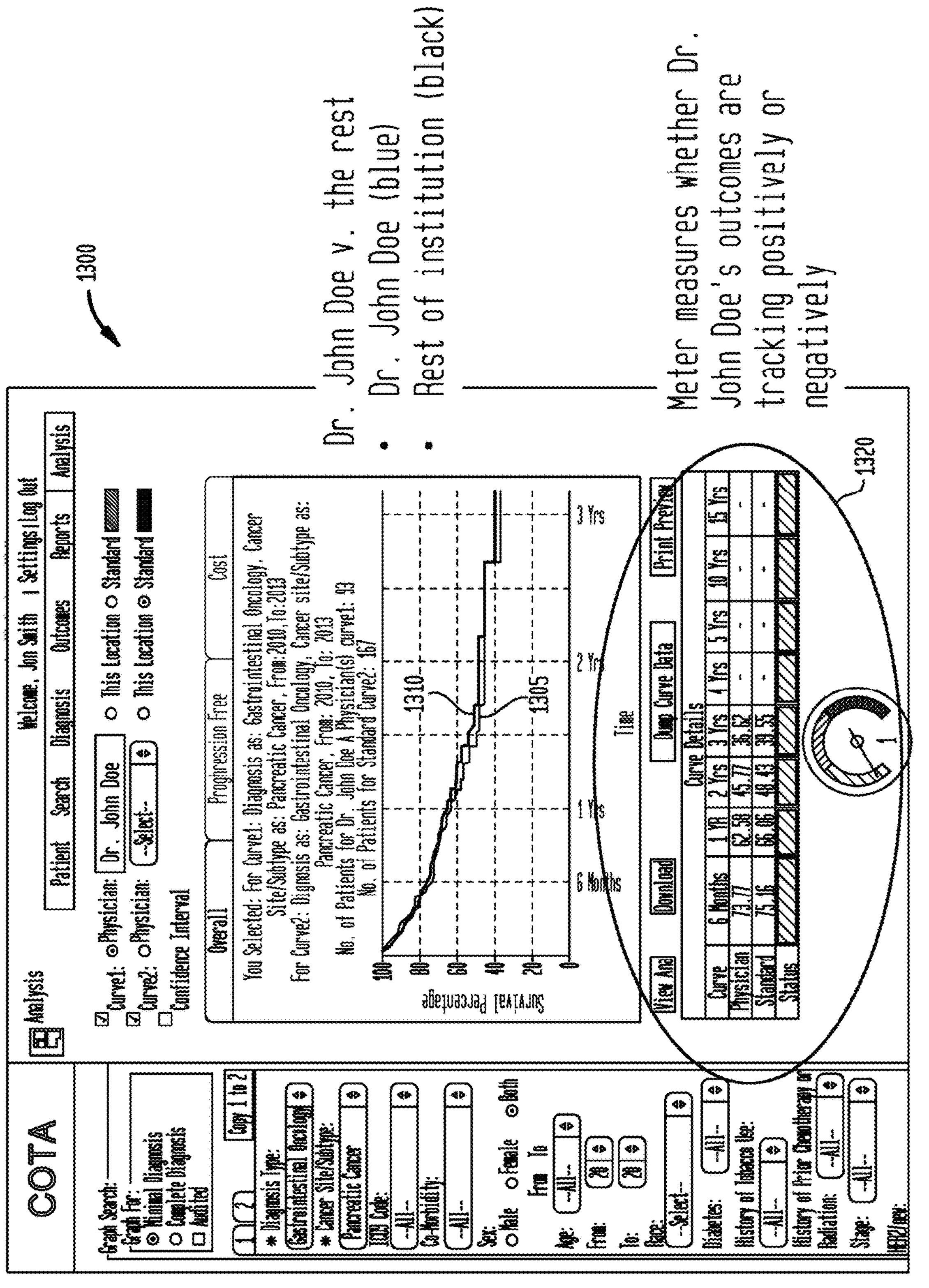
FIG. 12 depicts a graphical user interface including a graphical representation of real-time benchmarking of outcomes between two parties in accordance with an embodiment of the present disclosure.

FIG. 12 is a graphical representation 1300 of real time benchmarking of outcomes between two parties that can be provided by the COTA module 220 in accordance with one embodiment. The graph 1300 includes curve 1305 for outcomes of Dr. John Doe, a physician who treats pancreatic cancer, a curve 1310 for outcomes of the rest of the doctors who treat pancreatic cancer, and a meter 1320 measuring whether Dr. John Doe's outcomes are tracking positively or negatively.

Figure 13:
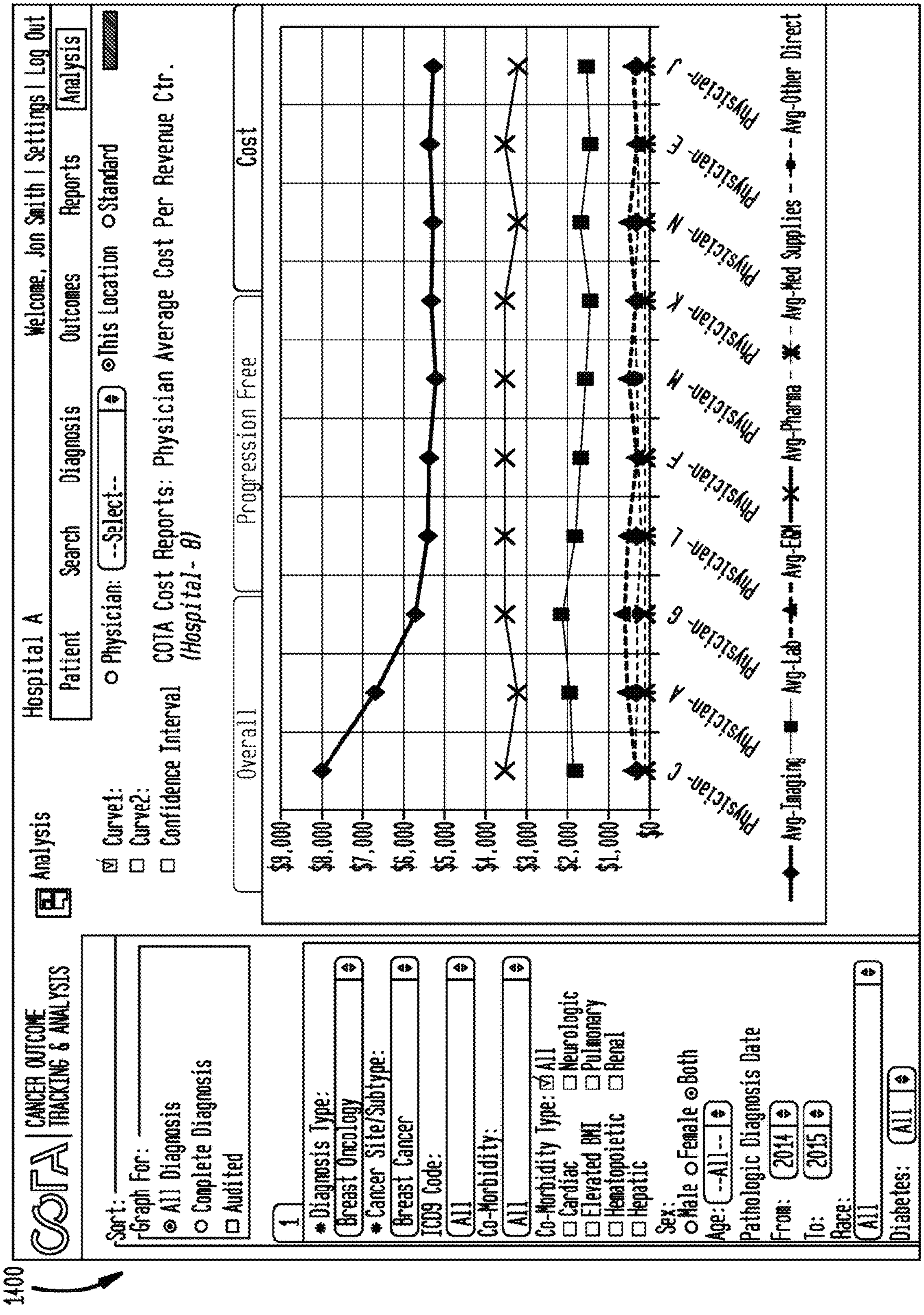
FIG. 13 depicts a graphical user interface including a graphical representation of a cost report showing a plot of outcomes as a function of treating physician based on cost in accordance with an embodiment of the present disclosure.

FIGS. 13-18 relate to measures of outcome. FIG. 13 is a graphical representation of a cost report 1400 associated with (e.g., provided by) the COTA module 220 in accordance with one embodiment. The cost report 1400 may be associated with the cost tab 1220 of FIG. 12. The cost report 1400 can be used, for example, in estimating cost(s) of treatment, capturing knowledge, and/or transforming the knowledge into specific implementations. In one embodiment, the COTA module 220 tracks costs of various treatments, physicians, hospitals, etc. in real time. As shown in FIG. 14, the cost report 1400 illustrates a graph of outcomes including comparison between physician and average cost per revenue center (e.g., hospital). Cost report 1400 may also include other comparisons, such as, e.g., hospital contribution margin in dollars and percent, hospital average revenue and cost (e.g., average revenue per patient, average cost per patient), physician average cost per case (e.g., average cost per case for each physician, weighted average), physician average cost per revenue (e.g., average cost of imaging, lab work, evaluation and management, pharmaceuticals, medical supplies, and other expenses for each physician), etc. In an outcomes-based payment model, payers are looking to incentivize favorable outcomes. By sorting patients using a refined nodal address, which include all available treatment elements and all available progression elements are creating group of patients in which progression expectation is reasonable. In some embodiments, this enables increase or decrease payment from payers based on actually achieved results related to treatment and care, as opposed to increasing or decreasing payment based on the patient's biological attributes that impact prognosis and outcome.

Figure 14A:
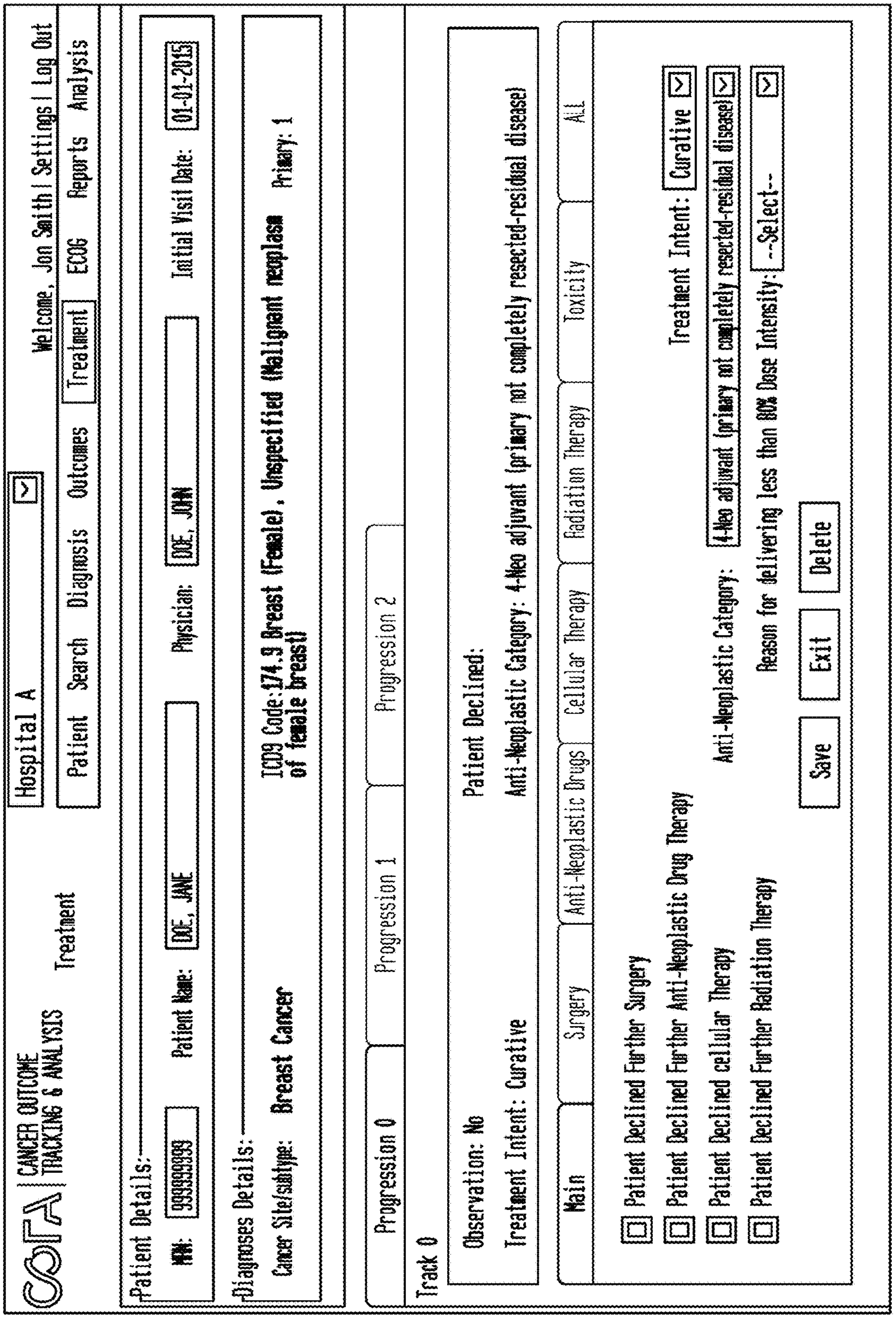
FIGS. 14A and 14B depict a graphical user interface including graphical representations of a treatment interface showing outcomes based on patient decisions affecting treatment in accordance with an embodiment of the present disclosure.
Figure 14B:
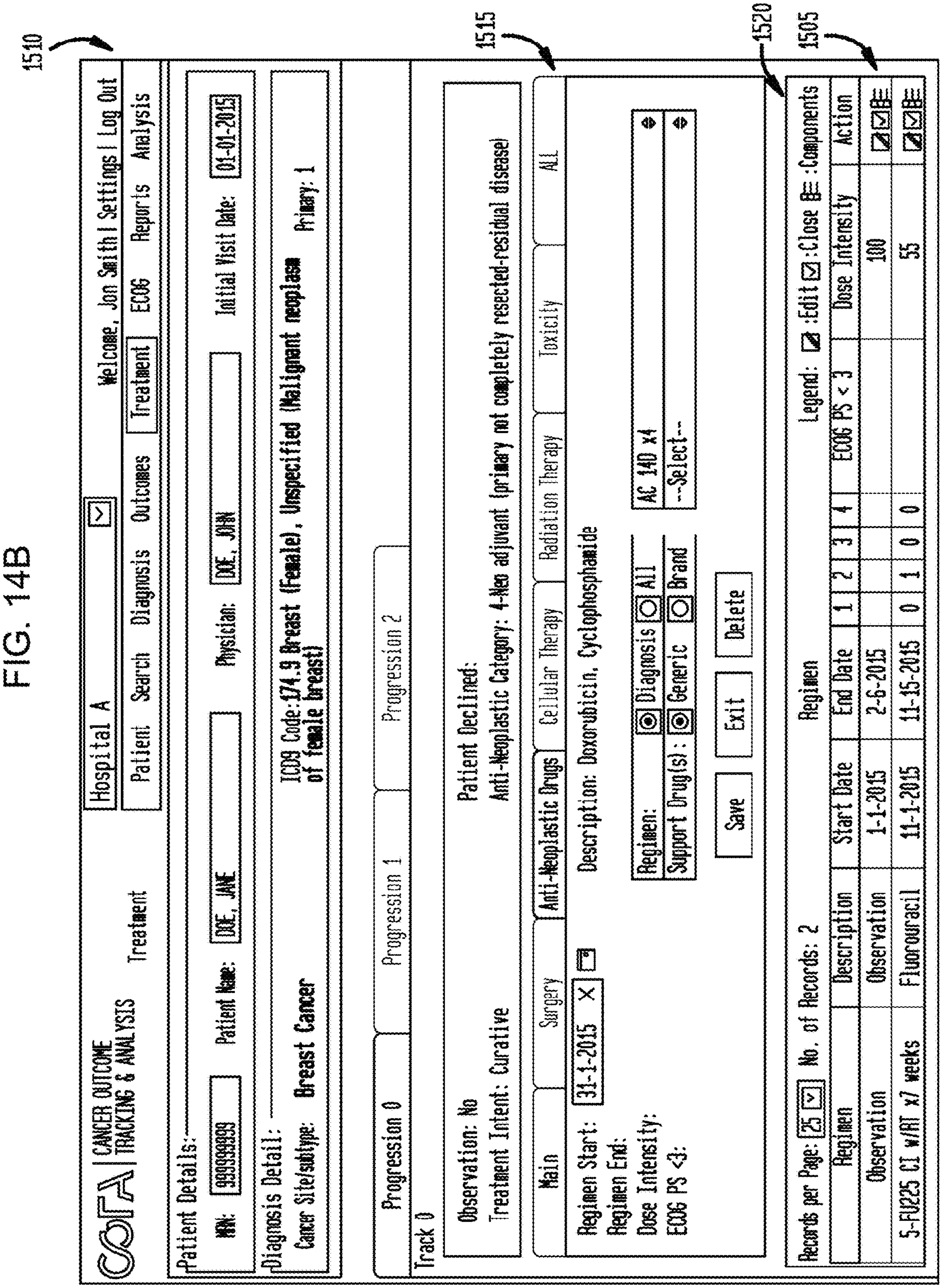

FIGS. 14A and 14B are graphical representations of a treatment interface 1500 associated with (e.g., provided by) the COTA module 220 for facilitating the connection between outcomes and treatments, in accordance with one embodiment. FIGS. 14A and 14 B show outcomes based on patient decisions affecting treatment. As shown in FIG. 14A, the treatment interface 1500 may include a list of the different types of treatment administered to (or declined by) a patient with breast cancer, such as, e.g., surgery, antineoplastic drugs, cellular therapy, radiation therapy, etc. Treatment may be arranged according to a disease progression. For example, drugs in oncology are typically given in cycles, and, in any one cycle, any number of drugs can be given. In one embodiment, a user can select a progression (e.g., represented as progression 0 to progression 4), with progression 0 being after first diagnosis, cycle, and can select drugs in or from multiple categories.

In FIG. 14B, in another embodiment, a treatment interface 1510 may include treatment regimens for one or more therapies, graphically represented on treatment interface 1510 as tabs 1515. Treatment interface 1510 may include fields to indicate a start and end data for the regimen, dose intensity, description of treatment, specific brands of drugs, etc. Treatment regimens may be graphically summarized or represented as a listing of treatments in table 1520. Table 1520 may include action icons 1505 for each treatment. The action icons 1505 may facilitate actions, such as, e.g., editing, closing, viewing components, etc. In one embodiment, the action icons 1505 may be shortcuts to perform complex tasks (e.g., requiring multiple clicks or selections) with a single selection. For example, an icon on the diagnosis line can bring the user to the diagnosis screen.

Figure 15:
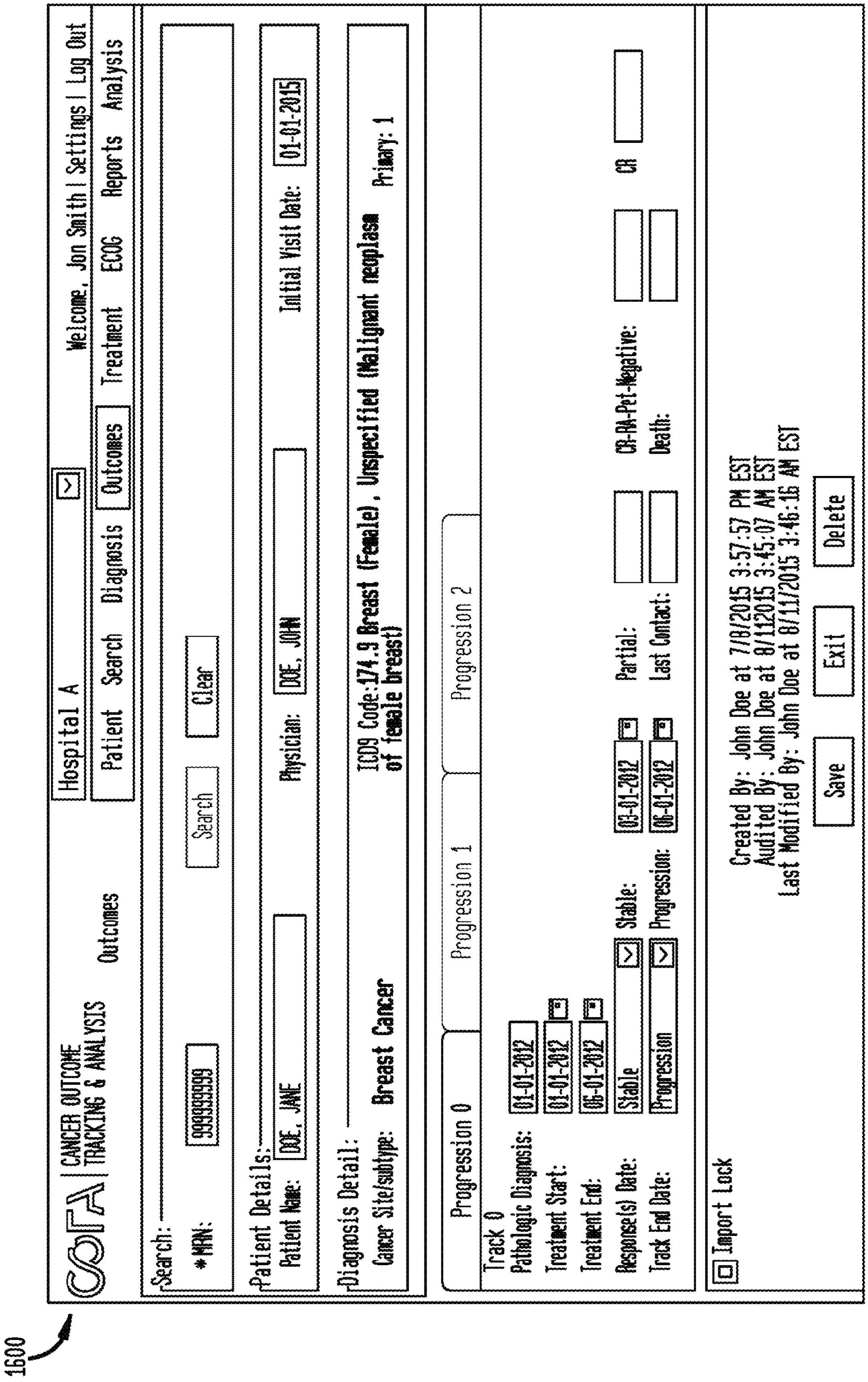
FIG. 15 depicts a graphical user interface including a graphical representation of an outcome screen in accordance with an embodiment of the present disclosure.

FIG. 15 is a graphical representation of an outcome screen 1600 for facilitating outcome tracking in accordance with one embodiment. Outcome screen 1600 may facilitate outcome tracking from, for example, diagnosis (i.e., progression zero), first progression, second progression through fourth progression, with each progression considered a different disease. The outcome screen tab can include (e.g., in one or more drop down menus or other fields) a diagnosis date, a treatment start and end date, a response to treatment (e.g., complete, partial, stable) and date of response, input fields for notes on the response (e.g., the partial field, CR-RA-Pet Negative field, the CR field, etc.), and a track end data, which may include fields for last contact and death. The outcome screen 1600 may also include other fields, such as, e.g., toxicity of a drug treatment, an input area enabling the input of what happened (e.g., discontinued, continued, no change, drug dosage change, and how many times), number of delays, number changes in drug, and/or number reduced. In one embodiment, a user of the COTA module 220 can flag a patient.

Figure 16:
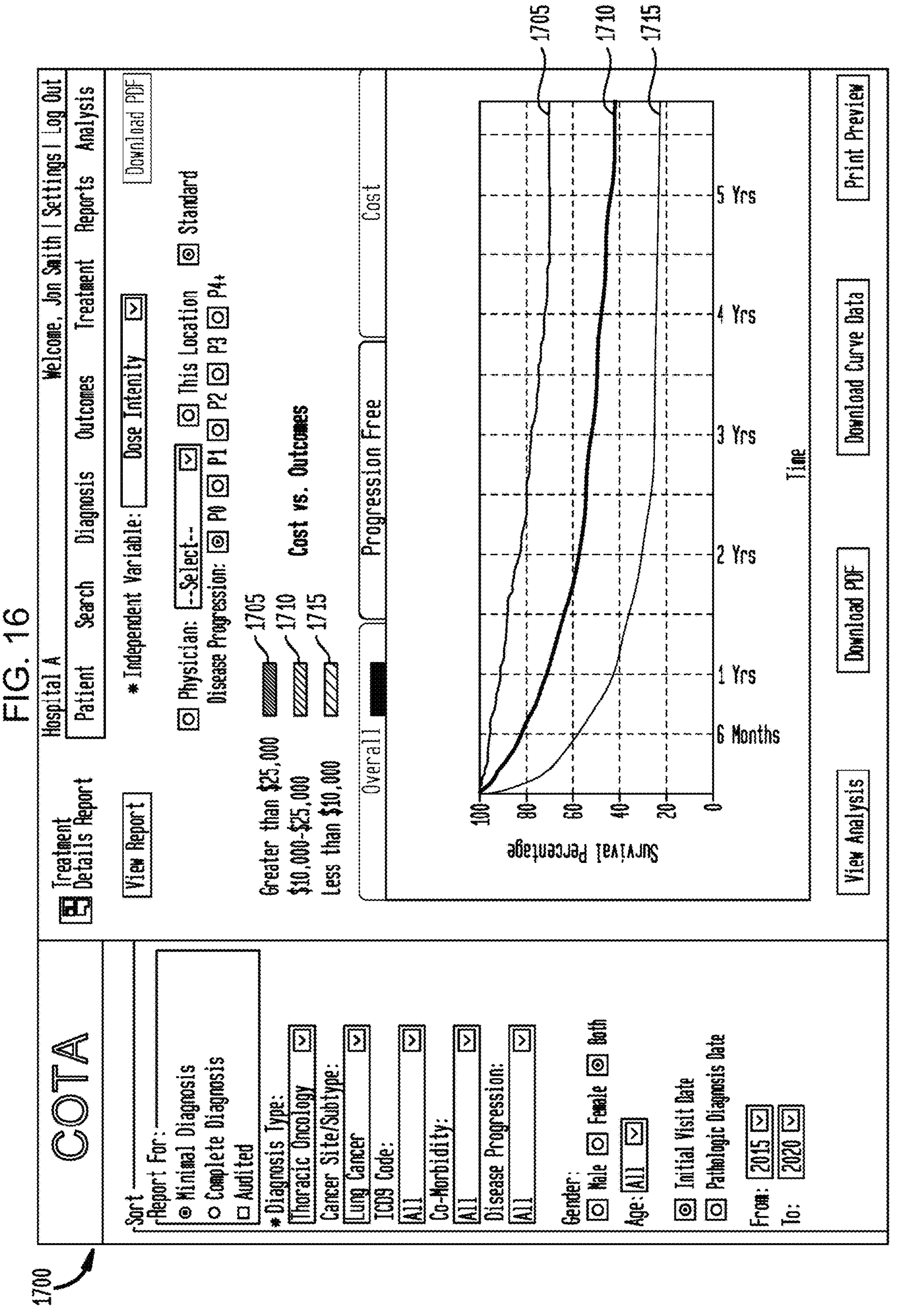
FIG. 16 depicts a graphical user interface including a graphical representation of a treatment details report screen showing a relationship between cost of treatment and outcome, specifically survival, for lung cancers in accordance with an embodiment of the present disclosure.

FIG. 16 is a graphical representation of a treatment details report screen 1700 illustrating a comparison between cost and outcome in accordance with one embodiment. Specifically, the graph in the report shows cost of cost of treatment versus outcome for lung cancers. The curves 1705, 1710, 1715 in the graph are Kaplan Meier survival curves for lung cancer with different ranges of costs expended. The treatment details report screen 1700 correlates cost of care to clinical outcome to optimize value of care. Cost and financial data may be collected and analyzed by hospital, by doctor, etc. over a given time period (e.g., 5 years). The cost and financial data may be represented in one or more ranges of cost. In one embodiment, the ranges of cost include range 1705 for cost greater than $25,000, range 1710 for cost from $10,000 to $25,000, and range 1715 for cost less than $10,000. The higher costs are associated with improved survival over time as shown by the curves 1702. 1710, 1715 for the different cost ranges in the plot. When combined with clinical data, the COTA module 220 may provide cost data for different treatments for a given time period based on different clinical sorts.

Figure 17:
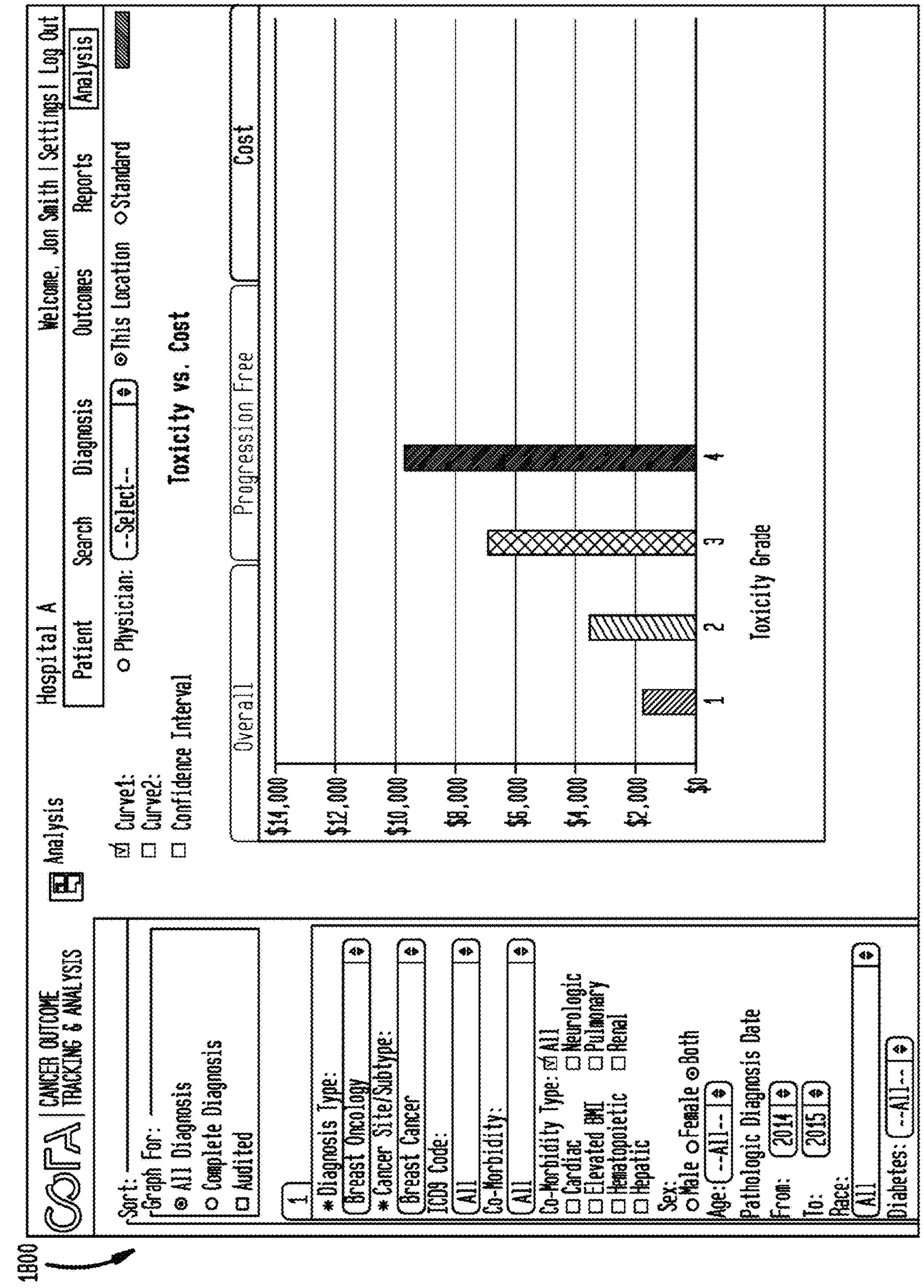
FIG. 17 depicts a graphical user interface including a graphical representation of an analysis screen comparing toxicity and cost in accordance with an embodiment of the present disclosure.

FIG. 17 is a graphical representation of an analysis screen 1800 provided by the COTA module 220 illustrating a comparison between toxicity and cost in accordance with one embodiment. The analysis screen 1800 correlates incidence and severity of toxicity to cost of care and outcomes of care. The analysis screen 1800 includes a bar graph showing grade of toxicity of adjuvant therapy versus cost of treatment for patients with breast cancer. The toxicity may be represented numerically (e.g., in ranges), by standards (e.g., grades), etc. For example, as shown in FIG. 17, toxicity is represented as toxicity grades 1-4 based on the Common Terminology Criteria for Adverse Events (CTCAE) classification. The grade of toxicity is graphically compared with cost. As shown, a higher treatment cost can be associated with increased toxicity and a corresponding decreased quality of time. The analysis screen 1800 may be used to optimize value and efficacy of care, where value is efficacy/cost. In one embodiment, the COTA module 220 attempts to obtain high efficacy and low cost.

Figure 18:
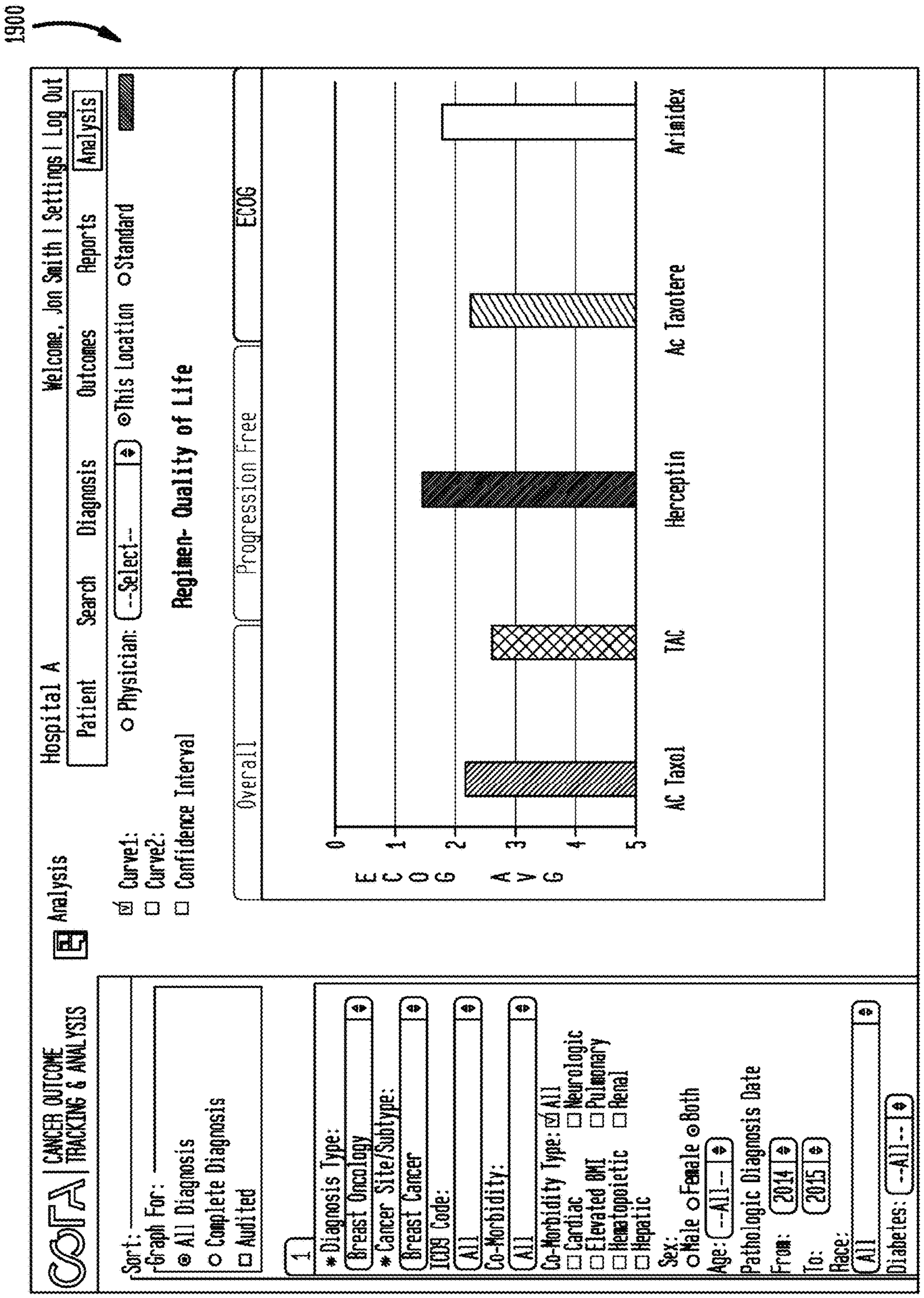
FIG. 18 depicts a graphical user interface including a graphical representation of an analysis screen comparing therapy and quality of life in accordance with an embodiment of the present disclosure.

FIG. 18 is a graphical representation of an analysis screen 1900 provided by the COTA module 220 including a graph comparing quality of life for various adjuvant therapies for breast cancer. The therapy may be represented by treatment drugs in analysis screen 1900. However, other forms of therapy are also contemplated, such as, e.g., surgery, procedures, etc. In one embodiment, the therapy includes an incidence, severity, and toxicity of therapy. Quality of life may be measured based on the average ECOG (Eastern Cooperative Oncology Group) scale, ranging from Grade 0 (i.e., fully active) to Grade 5 (i.e., dead). Quality of life may also be measured using any suitable metric. Analysis screen 1900 may facilitate assessment of how a patient's disease is progressing, how the disease affects the daily living abilities of the patient, and appropriate treatments and prognoses. As shown in the graph depicted, ECOG is highest for Herceptin, followed by Arimidex, AC Taxol, AC taxotere, and TAC.

Figure 19:
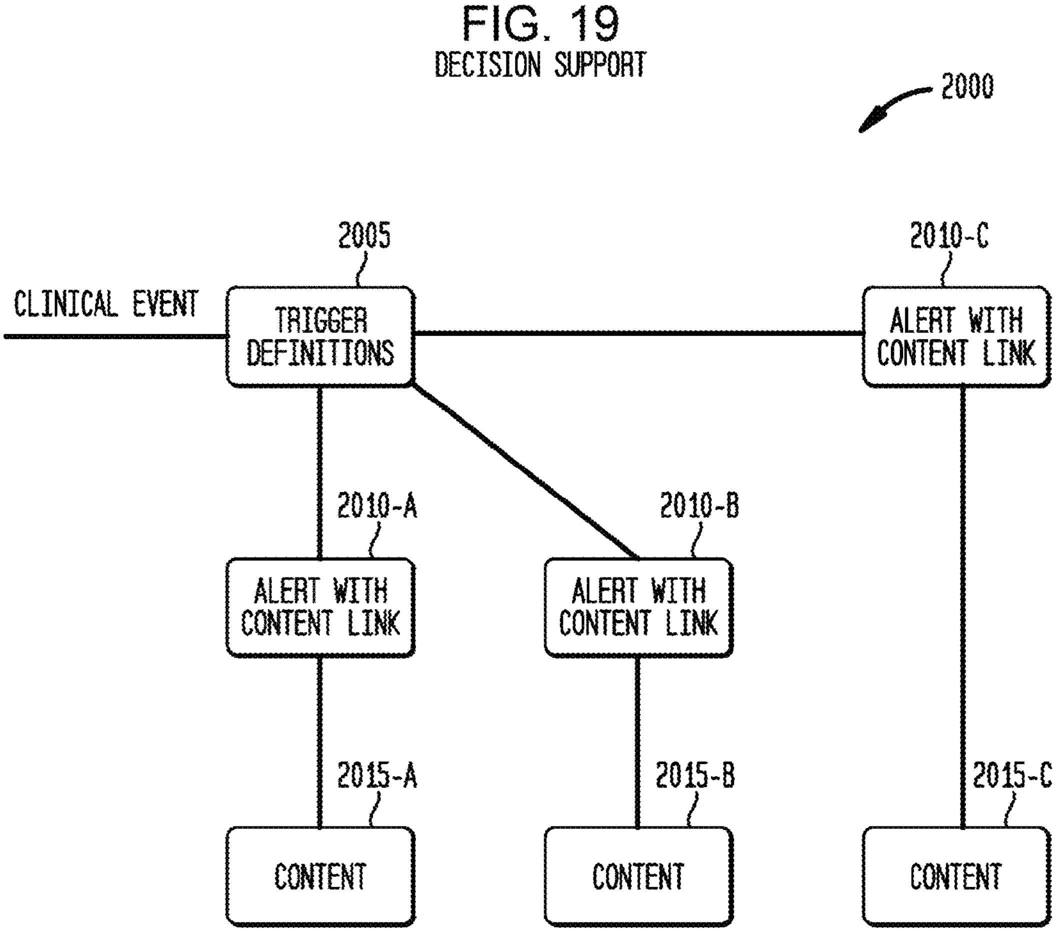
FIG. 19 is a flow diagram of feedback support provided to a medical professional in accordance some embodiments of the present disclosure.

FIG. 19 is a flow diagram 2000 illustrating an alert system of the COTA module providing an alert to a medical professional, a system of a medical provider, or a payer, or a system of a payer, in accordance with some embodiments. In one embodiment, the information in the alert aids the user in making a decision regarding future action. In one embodiment, the information in the alert is regarding some past action, past result or change in state. In one embodiment, the information provided both proactively influences decisions of the user and reactively provides a digest report of how the medical personnel did in the past week, month, quarter, etc. In one embodiment, there are different alerts for different users, each of which can influence decisions that the user makes. The alert may be employed for real time course correction to drive best value, such as, e.g., where an administered therapy deviates from a desired outcome. In block 2005, definitions are triggered based on clinical data. The definitions may be triggered using any criteria, such as, e.g., new disease diagnosis, disease progression, patient response, change in patient characteristics, dose change/drug toxicity change, trend towards variance from a desire outcome, etc. The criteria may be adjusted based on the disease and its parameters. Based on the triggered definitions, alerts 2010-A, 2010-B, 2010-C (collectively referred to as alerts 2010) are transmitted. It should be understood that alerts 2010 may include any number of alerts. The alerts 2010 may include content or a link to content. The alerts 2010 may be transmitted to the responsible physician, other medical professionals, hospital, pharmaceutical company, payer for medical services, or any other person or entity.

Content 2015-A, 2015-B, 2015-C (collectively referred to as content 2015) is displayed, e.g., using user computing device 210 to provide the alert. The content 2015 may include the patient data associated with the alert 2010, a comparison, or any other relevant content. In one embodiment, the comparison may be, e.g., between physicians, between one physician's patients and the whole patient population, between one physician and all physicians at a particular location, etc. The comparison may be based on a trending analysis to show where treatment is trending and if it is going off course (i.e., results are not as good as the standard). The comparison may be graphically displayed as one or more curves on a graph. In one embodiment, the COTA module 220 is utilized with cloud-based computing. The COTA module 220 can also enable or utilize connectivity to hospital records.

In one embodiment, the content 2015 may include feedback support to the medical professional. In some embodiments, the feedback may graphical symbols or indicators. For example, the feedback may include traffic light feedback indicators (not shown) on a display. For example, blue may mean very good performance (i.e., better than standard), green may mean standard performance, yellow may mean sufficient performance but may need to pay attention, red may mean the user may need to pay attention to something regarding the medical professional's approach to this disease. Other implementations of feedback indicators may also be employed.

Figure 20:
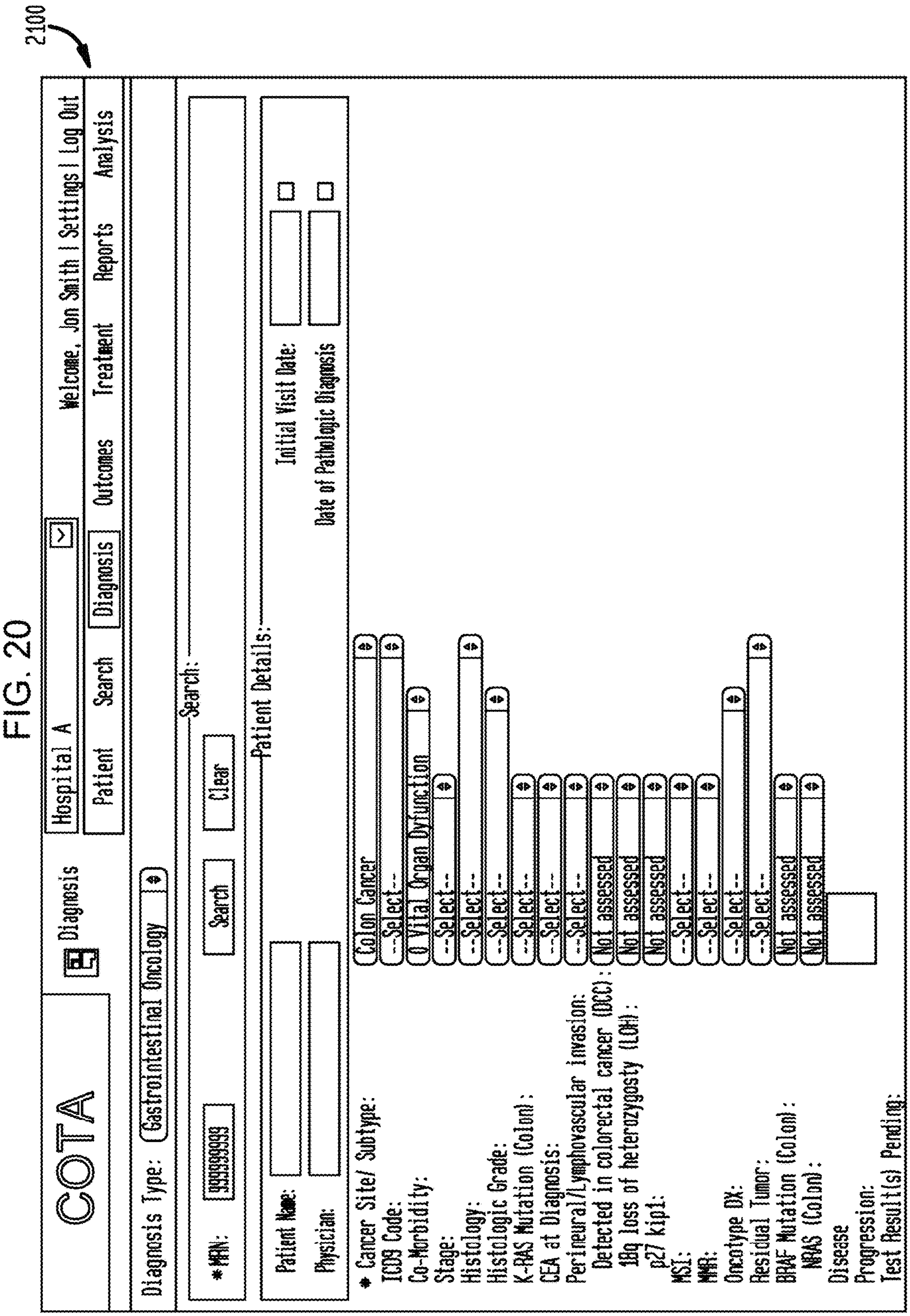
FIGS. 20-22 depict graphical user interfaces including treatment relevant variables and prognosis or outcome relevant variables for different diagnosis types in accordance with some embodiment of the present disclosure.
Figure 21:
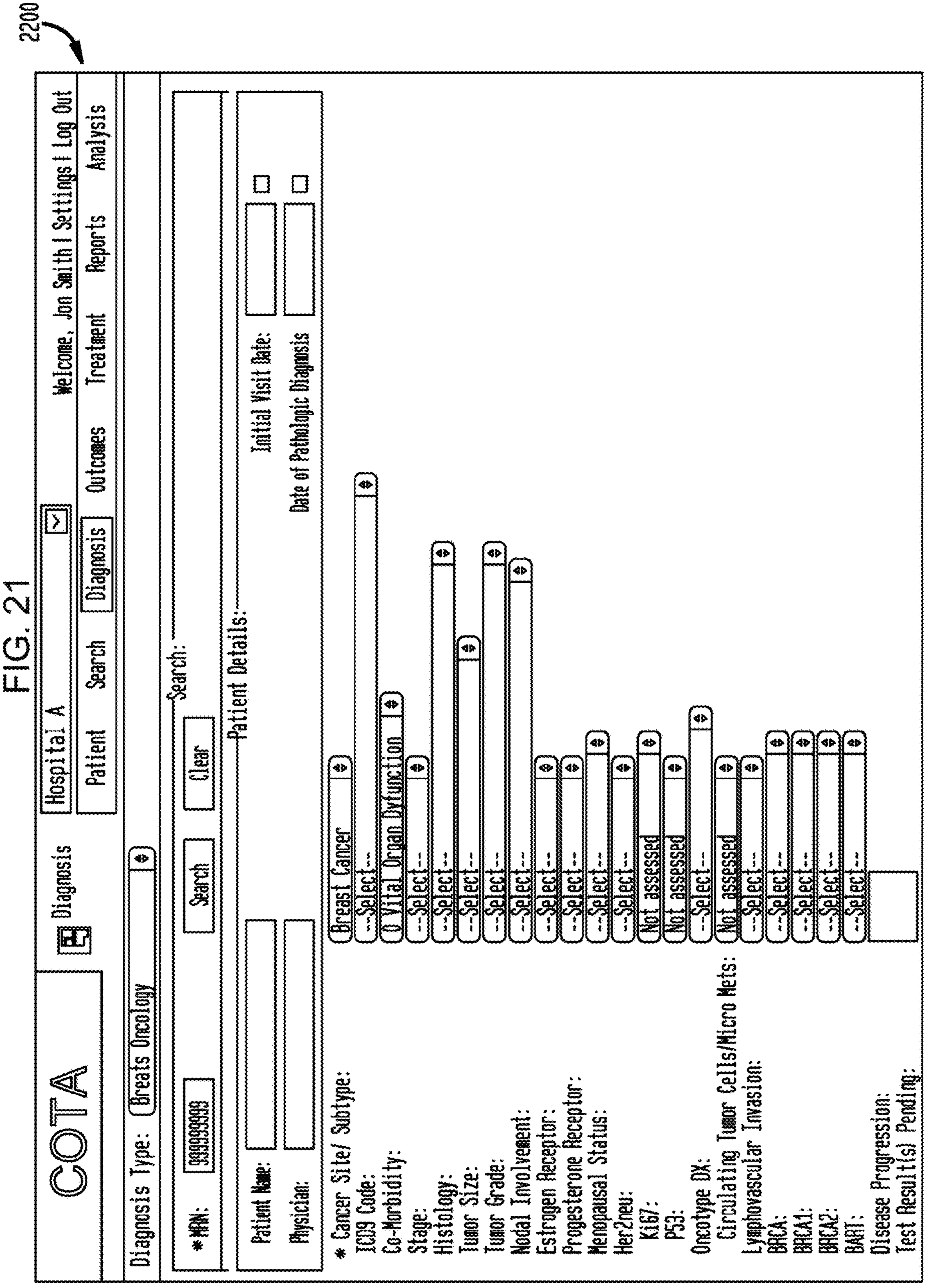
Figure 22:
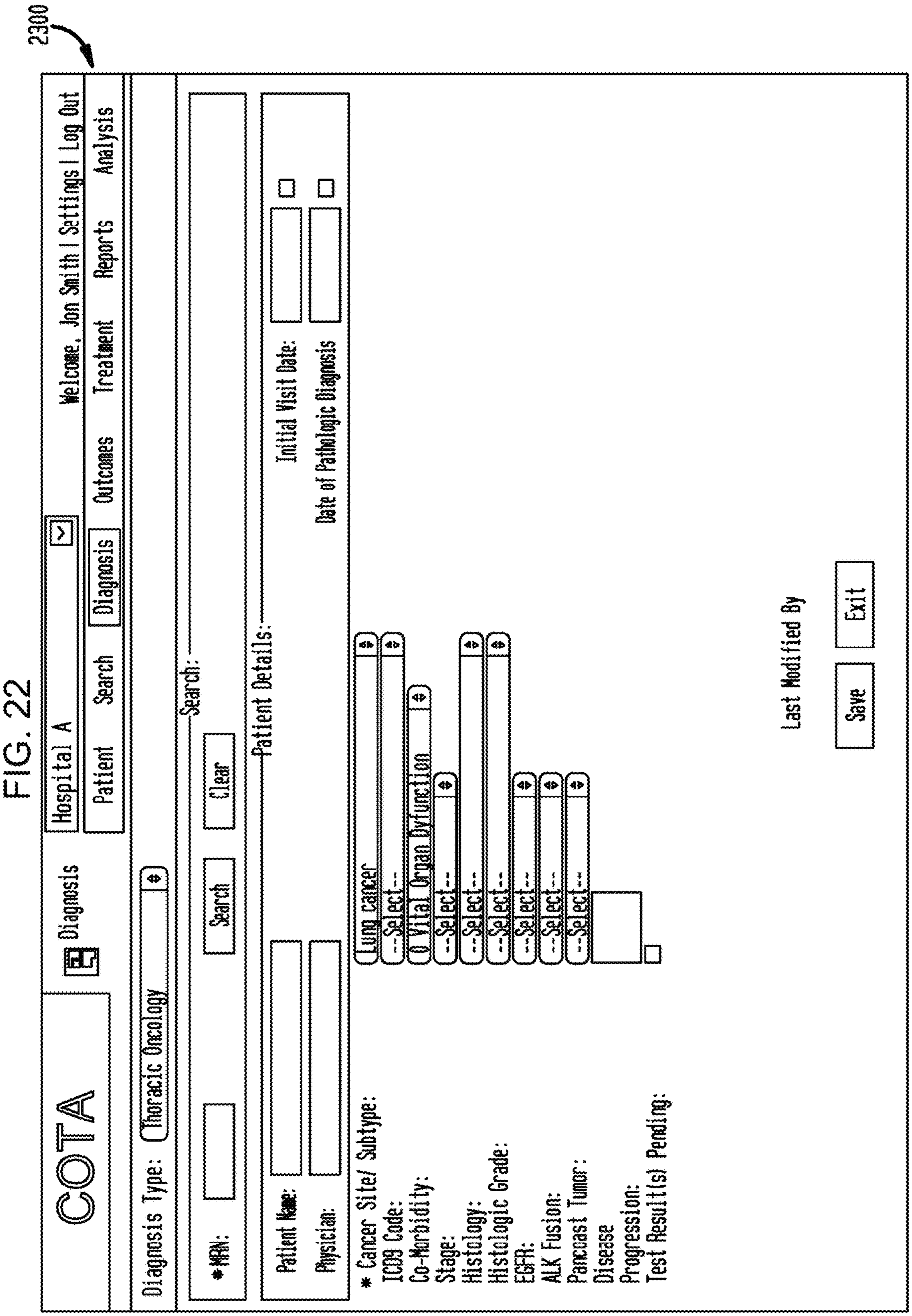

FIGS. 20-22 show graphical representations for different diagnosis types in accordance with one or more embodiments. FIG. 20 shows a diagnosis screen 2100 for gastrointestinal oncology (e.g., colon cancer). For colon cancer with adjuvant treatment intent, ECOG status, stage and comorbidity would be a minimum subset of treatment-relevant variables that must have attributes for assignment of a provisional nodal address. Information about comorbidity and cancer site are the only information available. Therefore, less than the minimum subset of treatment-related variables have attributes and more information must be provided for a provisional nodal address to be assigned to the patient. FIG. 21 shows a diagnosis screen 2200 for breast oncology (e.g., breast cancer). For adjuvant treatment intent for breast cancer, the minimum subset of treatment relevant variables include therapy type, sex, TNM, ECOG status, treatment relevant co-morbidity, histologic grade, histology, Her2 status, ER status, PR status, lymphovascular invasion; and menopausal status. Information about comorbidity and cancer site are the only information available as shown. Therefore less than a minimum subset of treatment-related variables have values for this patient and more information must be provided to assign a provisional nodal address to the patient. FIG. 22 shows a diagnosis screen 2300 for thoracic oncology (e.g., lung cancer). For non-small cell lung cancer (NSCLC) with an adjuvant/neoadjuvant treatment intent, stage, histology, ECOG and comorbidities would be a minimum subset of treatment relevant variables. Information about comorbidity and cancer site are the only information available. Therefore, less than a minimum subset of treatment relevant variables have values for this patient and more information must be provided to assign a provisional nodal address to the patient. Diagnosis screens 2100, 2200, 2300 include a number of different parameters, such as tests or aspects of the disease. The parameters may be represented as simple indicators, numerically based parameters, standards based parameters, etc.

In some embodiments, a diagnosis screen may include guides, areas, or menus to select or enter values for first predetermined variables that determine what other values are included in the minimum subset of treatment relevant variables, and guides, areas, windows or menus to select or enter values for the other variables in the minimum subset of predetermined variables may be presented based on the values selected for the first predetermined variables. For example, in some embodiments, an initial screen or section of a screen may include active guides, windows, menus or areas to enter values for the cancer site/subtype and treatment intent, and guides, windows, menus or areas to enter values for the others of the minimum subset of predetermined treatment relevant variables may be displayed or become active in response to or based on the values entered for the cancer site/subtype and the treatment intent. In some embodiments, guides, windows, menus or areas to enter values for the minimum subset of treatment relevant variables may be separated from or visually distinguishable from the guides, windows, menus or areas to enter values for predetermined variables that are not part of the minimum subset of treatment relevant variables. In this manner, the user interface may guide entry of information for the minimum subset of treatment relevant variables in some embodiments.

Figure 23:
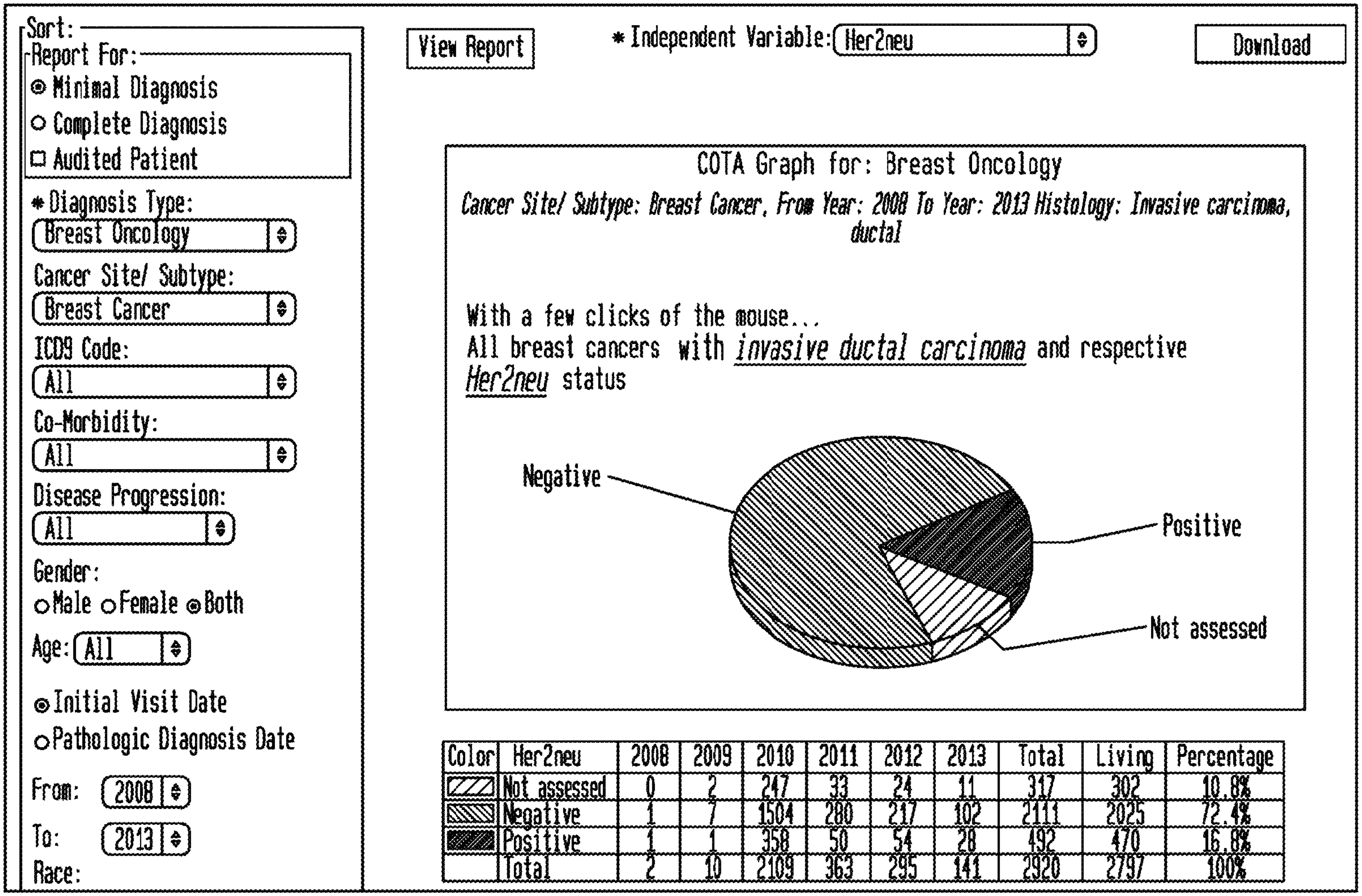
FIG. 23 depicts a graphical user interface including a graphical representation illustrating the COTA module's data generation and sorting for breast oncology—breast cancer from year 2008 to year 2013 histology with invasive ductal carcinoma and correlates the Her2neu status with outcome (i.e., overall survival/living) in accordance with an embodiment of the present disclosure.

FIG. 23 shows a graphical representation of a reporting screen 2400 illustrating the COTA module 220's data generation and sorting for breast oncology. Reporting screen 2400 shows breast cancer from year 2008 to year 2013 by histology, i.e., with invasive ductal carcinoma, in accordance with one embodiment. Histology is an example of a treatment relevant variable for breast cancer for adjuvant therapeutic intent, and is an outcome element for neoadjuvant therapeutic intent. The graph indicates Her2neu status for patients with invasive ductal carcinoma, and the table correlates Her2neu status with outcome (i.e., overall survival/living): 72% of patients that are negative for Her2neu were alive, while 16.8% of all patients positive for Her2neu were alive. Therefore histology type (invasive ductal carcinoma) and Her2neu status of the tumor together are prognostic indicators. The reporting screen 2400 permits selection of breast cancer patients based on stage, age, progression, or any other parameter in real time using the refined nodal address of each patient. Advantageously, reporting screen 2400 allows categorization in a clinically relevant way.

Figure 24:
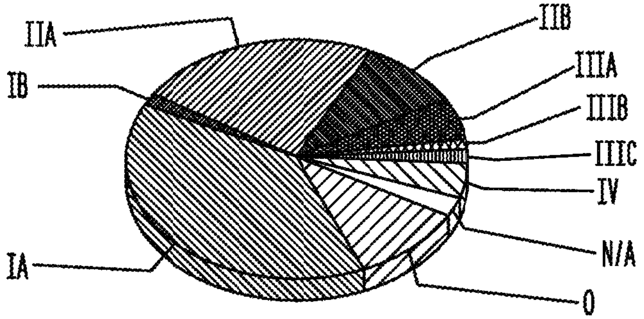
FIG. 24 depicts a graphical user interface including a graphical representation illustrating the COTA module's data generation and sorting for breast oncology—breast cancer from year 2008 to year 2013 tumor grade and stage in accordance with an embodiment of the present disclosure.

FIG. 24 shows a graphical representation of a reporting screen 2500 illustrating the COTA module's data generation and sorting for breast oncology. Reporting screen 2500 shows all grade 2 breast cancer from year 2008 to year 2013 tumor by stage, in accordance with one embodiment. Breast cancer stage is an example of a treatment relevant variable for breast cancer that is also a prognosis or outcome relevant variable (see column heading-living). Breast cancer stage is also a prognostic variable or attribute.

Figure 25:
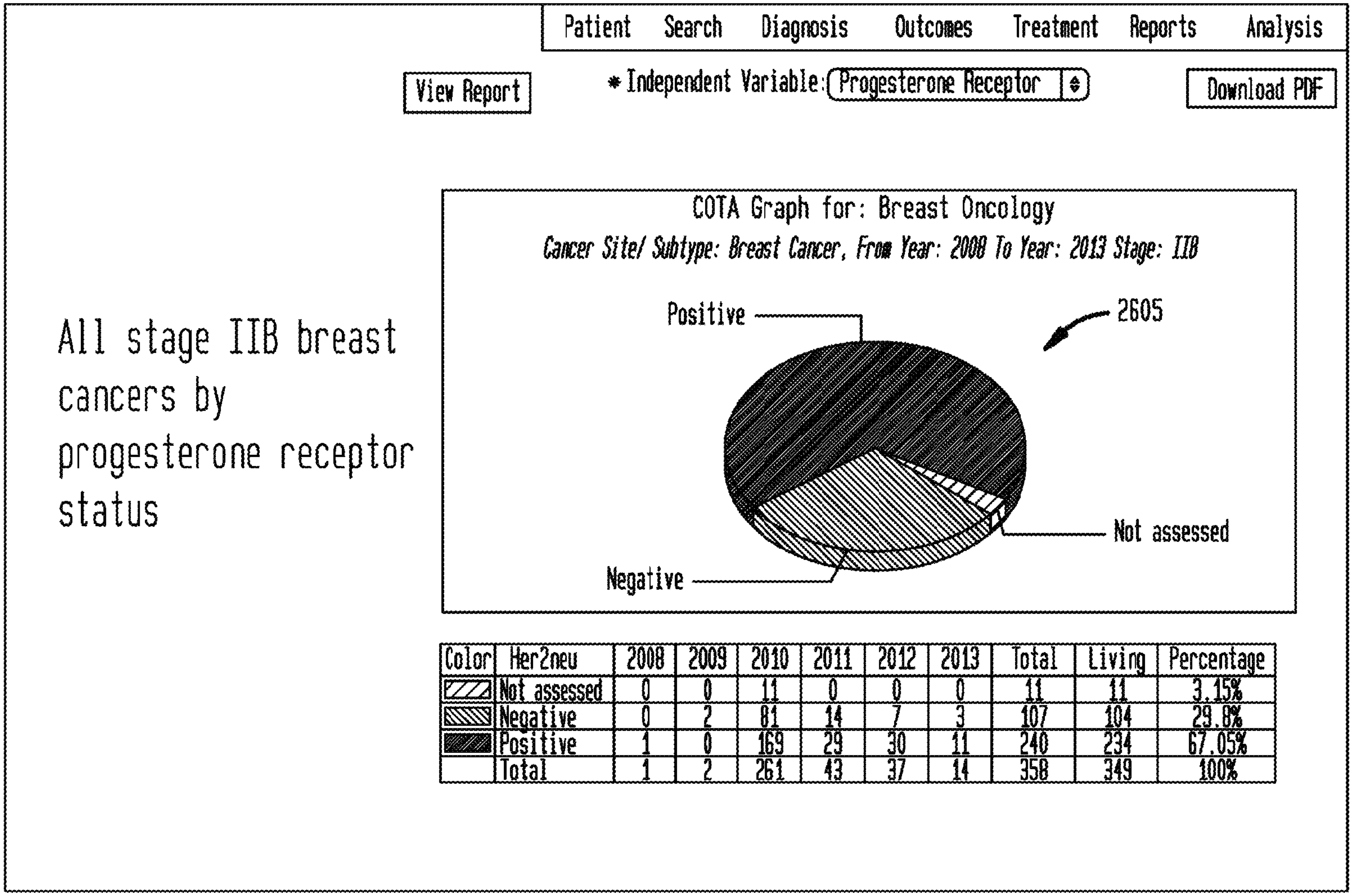
FIG. 25 depicts a graphical user interface including a graphical representation illustrating the COTA module's data generation and sorting for breast cancer—stage IIB from year 2008 to 2013 in accordance with an embodiment of the present disclosure.

FIG. 25 shows a graphical representation of a reporting screen 2600 illustrating the COTA module 220's data generation and sorting for breast cancer. Reporting screen 2600 shows all stage IIB breast cancers from year 2008 to 2013, in accordance with one embodiment. Graph 2605 on reporting screen 2600 shows all stage IIB breast cancers by progesterone receptor status. Progesterone receptor status is an example of a treatment relevant variable for breast cancer that is also a prognosis or outcome relevant variable (see column heading-living).

Figure 26:
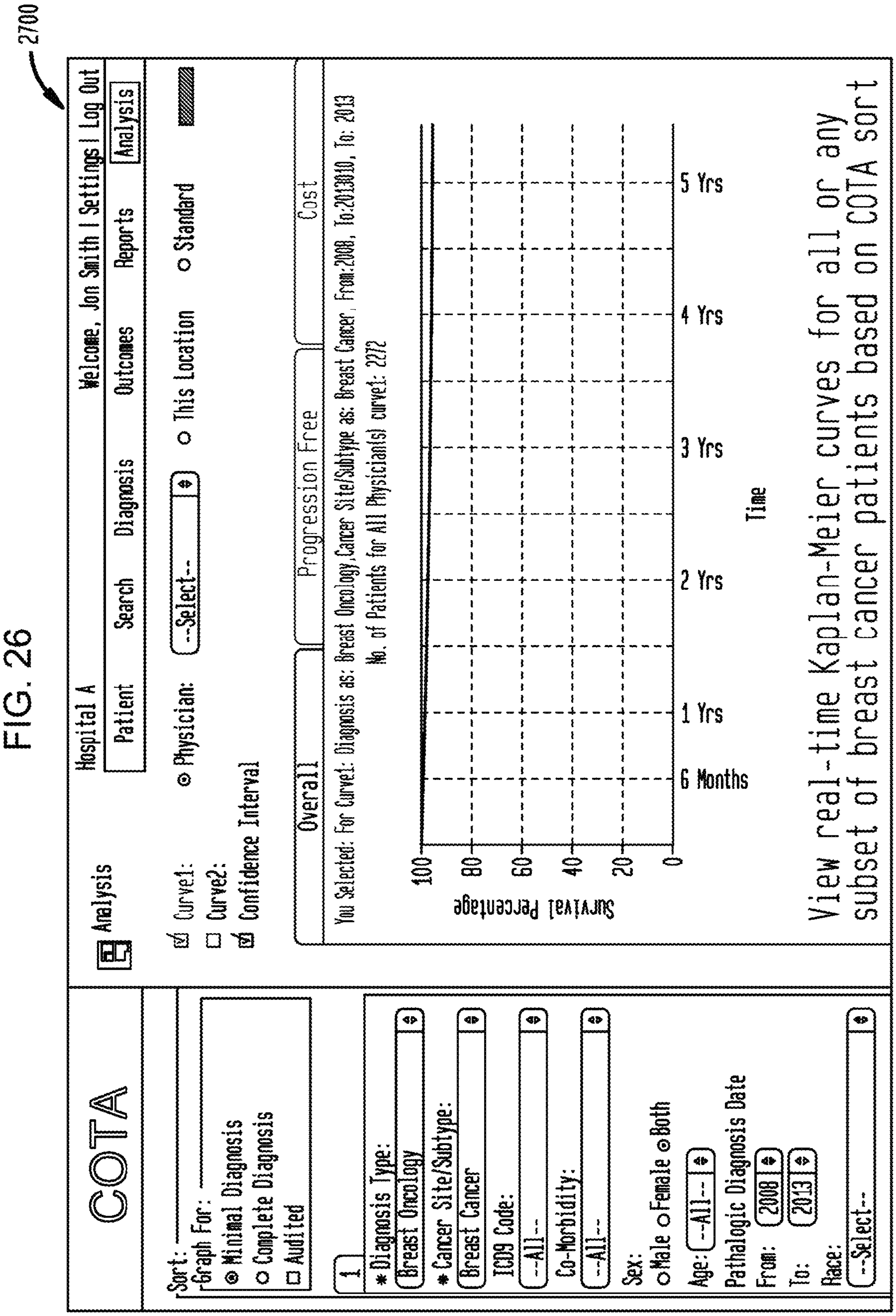
FIG. 26 depicts a graphical user interface including a graphical representation illustrating overall survival outcomes for breast cancer patients in accordance with an embodiment of the present disclosure.

FIG. 26 shows a graphical representation of an analysis screen 2700 illustrating overall survival outcomes for breast cancer patients in accordance with one embodiment. This is an example of a standard expected outcome for breast cancer that is not specific to a refined nodal address or prognosis or outcome based group associated with a refined nodal address.

Figure 27:
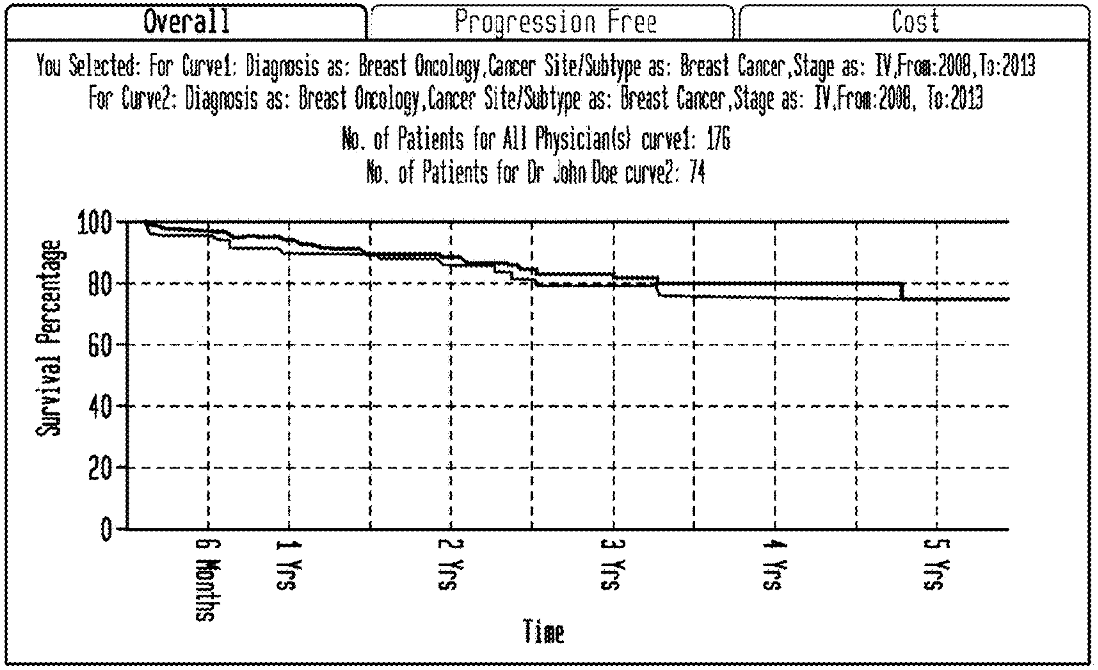
FIG. 27 depicts a graphical user interface including a graphical representation illustrating outcomes for breast cancer, specifically, a comparison between two parties, in accordance with an embodiment of the present disclosure.
Figure 27:

FIG. 27 shows a graphical representation 2800 illustrating survival outcomes for breast cancer as a comparison between Dr. John Doe (bold line) and the aggregate (non-bold line) parties, in accordance with one embodiment. This screen illustrates analyzing influence of non-biological factors such as differences in treatment among providers, on patient outcome, which can be used to identify providers whose outcomes are trending away from a standard.

In one embodiment, the "node" data element or nodal address described above can represent every permutation of the variables shown in one or more of the graphical representations (e.g., in one or more of FIGS. 20-26). In some embodiments, the node data element or nodal addresses described above can represent every permutation of variables that appears in patient data accessed by or available to the COTA module.

Figure 28:
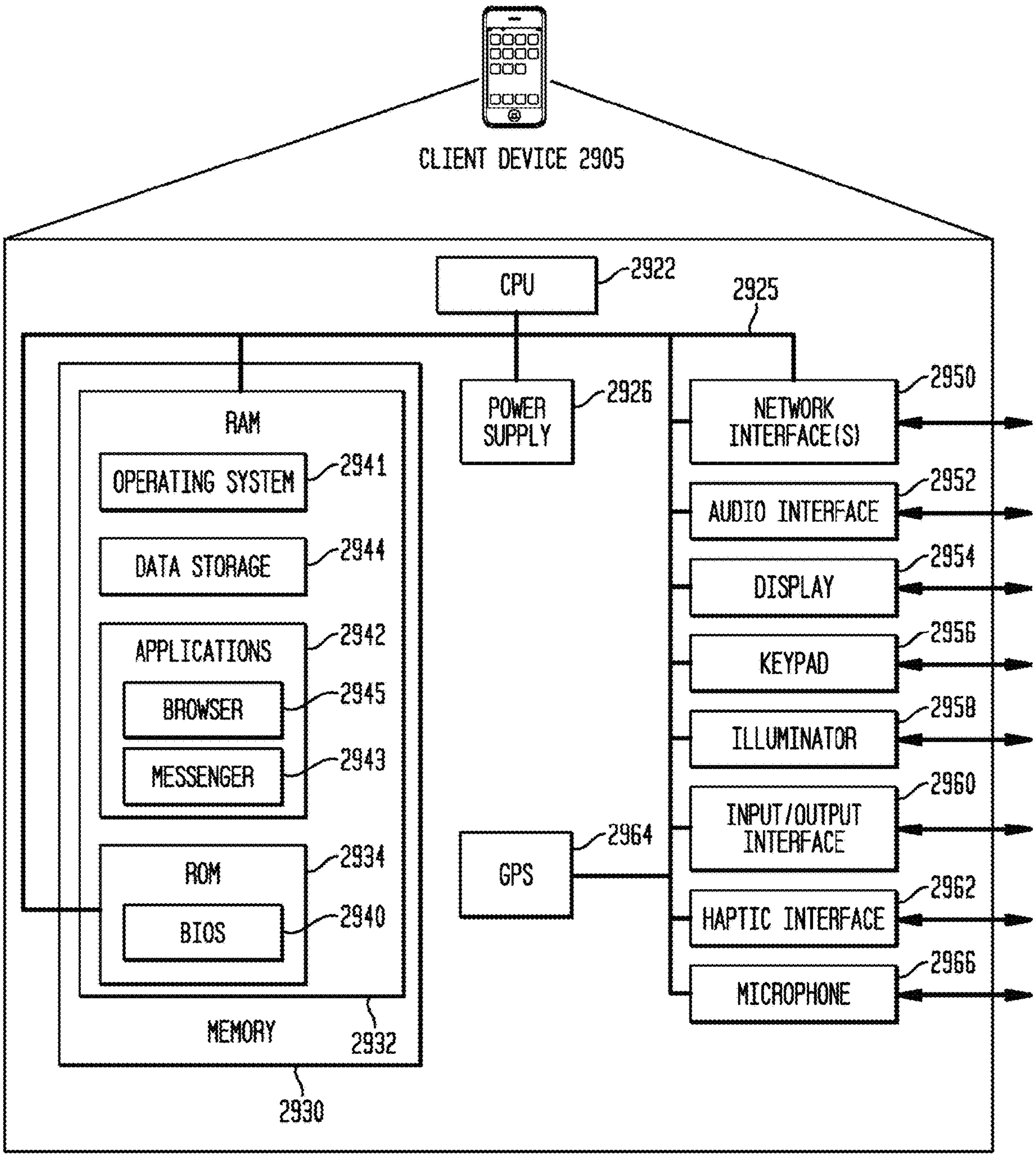
FIG. 28 schematically depicts a client device in accordance with an embodiment of the present disclosure.

As shown in the example of FIG. 28, client device 2905 may include one or more processing units (also referred to herein as CPUs) 2922, which interface with at least one computer bus 2925. Client device 2905 may be, for example, user computing device 210 or part of the computing system 205. A memory 2930 can be persistent storage and interfaces with the computer bus 2925. The memory 2930 includes RAM 2932 and ROM 2934. ROM 2934 includes a BIOS 2940. Memory 2930 interfaces with computer bus 2925 so as to provide information stored in memory 2930 to CPU 2922 during execution of software programs such as an operating system 2941, application programs 2942, device drivers, and software modules 2943, 2945 that include program code, and/or computer-executable process steps, incorporating functionality described herein, e.g., one or more of process flows described herein. CPU 2922 first loads computer-executable process steps from storage, e.g., memory 2932, data storage medium/media 2944, removable media drive, and/or other storage device. CPU 2922 can then execute the stored process steps in order to execute the loaded computer-executable process steps. Stored data, e.g., data stored by a storage device, can be accessed by CPU 2922 during the execution of computer-executable process steps.

Persistent storage medium/media 2944 is a computer readable storage medium(s) that can be used to store software and data, e.g., an operating system and one or more application programs. Persistent storage medium/media 2944 can also be used to store device drivers, such as one or more of a digital camera driver, monitor driver, printer driver, scanner driver, or other device drivers, web pages, content files, playlists and other files. Persistent storage medium/media 2206 can further include program modules and data files used to implement one or more embodiments of the present disclosure.

For the purposes of this disclosure a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data.

Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Client device 2905 can also include one or more of a power supply 2926, network interface 2950, audio interface 2952, a display 2954 (e.g., display 245 as shown in FIG. 2), keypad 2956, illuminator 2958, I/O interface 2960, a haptic interface 2962, a GPS 2964, a microphone 2966, a video camera, TV/radio tuner, audio/video capture card, sound card, analog audio input with A/D converter, modem, digital media input (HDMI, optical link), digital I/O ports (RS232, USB, FireWire, Thunderbolt), expansion slots (PCMCIA, ExpressCard, PCI, PCIe).

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may be grouped into an engine or an application.

Figure 29:
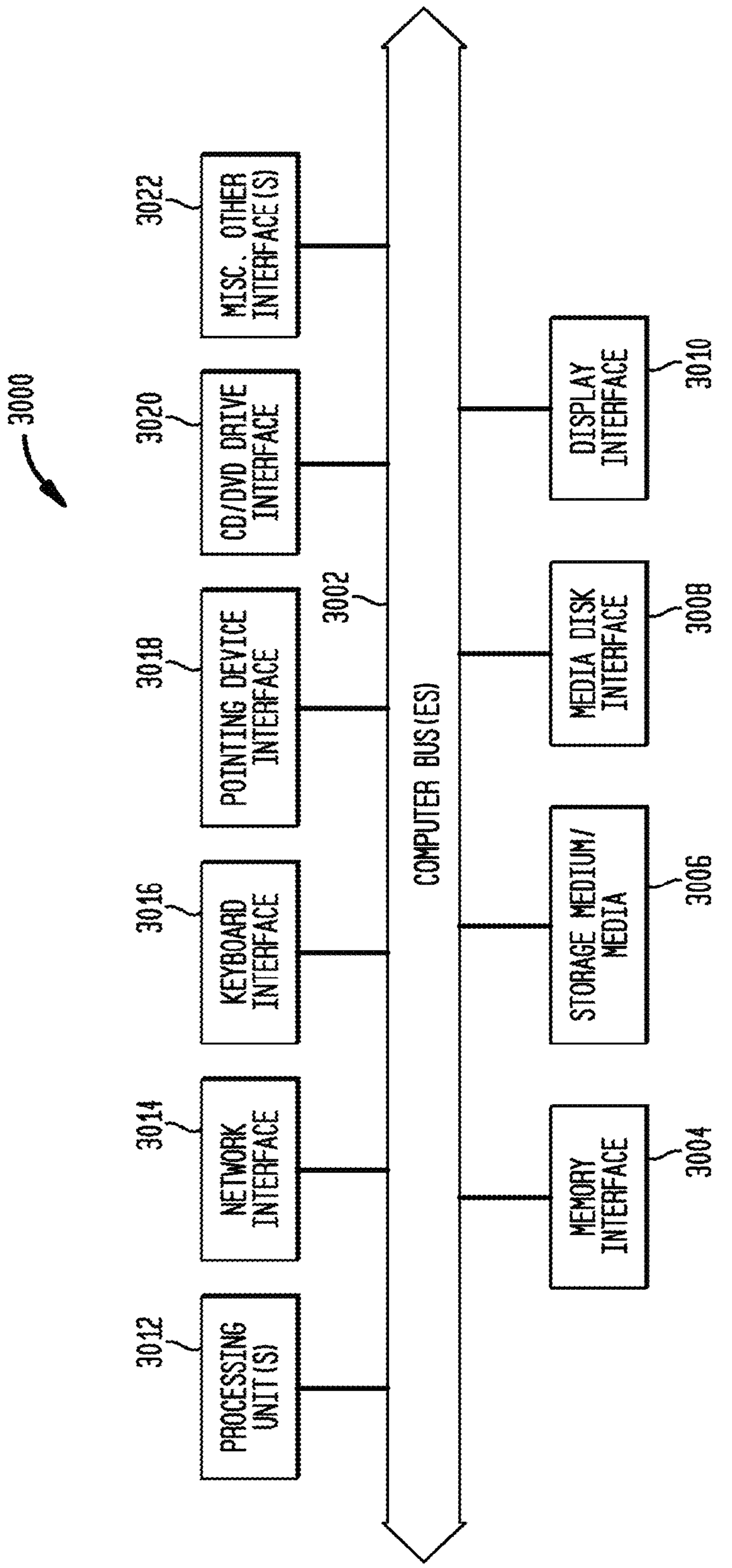
FIG. 29 is a block diagram schematically depicting an internal architecture of a computer in accordance with an embodiment of the present disclosure.

FIG. 28 is a block diagram illustrating an internal architecture of an example of a computer, such as computing system 205 and/or user computing device 210, in accordance with one or more embodiments of the present disclosure. A computer as referred to herein refers to any device with one or more processors capable of executing logic or coded instructions, and could be a server, personal computer, set top box, tablet, smart phone, pad computer or media device, to name a few such devices. As shown in the example of FIG. 29, internal architecture 3000 includes one or more processing units (also referred to herein as CPUs) 3012, which interface with at least one computer bus 3002. Also interfacing with computer bus 3002 are persistent storage medium/media 3006, network interface 3014, memory 3004, e.g., random access memory (RAM), run-time transient memory, read only memory (ROM), etc., media disk drive interface 2308 as an interface for a drive that can read and/or write to media including removable media such as floppy, CD-ROM, DVD, etc. media, display interface 3010 as interface for a monitor or other display device, keyboard interface 3016 as interface for a keyboard, pointing device interface 3018 as an interface for a mouse or other pointing device, and miscellaneous other interfaces not shown individually, such as parallel and serial port interfaces, a universal serial bus (USB) interface, and the like.

Memory 3004 interfaces with computer bus 3002 so as to provide information stored in memory 3004 to CPU 3012 during execution of software programs such as an operating system, application programs, device drivers, and software modules that comprise program code, and/or computer-executable process steps, incorporating functionality described herein, e.g., one or more of process flows described herein. CPU 3012 first loads computer-executable process steps from storage, e.g., memory 3004, storage medium/media 3006, removable media drive, and/or other storage device. CPU 3012 can then execute the stored process steps in order to execute the loaded computer-executable process steps. Stored data, e.g., data stored by a storage device, can be accessed by CPU 3012 during the execution of computer-executable process steps.

As described above, persistent storage medium/media 3006 is a computer readable storage medium(s) that can be used to store software and data, e.g., an operating system and one or more application programs. Persistent storage medium/media 3006 can also be used to store device drivers, such as one or more of a digital camera driver, monitor driver, printer driver, scanner driver, or other device drivers, web pages, content files, playlists and other files. Persistent storage medium/media 3006 can further include program modules and data files used to implement one or more embodiments of the present disclosure.

Internal architecture 3000 of the computer can include (as stated above), a microphone, video camera, TV/radio tuner, audio/video capture card, sound card, analog audio input with A/D converter, modem, digital media input (HDMI, optical link), digital I/O ports (RS232, USB, FireWire, Thunderbolt), and/or expansion slots (PCMCIA, ExpressCard, PCI, PCIe).

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the user computing device or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter. While the system and method have been described in terms of one or more embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method for updating nodal addresses to facilitate early treatment decisions and determine a prognosis-related expected outcome with respect to occurrence of a defined end point event for a patient of interest diagnosed with a disease with real-time detected information, the method comprising:

accessing or receiving, by a computing system, a first data set, via an Application Programming Interface (API), comprising personal health information associated with the patient of interest at a first time or over a first period of time, the personal health information including information regarding phenotypic characteristics;

assigning, by the computing system based on the received or accessed first set of data, attributes for at least some of a set of preselected variables, the set of preselected variables including a set of treatment relevant variables and a set of prognosis or outcome relevant variables;

in response to the computing system determining that the attributes are assigned for at least a minimum subset of the set of treatment relevant variables and less than a minimum subset of the prognosis or outcome relevant variables, and the computing system identifying insufficient personal health information in the first set of data to assign attributes to the minimum subset of the prognosis or outcome relevant variables, generating, by the computing system, a provisional nodal address to the patient of interest based on the assigned attributes for the set of treatment relevant variables, the provisional nodal address indicating a predetermined treatment plan information for facilitation of treatment decisions, the predetermined treatment plan information tailored to a specific combination of attributes used by the computing system to generate the provisional nodal address;

providing, by the computing system, the predetermined treatment plan information with which the provisional nodal address of the patient of interest is associated to a health care provider of the patient of interest to facilitate treatment decisions for the patient of interest;

detecting, by the computing system, a second set of data, pushed to the computing system via the API, including additional personal health information associated with the patient of interest at a second time later than the first time or over a second period of time later than the first period of time, the additional personal health information including updated personal health information relative to the first set of data associated with the patient of interest at the second time or over the second period of time;

in response to the computing system detecting the second set of data pushed to the computing system via the API, assigning, by the computing system based on the accessed or received second set of data, new attributes for preselected variables that did not previously have an assigned attribute due to insufficient personal health information in the first set of data to assign the attribute, or new attributes for preselected variables that did not previously have an assigned attribute due to insufficient personal health information in the first set of data to assign the attribute and updated attributes;

in response to the computing system determining that the attributes and the new attributes are assigned for at least the minimum subset of the treatment relevant variables and at least the minimum subset of the prognosis or outcome relevant variables:

generating, by the computing system, a refined nodal address to the patient of interest based on the current assigned attributes for the set of treatment relevant variables and the current assigned attributes for the set of prognosis or outcome relevant variables, the refined nodal address indicating an updated predetermined treatment plan information for facilitation of updated treatment decisions, the updated predetermined treatment plan information tailored to a specific combination of the current assigned attributes used by the computing system to generate the refined nodal address; and determining, by the computing system, the prognosis-related expected outcome with respect to occurrence of the defined end point event for the patient based on the refined nodal address assigned to the patient of interest; and in response to determining the prognosis-related expected outcome with respect to the occurrence of the defined end point event for the patient, pushing, via the API, by the computing system, the prognosis-related expected outcome with which the refined nodal address of the patient of interest is associated to a health care provider of the patient of interest to facilitate treatment decisions for the patient of interest.

2. The method of claim 1, (a) wherein the minimum subset of the treatment relevant variables is the treatment relevant variables in the set of preselected variables required to provide preselected treatment relevant information tailored to a patient's specific combination of treatment relevant attributes to guide a treatment decision; or (b) wherein the minimum subset of the treatment relevant variables for the patient of interest depends, at least in part, on a cancer type and a treatment intent for the patient of interest; or (c) wherein the minimum subset of the treatment relevant variables includes a cancer type and a treatment intent, and wherein what other of the treatment relevant variables are included in the minimum subset of the treatment relevant variables depends, at least in part, on the cancer type and the treatment intent for the patient of interest; or (d) wherein accessing or receiving the first data set comprising personal health information associated with the patient of interest at the first time or over the first period of time comprises accessing or receiving information regarding a cancer type and a treatment intent for the patient of interest; and wherein the method further comprises determining the minimum subset of the treatment relevant variables based, at least in part, on the accessed or received information regarding the cancer type and the treatment intent for the patient of interest; or (e) wherein the minimum subset of the prognosis or outcome relevant variables is all of the prognosis or outcome relevant variables in the set of preselected variables required for statistical analysis of prior outcomes; or (f) wherein the second set of data includes data obtained from health records of the patient of interest; or (g) wherein the first set of data includes data obtained from health records of the patient of interest; or (h) wherein the method further comprises assessing the first set of data to determine if it is correct prior to assigning the attributes for at least some of the set of preselected variables; or (i) wherein the predetermined treatment plan information includes information regarding one or more bundles of predetermined patient care services, and wherein providing the predetermined treatment plan information to the health care provider of the patient of interest comprises providing information regarding the one or more bundles of predetermined patient care services.

3. The method of claim 2, further comprising:

presenting to the patient and/or a health care provider for the patient a user interface for entry of data in the first data set; and receiving information regarding the cancer type of the patient of interest and the treatment intent for the patient of interest; and guiding entry of the rest of the minimum subset of the treatment relevant variables via the user interface, where the minimum subset of the treatment relevant variables depends, at least in part, on the cancer type of the patient of interest and the treatment intent for the patient of interest.

4. The method of claim 1, (a) further comprising presenting to the patient and/or a health care provider for the patient a user interface for entry of data in the first data set; or (b) further comprising after accessing or receiving the second set of data, iteratively accessing updated or new data sets comprising personal health information associated with the patient; and, after accessing or receiving each updated or new data set:

assigning, based on the accessed or new data set, updated attributes for at least some of the set of preselected variables and/or attributes for preselected variables that did not previously have an assigned attribute; and where attributes are assigned for at least the minimum subset of the treatment relevant variables and at least the minimum subset of the prognosis or outcome relevant variables, assigning a refined nodal address or an updated refined nodal address to the patient of interest based on current assigned attributes for the set of treatment relevant variables and current assigned attributes for the set of prognosis or outcome relevant variables; or (c) further comprising:

receiving or accessing information regarding a change in the set of preselected variables including the addition of one or more variables to the set of treatment relevant variables and/or to the set of prognosis or outcome relevant variables;

assigning an attribute for at least one of the one or more variables added to the set of treatment relevant variables and/or to the set of prognosis or outcome relevant variables based on current personal health information associated with the patient of interest; and assigning a different refined nodal address to the patient of interest based on the assigned attributes for the treatment relevant variables and the prognosis or outcome relevant variables; or (d) where the predetermined treatment plan information associated with the provisional nodal address assigned to the patient changes before a treatment decision has been made or before a refined nodal address has been assigned to the patient of interest, the method further comprises providing current predetermined treatment plan information to the health care provider of the patient of interest; or (e) further comprising, providing an alert to health care provider of the patient of interest that the predetermined treatment plan information associated with the provisional nodal address assigned to the patient of interest has changed; or (f) further comprising generating the provisional nodal address based on the assigned attributes for the set of treatment relevant variables prior to assigning the provisional nodal address to the patient of interest; or (g) further comprising generating the refined nodal address based on the assigned treatment relevant variables and on the assigned prognosis or outcome relevant variables prior to assigning the refined nodal address to the patient of interest; or (h) further comprising:

assigning the patient of interest to a prognosis or outcome based group based on the refined nodal address assigned to the patient of interest;

measuring a behavioral variance for each of a plurality of medical care providers for a plurality of patients assigned to the prognosis or outcome based group; and identifying necessary care absent and/or unnecessary care being provided contributing to the measured behavioral variance for at least one of the medical care providers.

5. The method of claim 4, wherein the user interface guides the user in entry of at least the minimum subset of treatment relevant variables.

6. The method of claim 1, wherein the prognosis-related expected outcome for the patient of interest is determined from a statistical analysis of prior prognosis-related outcomes for patients in a prognosis or outcome based group of patients who were each assigned the same refined nodal address as that assigned to the patient of interest at a corresponding point in treatment and disease progression as that of the patient of interest.

7. The method of claim 6, (a) further comprising statistically analyzing the prior outcomes for patients in the prognosis or outcome based group of patients to determine a current expected prognosis-related outcome for the patient of interest; or (b) further comprising conducting an updated statistical analysis of the prior outcomes for patients in the prognosis or outcome based group of patients to determine an updated current expected prognosis-related outcome and storing information regarding the updated current expected prognosis-related outcome; or (c) further comprising transmitting information regarding the prognosis-related expected outcome to a client device associated with a health care provider of the patient or a payer for health care of the patient of interest; or (d) further comprising accessing information regarding billed costs for treatment of the patient of interest and determining a total cost for treatment of the patient of interest over a clinically relevant period; and comparing the expected cost for treatment of the patient of interest over the clinically relevant period with the total cost for treatment of the patient of interest over the clinically relevant period; or (e) further comprising comparing one or more outcomes for the patient of interest to one or more historical outcomes for the patients in the prognosis or outcome based group of patients who were each assigned the same refined nodal address as that assigned to the patient of interest at diagnosis or at progression to determine if the one or more outcomes for the patient of interest are trending away from a standard for the prognosis or outcome based group.

8. The method of claim 7, wherein the current expected prognosis-related outcome is time to progression from start of second line therapy to start of third line therapy, and wherein the patients in the prognosis or outcome based group of patients are patients who were each assigned at the start of second line therapy the same refined nodal address as that assigned to the patient of interest at the start of second line therapy.

9. The method of claim 7, wherein the updated statistical analysis is conducted periodically.

10. The method of claim 7, wherein the clinically relevant period is from diagnosis to death or cure.

11. The method of claim 7, further comprising:

where it is determined that one or more outcomes for the patient of interest are trending away from the standard for the prognosis or outcome based group, sending an alert to a health care provider or health payer of the patient of interest including information regarding the one or more outcomes that are trending away from the standard.

12. The method of claim 7, further comprising: where the total cost of treatment of the patient of interest over the clinically relevant period exceeds the expected cost for treatment of the patient of interest over the clinically relevant period by over a threshold amount, sending an alert to a health care provider or health payer of the patient of interest.

13. The method of claim 6, further comprising:

(a) accessing information regarding an outcome for the patient of interest;

comparing the outcome for the patient of interest to the determined prognosis-related expected outcome for the patient of interest; and transmitting information regarding the comparison to a health care provider for the patient or to a health care payer for the patient of interest; or (b) determining an expected cost of treatment of the patient of interest for the disease over a clinically relevant period based on cost of treatment for all patients in the prognosis or outcome based group of patients who were each assigned the same refined nodal address as that assigned to the patient of interest at a corresponding point in treatment and disease progression as that of the patient of interest.

14. The method of claim 13, wherein the refined nodal address assigned to the patient of interest has an associated expected cost of treatment for the disease from diagnosis to death or cure, the associated expected cost of treatment determined by statistically analyzing prior cost of treatment from diagnosis to death or cure for the patients in the prognosis or outcome based group of patients who were each assigned the same refined nodal address as that assigned to the patient of interest at diagnosis.

15. The method of claim 1, (a) wherein the second data set includes data indicating a progression of the disease after the first point in time or after the first period of time; or (b) wherein the first data set includes information regarding a first diagnosis and the second data set includes information regarding an updated diagnosis after the first diagnosis; or (c) wherein the second data set includes information regarding attributes for which no information or incomplete information was provided in the first data set; or (d) wherein the prognosis-related expected outcome with respect to occurrence of a defined end point event includes one or more of overall survival, progression free survival, or disease free survival.

16. A non-transitory computer readable medium comprising program instructions for updating nodal addresses to facilitate early treatment decisions and determine a prognosis-related expected outcome with respect to occurrence of a defined end point event for a patient of interest diagnosed with a disease with real-time detected information, wherein execution of the program instructions by one or more processors causes the one or more processors to perform the method of claim 1.

17. A system for updating nodal addresses to facilitate early treatment decisions and determine a prognosis-related expected outcome with respect to occurrence of a defined end point event for a patient of interest diagnosed with a disease with real-time detected information, the system comprising:

a computing system hosting an application and in communication with a database and one or more third party systems executing the application via an Application Programming Interface (API), the computing system configured to:

access or receive, via the API, a first data set comprising personal health information associated with the patient of interest at a first time or over a first period of time, the personal health information including information regarding phenotypic characteristics;

assign, based on the accessed or received first set of data, attributes for at least some of a set of preselected variables, the set of preselected variables including a set of treatment relevant variables and a set of prognosis or outcome relevant variables;

in response to the computing system determining that the attributes are assigned for at least a minimum subset of the set of treatment relevant variables and less than a minimum subset of the prognosis or outcome relevant variables and less than a minimum subset of the prognosis or outcome relevant variables, wherein the computing system identifies insufficient personal health information in the first set of data to assign attributes to the minimum subset of the prognosis or outcome relevant variables, generate a provisional nodal address to the patient of interest based on the assigned attributes for the set of treatment relevant variables, the provisional nodal address indicating a predetermined treatment plan information for facilitation of treatment decisions, the predetermined treatment plan information tailored to a specific combination of attributes used by the computing system to generate the provisional nodal address;

provide to at least one third party system of the one or more third party systems of a health care provider of the patient of interest the predetermined treatment plan information with which the provisional nodal address of the patient of interest is associated;

detecting, a second set of data, pushed via the API, including additional personal health information associated with the patient of interest at a second time later than the first time or over a second period of time later than the first period of time, the additional personal health information including updated personal health information relative to the first set of data associated with the patient of interest at the second time or over the second period of time;

in response to detecting the second set of data being pushed via the API, assign, based on the accessed or received second set of data, new attributes for preselected variables that did not previously have an assigned attribute, or new attributes for preselected variables that did not previously have an assigned attribute and updated attributes;

in response to the computing system determining that the attributes and the new attributes are assigned for at least the minimum subset of the treatment relevant variables and at least the minimum subset of the prognosis or outcome relevant variables:

generate a refined nodal address to the patient of interest based on the current assigned attributes for the set of treatment relevant variables and the current assigned attributes for the set of prognosis or outcome relevant variables, the refined nodal address indicating an updated predetermined treatment plan information for facilitation of updated treatment decisions, the updated predetermined treatment plan information tailored to a specific combination of the current assigned attributes used to generate the refined nodal address; and determine the prognosis-related expected outcome with respect to occurrence of the defined end point event for the patient of interest based on the refined nodal address assigned to the patient of interest; and in response to determining the prognosis-related expected outcome with respect to the occurrence of the defined end point event for the patient, pushing, via the API, the prognosis-related expected outcome with which the refined nodal address of the patient of interest is associated to a health care provider of the patient of interest to facilitate treatment decisions for the patient of interest.

18. The system of claim 17, (a) wherein the minimum subset of the treatment relevant variables is treatment relevant variables in the set of preselected variables that are required to provide preselected treatment relevant information tailored to a patient's specific combination of treatment relevant attributes to guide a treatment decision; or (b) wherein the minimum subset of the treatment relevant variables for the patient of interest depends, at least in part, on a cancer type and a treatment intent for the patient of interest; or (c) wherein the minimum subset of the treatment relevant variables includes a cancer type and a treatment intent, and wherein what other of the treatment relevant variables are included in the minimum subset of the treatment relevant variables depends, at least in part, on the cancer type and the treatment intent for the patient of interest; or (d) wherein accessing or receiving the first data set comprising personal health information associated with the patient of interest at the first time or over the first period of time comprises accessing or receiving information regarding a cancer type and a treatment intent for the patient of interest; and wherein the method further comprises determining the minimum subset of the treatment relevant variables based, at least in part, on the accessed or received information regarding the cancer type and the treatment intent for the patient of interest; or (e) wherein the minimum subset of the prognosis or outcome relevant variables is all of the prognosis or outcome relevant variables in the set of preselected variables required for statistical analysis of prior outcomes; or (f) wherein the second set of data includes data obtained from health records of the patient of interest; or (g) wherein the first set of data includes data obtained from health records of the patient of interest; or (h) wherein the method further comprises assessing the first set of data to determine if it is correct prior to assigning the attributes for at least some of the set of preselected variables; or (i) wherein the predetermined treatment plan information includes information regarding one or more bundles of predetermined patient care services, and wherein providing the predetermined treatment plan information to the health care provider of the patient of interest comprises providing information regarding the one or more bundles of predetermined patient care services.

19. The system of claim 18, wherein the computing system is further configured to:

present to the patient and/or a health care provider for the patient a user interface for entry of data in the first data set;

receive information regarding the cancer type of the patient of interest and the treatment intent for the patient of interest; and after the determination of the minimum subset of the treatment relevant variables based on the received information regarding the cancer type of the patient of interest and the treatment intent for the patient of interest, guide entry of the rest of the minimum subset of the treatment relevant variables via the user interface, where the minimum subset of the treatment relevant variables depends, at least in part, on the cancer type of the patient of interest and the treatment intent for the patient of interest.

20. The system of claim 17, (a) wherein the computing system is further configured to present to the patient and/or a health care provider for the patient a user interface for entry of data in the first data set; or (b) wherein the computing system is further configured to after accessing or receiving the second set of data, iteratively access or receive updated or new data sets comprising personal health information associated with the patient; and after accessing or receiving each updated or new data set:

assign, based on the accessed or new data set, updated attributes for at least some of the set of preselected variables and/or attributes for preselected variables that did not previously have an assigned attribute; and where attributes are assigned for at least the minimum subset of the treatment relevant variables and at least the minimum subset of the prognosis or outcome relevant variables, assign a refined nodal address or an updated refined nodal address to the patient of interest based on current assigned attributes for the set of treatment relevant variables and current assigned attributes for the set of prognosis or outcome relevant variables; or (c) wherein the computing system is further configured to:

receive or access information regarding a change in the set of preselected variables including the addition of one or more variables to the set of treatment relevant variables and/or to the set of prognosis or outcome relevant variables;

assign an attribute for at least one of the one or more variables added to the set of treatment relevant variables and/or to the set of prognosis or outcome relevant variables based on current personal health information associated with the patient of interest; and assign a different refined nodal address to the patient of interest based on the assigned attributes for the treatment relevant variables and the prognosis or outcome relevant variables; or (d) wherein before a treatment decision has been made or before a refined nodal address has been assigned to the patient of interest, where the predetermined treatment plan information associated with the provisional nodal address of the patient of interest changes, the computing system is further configured to provide current predetermined treatment plan information to the health care provider of the patient of interest; or (e) wherein the computing system is further configured to provide an alert to health care provider of the patient of interest that the predetermined treatment plan information associated with the provisional nodal address assigned to the patient of interest has changed; or (f) wherein the computing system is further configured to generate the provisional nodal address based on the assigned attributes for the set of treatment relevant variables prior to assigning the provisional nodal address to the patient of interest; or (g) wherein the computing system is further configured to generate the refined nodal address based on the assigned treatment relevant variables and on the assigned prognosis or outcome relevant variables prior to assigning the refined nodal address to the patient of interest; or (h) wherein the computing system is further configured to:

assign the patient of interest to a prognosis or outcome based group based on the refined nodal address assigned to the patient of interest;

measure a behavioral variance for each of a plurality of medical care providers for a plurality of patients assigned to the prognosis or outcome based group; and identify necessary care absent and/or unnecessary care being provided contributing to the measured behavioral variance for at least one of the medical care providers.

21. The system of claim 20, wherein the user interface guides the user in entry of at least the minimum subset of treatment relevant variables.

22. The system of claim 17, wherein the prognosis-related expected outcome for the patient of interest is determined from a statistical analysis of prior prognosis-related outcomes for patients in a prognosis or outcome based group of patients who were each assigned to the same refined nodal address as that assigned to patient of interest at a corresponding point in treatment and disease progression as that of the patient of interest.

23. The system of claim 22, (a) wherein the computing system is further configured to statistically analyze the prior outcomes for patients in the prognosis or outcome based group of patients to determine a current expected prognosis-related outcome for the patient of interest; or (b) wherein the computing system is further configured to conduct an updated statistical analysis of the prior outcomes for patients in the prognosis or outcome based group of patients to determine an updated current expected prognosis-related outcome and store information regarding the updated current expected prognosis-related outcome; or (c) wherein the computing system is further configured to: transmit information regarding the prognosis-related expected outcome to a client device associated with a health care provider of the patient or a payer for health care of the patient of interest; or (d) wherein the computing system is further configured to access information regarding billed costs for treatment of the patient of interest and determine a total cost for treatment of the patient of interest over a clinically relevant period; and compare the expected cost for treatment of the patient of interest over a clinically relevant period with the total cost for treatment of the patient of interest over the clinically relevant period; or (e) wherein the computing system is further configured to:

compare one or more outcomes for the patient of interest to one or more historical outcomes for patients in the prognosis or outcome based group who were each assigned the same refined nodal address as that assigned to the patient of interest at diagnosis or at progression to determine if the one or more outcomes for the patient of interest are trending away from a standard for the prognosis or outcome based group.

24. The system of claim 23, wherein the current expected prognosis-related outcome is time to progression from start of second line therapy to start of third line therapy, and wherein the patients in the prognosis or outcome based group of patients are patients who were each assigned at the start of second line therapy to the same refined nodal address as that assigned to the patient of interest at the start of second line therapy.

25. The system of claim 23, wherein computing system is configured to conduct the updated statistical analysis periodically.

26. The system of claim 23, wherein the clinically relevant period is from diagnosis to death or cure.

27. The system of claim 23, wherein the computing system is further configured to:

determine whether one or more outcomes for the patient of interest are trending away from the standard for the prognosis or outcome based group, and where it is determined that the one or more outcomes for the patient of interest are trending away from the standard, send an alert to a health care provider or health payer of the patient of interest including information regarding the one or more outcomes that are trending away from the standard.

28. The system of claim 23, where the computing system is further configured to determine whether the total cost of treatment of the patient of interest over the clinically relevant period exceeds the expected cost for treatment of the patient of interest over the clinically relevant period by over a threshold amount, and where the total cost of treatment exceeds the expected cost of treatment, to send an alert to a health care provider or health payer of the patient of interest.

29. The system of claim 22, wherein the computing system is further configured to:

(a) access information regarding an outcome for the patient of interest;

compare the outcome for the patient of interest to the determined prognosis-related expected outcome for the patient of interest; and transmit information regarding the comparison to a health care provider for the patient or to a health care payer for the patient of interest; or (b) determine an expected cost of treatment of the patient of interest for the disease over a clinically relevant period based on cost of treatment for all patients assigned to a prognosis or outcome based group of patients who were each assigned to the same refined nodal address as that assigned to the patient of interest at a corresponding point in treatment and disease progression as that of the patient of interest.

30. The system of claim 29, wherein the refined nodal address assigned to the patient of interest has an associated expected cost of treatment for the disease from diagnosis to death or cure, the associated expected cost of treatment determined by statistically analyzing prior cost of treatment from diagnosis to death or cure for the patients in the prognosis or outcome based group of patients who were each assigned the same refined nodal address as that assigned to the patient of interest at diagnosis.

31. The system of claim 17, (a) wherein the second data set includes data indicating a progression of the disease after the first point in time or after the first period of time; or (b) wherein the first data set includes information regarding a first diagnosis and the second data set includes information regarding an updated diagnosis after the first diagnosis; or (c) wherein the second data set includes information regarding attributes for which no information or incomplete information was provided in the first data set; or (d) wherein the prognosis-related expected outcome with respect to occurrence of a defined end point event includes one or more of overall survival, progression free survival, or disease free survival.

* * * * *